United States Patent [19]

Dervan et al.

[11] Patent Number: 4,942,227
[45] Date of Patent: Jul. 17, 1990

[54] BIFUNCTIONAL MOLECULES HAVING A DNA INTERCALATOR OR DNA GROOVE BINDER LINKED TO ETHYLENE DIAMINE TETRAACETIC ACID, THEIR PREPARATION AND USE TO CLEAVE DNA

[75] Inventors: Peter B. Dervan, Pasadena, Calif.; Robert P. Hertzberg, Downingtown, Pa.

[73] Assignee: California Institute of Technology, Pasadena, Calif.

[21] Appl. No.: 6,442

[22] Filed: Jan. 23, 1987

Related U.S. Application Data

[63] Continuation-in-part of Ser. No. 860,604, May 7, 1986, Pat. No. 4,665,184, which is a continuation of Ser. No. 540,914, Oct. 12, 1983, abandoned, which is a continuation-in-part of Ser. No. 338,327, Jan. 11, 1982, abandoned.

[51] Int. Cl.$^5$ ............................................. C07H 21/00
[52] U.S. Cl. ........................................ 536/27; 536/28; 536/29; 546/109; 548/403
[58] Field of Search ................. 536/27, 28, 29; 514/44

[56] References Cited

U.S. PATENT DOCUMENTS 4,665,184  5/1987  Dervan et al. ..................... 546/109

OTHER PUBLICATIONS

Schultz et al., The Chemical Abstracts, 100: 2875w (1984).
Hertzberg et al., The Chemical Abstracts, 101: 67951h (1984).
Taylor et al., The Chemical Abstracts, 101: 3453q (1984).
Schultz et al., The Chemical Abstracts, 100: 205156k (1984).
Van Dyke, Science, 225, pp. 1122–1126 (1984).

Primary Examiner—John W. Rollins
Assistant Examiner—James O. Wilson
Attorney, Agent, or Firm—Joseph E. Mueth

[57] ABSTRACT

Bifunctional molecules having a DNA intercalator or DNA groove binder linked to ethylene diamine tetraacetic acid such as compounds having the formula:

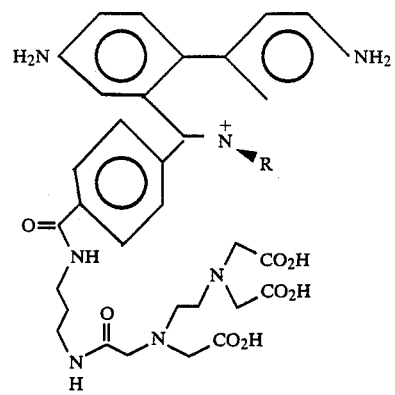

wherein R is methyl or ethyl.

Also, the method of cleaving DNA by contact with one of the above-identified molecules in the presence of ferrous ion and oxygen.

The process of preparing said molecules by the reaction of P-carboxy methidium halide, p-carboxy ethidium halide, or other DNA intercalator or DNA groove binder with 1-3-diaminopropane followed by condensation with ethylenediamine tetraacetic acid.

Distamycin-EDTA.Fe(II)(DE.FE(II)) contains EDTA attached to the amino terminus of the groove binder tripeptide (tris-N-methylpyrrolecarboxamide). De.-Fe(II) cleaves DNA contiguous to a five base pair A+T rich sequence. This is a novel and unique molecule and superior in sequence specificity to the naturally occurring antitumor compound used in man, bleomycin which cleaves DNA at a two base pair recognition site. EDTA-distamycin-Fe(II)(ED.Fe(II)) contains EDTA attached to the carboxy terminus of the groove binder tripeptide, tris-N-methylpyrrolecarboxamide. ED.-Fe(II) cleaves DNA contiguous to a five base pair A+T rich sequence. Penta-N-methylpyrrolecarboxamide-EDTA.Fe(II)(P5E.Fe(II)) cleaves on opposite strands at the six base pair recognition level in a catalytic reaction. This is the first designed synthetic molecule that approximates the double strand sequence specific cleavage of DNA(4–6 bp recognition level) by the natural substance restriction enzymes, tools which make possible recombinant DNA manipulations. P5E.-Fe(II) cuts DNA at sequences not available by the naturally occurring restriction enzymes.

The dimers, bis(EDTA-distamycin.Fe(II)) and EDTA-bisdistamycin.Fe(II) which double strand cleave DNA at the eight base pair recognition level (A+T rich).

8 Claims, No Drawings

BIFUNCTIONAL MOLECULES HAVING A DNA INTERCALATOR OR DNA GROOVE BINDER LINKED TO ETHYLENE DIAMINE TETRAACETIC ACID, THEIR PREPARATION AND USE TO CLEAVE DNA

This application is a continuation-in-part of Ser. No. 860,604 filed May 7, 1986, now U.S. Pat. No. 4,665,184 issued on May 12, 1987, which was continuation of Ser. No. 540,914, now abandoned, filed Oct. 12, 1983, which was a continuation-in-part of Ser. No. 338,332 filed Jan. 11, 1982, both now abandoned.

BACKGROUND OF THE INVENTION

Metal ions have been implicated as cofactors in the strand scission of DNA for a number of antitumor antibiotics. Bleomycin, a glycopeptide antibiotic, is known to bind to and cleave DNA in a reaction that depends on the presence of ferrous ion and molecular oxygen, "Bleomycin: Chemical, Biochemical and Biological Aspects"; Hecht, S. M., Ed.; Springer Verlag: New York, 1979; Sausville, E. A.; Peisach, J.; Horwitz, S. B. "Biochemistry" 1978, 17, 2740. Burger, R. M.; Peisach, J; Horwitz, S. B. "Life Sciences" 1981, 28, 715; and Lown, J. W.; Sim, S. F. "Biochem. Biophys. Res. Comm. " 1977, 77, 1150. The antitumor agent streptonigrin is also capable of causing single strand breaks in DNA using oxygen and cuprous ion, Cone, R; Hasan, S. K.; Lown, J. W.; Morgan, A. R. "Can. J. Biochem." 1976, 54, 219. Recently, the 1–10 phenanthroline-cuprous complex has been shown to cleave DNA in the presence of oxygen, Sigman, D. S.; Graham, D. R.; D'Aurora, V.; Stern, A. M. "J. Biol. Chem." 1979, 254, 12269; Graham, D. R.; Marshall, L. E.; Reich, K. A.; Sigman, D. S. "J. Amer. Chem. Soc." 1980, 102, 5419; Marshall, L. E.; Graham, D. R.; Reich, K. A.; Sigman, D. S. "Biochemistry" 1981, 20, 244; and Que, B. G.; Downey, K. M.; So., A. G. "Biochemistry" 1980, 19, 5987, These examples involve the concept of using a DNA binding molecule to deliver a metal ion to the site of the DNA helix where activation of molecular oxygen results in cleavage of the DNA.

According to the present invention, we have discovered a class of new bifunctional molecules containing a DNA intercalator or DNA groove binder molecule linked to ethylene diamine tetraacetic acid. An example of our invention is the synthesis of a simple bifunctional molecule, methidium-propyl-EDTA (MPE) which contains the DNA intercalator, methidium or ethidium covalently bound by a short hydrocarbon tether to the metal chelator, ethylene diamine tetraacetic acid. In the presence of ferrous ion and oxygen, MPE has been discovered to efficiently produce single strand breaks and some double strand breaks in double helical DNA with lower sequence specificity than the naturally occurring enzyme, DNase I. The efficient and low sequence specific DNA cleaving ability of MP.Fe(II) afford a new synthetic tool for DNA and RNA manipulations superior to the naturally occurring enzyme DNase I.

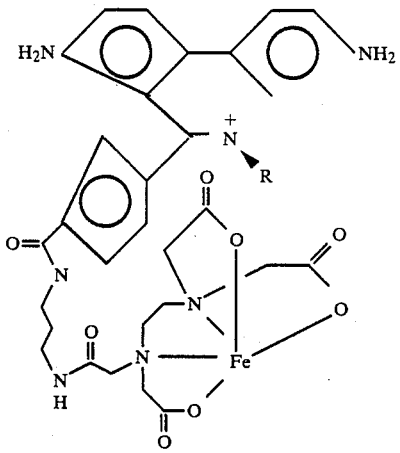

In the above formula R is methyl or ethyl.

The novel compounds distamycin EDTA.Fe(II), EDTA-distamycin.FE(II), penta-N-methylpyrrolecarboxamide-EDTA.Fe(II), bis(EDTA-distamycin).Fe(II) and EDTA(bisdistamycin).Fe(II) are effective as sequence specific DNA cleavers.

SUMMARY OF THE INVENTION

Briefly the present invention comprises novel bifunctional molecules having a DNA intercalator or DNA groove binder linked to ethylene diamine tetracetic acid (EDTA) such as compounds having the formula:

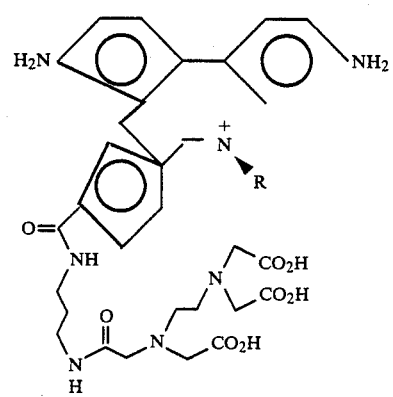

wherein R is methyl or ethyl; distamycin EDTA; EDTA distamycin; penta-N-methylpyrrolecarboxamide EDTA; bis(EDTA distamycin) and EDTA-(bisdistamycin).

The present invention further includes the preparation of the compounds of the structural formula, known as methidium (or ethidium)-propyl-ethylene-diamine tetraacetic acid by the reaction of p-carboxy methidium halide or p-carboxy ethidium halide with 1,3-diaminopropane followed by condensation with ethylenediamine tetraacetic acid. DNA intercalators are a known class of compounds that bind noncovalently to duplex DNA and are characterized by a flat molecule which inserts between base pairs of the double helix of DNA. Examples include p-carboxy methidium, p-carboxy ethidium, acridine and ellipticine.

DNA groove binders are also a recognized group of DNA binders and are characterized by their ability to fit snuggly within the grooves of the DNA helix. Examples of DNA groove binders are netropsin, distamycin and actinomycin.

This invention also comprehends the method of cleaving DNA by contact with any one of the above-identified molecules linked to EDTA in the presence of ferrous ion and oxygen.

It is an object of this invention to provide a novel class of chemical compounds.

Still another object of this invention is the novel process of preparing certain new chemical compounds.

It is also an object of this invention to provide a novel means for cleaving the DNA molecule.

These and other objects and advantages of the invention will be apparent from the detailed description which follows.

DESCRIPTION OF THE PREFERRED EMBODIMENTS OF THE INVENTION

The following Examples are presented solely to illustrate the invention.

The method of preparation of one category of the new compounds is shown by the following reaction equation:

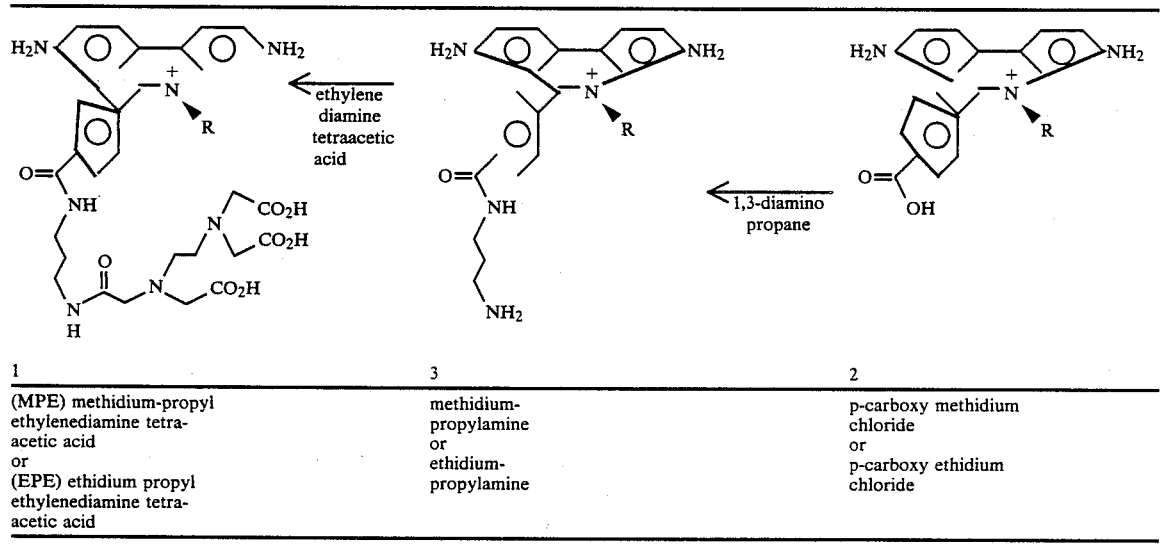

| 1 | 3 | 2 |
|---|---|---|
| (MPE) methidium-propyl ethylenediamine tetra-acetic acid or (EPE) ethidium propyl ethylenediamine tetra-acetic acid | methidium-propylamine or ethidium-propylamine | p-carboxy methidium chloride or p-carboxy ethidium chloride |

EXAMPLE I

The acylimidazole ester of p-carboxy methidium chloride (obtained from May-Baker), was allowed to react with an excess of 1,3-diaminopropane in dimethyl sulfoxide (DMSO) at 25° affording a maroon solid product, methidiumpropylamine (3). Condensation of 3 with excess EDTA in dry DMF/120° yielded methidium-propyl-EDTA (MPE), in an overall yield of 59% after chromatography on silica gel 60 (230-400 mesh ASTM). MPE was rendered metal-free by treatment of an acidic aqueous solution with Na$_2$EDTA followed by purification of Amberlite XAD-2 polystyrene resin.*

*MPE was ≧99% pure by HPLC in two solvent systems (ALTEX Ultrasphere ODS; 86:14 H$_2$O:CH$_3$CN, retention time 8.4 minutes and 70:30 H$_2$O:MeOH, retention time 19.2 minutes). The nmr and ir spectra data were consistent with the assigned structure. MPE was isolated from methanol/water as the hexahydrate. Anal. Calcd. for C$_{34}$H$_{51}$N$_7$O$_{14}$: C, 52.23; H, 6.57; N, 12.54. Found: C, 52.48; H, 6.12; N, 12.50.

EXAMPLE II

In the following, the cleavage of DNA was followed by monitoring the conversion of supercoiled (Form 1) pBR-322 plasmid DNA, $10^{-5}$M in base pairs (bp), to open circular and linear forms (Forms 11 and 111, respectively). The introduction of one single strand break converts Form 1 to Form 11. The simple chelate of ethylene diamine tetraacetic acid with ferrous ion, EDTA.Fe(II), at $>10^{-4}$M concentrations will cleave plasmid DNA, however at concentrations $\leq 10^{-4}$M little or no cleavage takes place. The addition of intercalator ethidium bromide (EB) to Fe (II) or EDTA.Fe(II) does not promote the cleavage reaction. Thus, we believe it is notable that MPE.Fe(II) at two orders of magnitude lower concentration ($10^{-6}$M) cleaves plasmid DNA (Table I). MPE alone or MPE.Fe(III) is inactive at these concentrations. In the presence of dithiothreitol (DTT), MPE.Fe(II) at $10^{-8}$M concentration cleaves plasmid DNA with even greater efficiencies, comparable to efficiencies found with bleomycin (Table II). Presumably, DTT acts as a reducing agent and regenerates Fe(II) from Fe(III) to produce a continuous source of active metal ion.

TABLE I

Cleavage of pBR-322 Plasmid$^a$

| Reagent | Concentration (M) | Percent Form I | II | III | $s^b$ |
|---|---|---|---|---|---|
| Fe(II) | $10^{-4}$ | 92 | 8 | 0 | 0.08 |
| EDTA.Fe (II)$^c$ | $10^{-4}$ | 94 | 6 | 0 | 0.06 |
| EDTA.Fe (II)$^c$ | $5 \times 10^{-4}$ | 38 | 62 | 0 | 0.97 |
| MPE.Fe (II) | $10^{-6}$ | 72 | 28 | 0 | 0.33 |
| MPE.Fe (II) | $5 \times 10^{-6}$ | 40 | 60 | 0 | 0.92 |
| Bleomycin.Fe (II) | $10^{-7}$ | 65 | 29 | 6 | |

TABLE I-continued

Cleavage of pBR-322 Plasmid[a]

| Reagent | Concentration (M) | Percent Form I | II | III | s[b] |
|---|---|---|---|---|---|
| Bleomycin.Fe (II) | $10^{-6}$ | 0 | 49 | 51 | |

[a]Form I pBR-322($10^{-5}$ M bp), reagent and buffer (40 mM Tris-HCl, 5 nM NaOAC, pH 7.8) were allowed to react at 37° for 60 min. Forms I, II, and III were analyzed with agarose gel electrophoresis and quantitated by ethidium bromide staining and densitometry.
[b]Calculated average number of strand scissions per DNA molecule. Theses values cannot be calculated for bleomycin because of a non-random accumulation of single-strand breaks.
[c]Values are the same for EDTA. Fe (II) in the presence of $10^{-5}$ M EB.

TABLE II

Cleavage of pBR-322 Plasmid in the Presence of DTT.[a]

| Reagent | Concentration (M) | Percent Form I | II | III | s[b] |
|---|---|---|---|---|---|
| MPE.Fe (II) | $10^{-8}$ | 82 | 18 | 0 | 0.20 |
|  | $10^{-7}$ | 43 | 57 | 0 | 0.84 |
|  | $10^{-6}$ | 0 | 85 | 15 | 9.2 |
| Bleomycin.Fe (II) | $10^{-8}$ | 67 | 29 | 4 | |
|  | $10^{-7}$ | 0 | 79 | 21 | |
|  | $10^{-6}$ | 0 | 54 | 46 | |
| Fe (II) | $10^{-6}$ | 90 | 10 | 0 | 0.11 |

[a]All reactions contain I mM DTT. Reaction conditions and analyses are as in Table I.

Inhibition studies reveal the following (Table III). Addition of Fe(II) to MPE in the presence of strong iron chelators such as desferrioxamine (Des) or EDTA shows no DNA cleavage. Addition of Fe(II) to MPE.Ni(II) or MPE.Zn(II) shows no DNA cleavage. Ni(II) and Zn(II) are known to form stable complexes with EDTA, and presumably compete with Fe(II) for the chelation site on MPE.

TABLE III

Inhibition Studies[a]

| Inhibitor | Concentration (M) | Percent Form I | II | III | S |
|---|---|---|---|---|---|
| none |  | 38 | 62 | 0 | 0.97 |
| EDTA | $10^{-2}$ | 86 | 14 | 0 | 0.15 |
| EDTA | $5 \times 10^{-2}$ | 94 | 6 | 0 | 0.06 |
| Des | $10^{-2}$ | 97 | 3 | 0 | 0.03 |
| Des | $5 \times 10^{-2}$ | 100 | 0 | 0 | 0.0 |
| Ni (II) | $10^{-4}$ | 98 | 2 | 0 | 0.02 |
| Zn (II) | $10^{-4}$ | 88 | 12 | 0 | 0.13 |
| Superoxide dismutase | 100 μg/ml | 81 | 19 | 0 | 0.21 |
| Catalase | 100 μg/ml | 96 | 4 | 0 | 0.04 |

[a]pBR-322 plasmid DMA ($10^{-5}$ M bp), MPE ($10^{-5}$ M), and inhibitor were combined in buffer and then Fe (II) ($10^{-5}$ M) was added. Analysis was carried out as in Table I.

The reactions of MPE.Fe(II) and plasmid DNA with and without DTT were repeated in the absence of oxygen and no strand scission was observed. The nature of the activated oxygen species in the MPE.Fe(II) reaction which cleaves the DNA is not yet known. While not bound by any theory, two classes of intermediates that might be considered as the ultimate DNA-cleaving species are free oxygen radicals or an iron-bound oxygen species, Groves, J. T. "Metal Ion Activation of Dioxygen"; Spiro, T. C., Ed.; John Wiley and Sons, New York, 1980; p. 146. Superoxide ion ($O_2^{\doteq}$) has been shown to be involved in the single-strand scission of DNA in the presence of trace metal ions, Lesko, S. A.; Lorentzen, R. J.; Ts'l, P.O.P. "Biochemistry" 1980, 19, 3023. Superoxide has also been implicated as an intermediate in the reaction mechanisms of bleomycin, streptonigrin, and Cu-phenanthroline. In these systems, hydroxyl radicals are suggested to be at least one ultimate species which degrades DNA. Hydrogen peroxide has been implicated as an intermediate in the hydroxyl radical generation by known Fenton-type chemistry.

The enzyme superoxide dismutase (SOD) converts superoxide to hydrogen peroxide and oxygen, Malstrom, B. G.; Andreasson, L. E.; Reinhammar, B. in "The Enzymes:, Vol. XII; Boyer, P.D., Ed. Academic Press: New York, 1975, p. 533, thus depleting the system of "free" superoxide. The observation that SOD inhibits the MPE.Fe(II) cleavage of DNA indicates the importance of $O_2^{\doteq}$. Catalase, which converts hydrogen peroxide to water and oxygen, Schonbaum, G. R.; Chance, B. in "The Enzymes"; Vol. XIII; Boyer, P.D., Ed.; Academic Press: New York, 1976; p. 363, also inhibits the MPE.Fe(II) DNA cleavage reaction indicating the apparent importance of "free" hydrogen peroxide as an intermediate in strand scission (Table III).

With regard to iron-bound oxygen as the ultimate DNA cleaving species, it has been found that direct oxidation of MPE.Fe(III) ($10^{-5}$M) with iodosylbenzene (Ph10) ($10^{-5}$M) enhances cleavage of plasmid DNA. Whether this involves a ferryl species MPE(-Fe$^V$=O) will be the subject of future work. Controls show that Ph10 and EDTA.Fe(III) ($10^{-5}$M) or Ph10 ($10^{-5}$M) alone do not cleave DNA.

In summary, MPE cleaves plasmid DNA in a reaction that is dependent on Fe(II) and $O_2$ at concentrations of two orders of magnitude lower than EDTA.Fe(II). In the presence of DTT concentrations of MPE.Fe(II) as low as $10^{-8}$M cleave DNA comparable to efficiencies found with the antibiotic bleomycin. It appears that an interpretation consistent with the data suggests that the intercalator portion of MPE "delivers" the iron/oxygen chemistry to the DNA helix.

The present invention is useful in the efficient cleavage of plasmid DNA. The cleaved DNA is now widely used in a variety of processes and techniques familiar to those skilled in the art. It also appears that like bleomycin, MPE and EPE may be useful in cancer chemotherapy.

The attachment of EDTA.Fe(II) to distamycin changes the sequence specific DNA binding antibiotic into a sequence specific DNA cleaving molecule. This invention includes the snthesis of EDTA-distamycin(ED) which has the EDTA, tethered to the carboxy terminus of the N-methylpyrrole tripeptide moiety of the distamycin. EDTA-distamycin.Fe(II) (ED.Fe(II)) at $10^{-6}$M concentration efficiently cleaves pBR322 DNA ($10^{-5}$M in base pairs) in the presence of oxygen and dithiothreitol (DTT). Using Maxam-Gilbert sequencing gel analyses, it has been found that ED.Fe(II) affords DNA cleavage patterns of unequal intensity covering two to four contiguous base pairs adjacent to a four base pair site consisting of adenines (A) and thymines (T). The multiple cleavages at each site might be evidence for a diffusible oxidizing species, perhaps hydroxyl radical. The unequal intensity of cleavage on each side of the A+T site permit assignment of major and minor orientations of the tripeptide binding unit. A comparison of the cleavage specificity of ED.Fe(II) with distamycin-EDTA.Fe(II), (DE.Fe(II)) which has EDTA.Fe(II) attached to the amino terminus of the N-methylpyrrole tripeptide of the distamycin, shows DNA cleavage patterns at the same sites but with intensities of opposite polarity. Maxam-Bilbert sequencing gel analysis of the DNA cleavage patterns by ED.Fe(II) and DE.Fe(II) on both DNA strands of a 381 base pair restriction fragment reveals asymmetric DNA cleavage patterns. Cleavage is shifted to the 3' side of each DNA strand. A model consistent with this cleavage pattern indicates one preferred binding site for ED.Fe(II) and DE.Fe(II) is 3'-TTTAA-5' with the "amino end" of the tripeptide oriented to the 3' end of the thymine rich strand.

This "DNA affinity cleavage" method which consists of attaching cleaving functions such as a metal and chelator capable of redox chemistry to DNA binding molecules followed by DNA cleavage pattern analyses from Maxam-Gilbert sequencing gels may be a useful direct method for determining the binding site and orientation of small molecules on DNA. This strategy changes the function of sequence specific DNA binding molecules affording a new class of sequence specific DNA cleaving molecules that may form the primitive basis for the design and construction of "artificial restriction enzymes" with defined target sequences and binding site sizes.

Many small molecules important in antibiotic, antiviral, and antitumor chemotherapy bind to double helical DNA. Our knowledge of the base sequence preferences of most DNA binding drugs is somewhat limited due to the restricted information obtained by spectrophotometric analyses of the overall binding affinity on synthetic homopolymer and copolymer DNAs. A smaller class of DNA binding molecules are bifunctional in nature, combining a chemically reactive moiety with a DNA binding unit. One such molecule is the naturally occurring antitumor, antibiotic bleomycin which cleaves DNA in a reaction that depends on Fe(II) and oxygen. "Bleomycin: Chemical, Biochemical and Biological Aspects"; S. M. Hecht, Ed.; Springer-Verlag: New York, 1979. R. M. Burger, J. Peisach, S. B. Horowitz, *Life Sci.*, 28, 715–727 (1981). The DNA cleaving function of bleomycin in combination with Maxam-Gilbert sequencing gel analyses affords precise information on the sequence specificity of bleomycin binding. From DNA cleavage patterns obtained from reaction of bleomycin.Fe(II) with end labeled DNA restriction fragments it is known that bleomycin cleaves DNA at the pyrimidine of a two base pair 5'-GT-3' or 5'-GC-3' recognition site. M. Takeshita, L. Kappen, A. P. Grollman, M. Eisenberg, I. Goldberg, *Biochemistry*, 20, 7599–7606 (1981). M. Takeshita, Ap. P. Grollman, E. Ohtusbo, H. Ohtsubo, *Proc. Natl. Acad. Sci. U.S.A.*, 75, 5983–5987 (1978) A. D. D'Andrea, W. A. Haseltine, *Proc. Natl. Acad. Sci. U.S.A.*, 75, 3608–3612 (1978). The structure of the bleomycin.Fe(II):DNA complex is not known. Unlike bleomycin.Fe(II), MPE.Fe(II) cleaves DNA in a non-sequence specific manner consistent with spectrophotometric binding studies that indicate that methidium has no overall base composition specificity. (a) M. J. Waring, *J. Mol. Biol.*, 13, 269–282 (1965). J.-B. LePacq, C. Paoletti, *J. Mol. Biol.*, 27, 87–106 (1967). (b) W. Muller, D. M. Crothers, *Eur. J. Biochim.*, 54, 267–277 (1975). (c) J. L. Bresloff, D. M. Crothers, *Biochemistry*, 20, 3457–3552 (1981). The lack of sequence specificity in the DNA cleavage reaction suggests that MPE.Fe(II) mimics the function of DNase I, an enzyme which cleaves double helical DNA in a relatively non-sequence specific manner. (a) A. Bernardi, C. Gaqillard, G. B. Bernardi, *Eur. J. Biochim.*, 52, 451–457 (1975). (b) A. Bernardi, S. D. Ehrlich, J. Thiery, *Nature*, 246, 36–40 (1973). Because MPE.Fe(II) cleaves DNA with lower sequence specificity than DNase I, MPE.Fe(II) partial cleavage of drug protected DNA restriction fragments in combination with Maxam-Gilbert sequencing gel analysis of the DNA cleavage inhibition patterns provides a rapid and direct method called "MPE.Fe(II) footprinting" for determining the locations and size of the binding sites of small molecules on the native DNA template.

We understood the attachment of EDTA to sequence specific DNA binding molecules. We intend to change the "function" of sequence specific DNA binding molecules to sequence specific DNA cleaving molecules. The antibiotic distamycin is a tripeptide containing three N-methylpyrrole carboxamides which binds in the minor groove of douple helical DNA with a strong preference for adenine and thymine rich regions. (a) K. E. Reinert, *J. Mol. Biol.*, 72, 592 (1972). (b) G. Luck, Ch. Zimmer, K. E. Reinert, F. Arcamore, *Nucl. Acids Res.* 4, 2655 (1977). (c) B. Nosikov, B. Jain, *Nucl. Acids Res.*, 4, 2263 (1977). (d) For reviews see: Ch. Zimmer, "Progress in Nucleic Acids Research and Molecular Biology", N. E. Cohn, Ed., Academic Press, New York, 1975, vol. XV, p. 285. (e) E. F. Gale, et al in "The Molecular Basis of Antibiotic Action", Wiley-Interscience, New York, 1981, p. 345. The sequence specificity of distamycin binding presumably results from hydrogen bonding between the amide NHs of the antibiotic and the O(2) of thymines and N(3) of adenines. (a) G. Luck, M. Treibel, M. Waring, Ch. Zimmer, *Nucl. Acids Res.*, 1, 5039 (1974). (b) A. S. Zasedatelev, A. L. Zhuze, Ch. Zimmer, S. L. Grokhovsky, V. G. Gursky, B. P. Gottikh, *Dokl. Acad. Nauk. SSSR*, 231,1006 (1976). (c) A. S. Krylov, S. L. Grokkhovsky, A. S. Zasedatelev, A. L. Zhuze, G. V. Gursky, B. P. Gottikh, *Nucl. Acids. Res.* 6, 289 (1979). We chose the N-methylpyrrole tripeptide as the sequence specific DNA binding unit for the subsequent attachment of EDTA.

It has been found that DE.Fe(II) in the presence of $O_2$ and DTT efficiently cleaves DNA. Importantly, DE.Fe(II) cleaves DNA restriction fragments at highly localized sites fewer in number than bleomycin.Fe(II). The fewer number of cleavage sites can be explained by larger binding site size requirements for DE.Fe(II) compared to that of bleomycin.Fe(II) whose binding site is known to be two base pairs. Initial studies revealed that DE.Fe(II) caused several DNA strand scissions of unequal intensity clustered on each side of a binding region composed of five A+T bases.

Herein below, we described the synthesis and study of a new sequence specific DNA cleaving molecule, EDTA-distamycin(ED), which has the EDTA attached to the carboxy terminus of the tripeptide unit. We compare the relative cleavage efficiencies and base sequence specificities of ED.Fe(II) and DE.Fe(II). A comparison of the DNA cleavage patterns produced by DE.Fe(II) and ED.Fe(II) on of several restriction fragments affords new information on the binding sites and the preferred orientation on DNA of the tripeptide unit, and by extension, distamycin on DNA. Thus the EDTA attachment strategy leads to a class of "DNA affinity cleaving molecules" which allow binding sites of small molecules on heterogeneous DNA to be directly determined. The synthetic methodology used for the construction of DE and ED should be useful for future synthetic work on sequence specific DNA cleaving molecules.

EXAMPLE III

Synthesis of Distamycin EDTA:

Nitro Acid 5

The nitro acid 5 was prepared according to the procedure of Bailer, M. Bailer, B. Yagen, R. Mechoulam, *Tetrahedron,* 34, 2389 (1978), on ten times the described scale with the following modifications. N-methyl-5-nitropyrrole-2-carboxylic acid was chromatographed with petroleum ether:ether (95:5) and N-methyl-4-mitropyrrole-2-carboxylic acid was eluted with petroleum ether:ether (25:75). N-methyl-4-nitropyrrole-2-carboxyl chloride was prepared by refluxing one equivalent of N-methyl-4-nitropyrrole-2-carboxylic acid with four equivalents of thionyl chloride for 4 h, followed by removal of excess thionyl chloride under vacuum. The nitro acid 5 was obtained in 30% overall yield: IR (KBr) 1690, 1650, 1600, 1565, 1530, 1500, 1310, 1215, 1110 cm$^{-1}$; NMR (DMSO-d$_6$) $\delta$3.84 (s,3), 3.87 (s,3), 3.97 (s,3), 6.85 (s,1), 7.1 (s,1), 7.25 (s,1), 7.26 (s,1), 7.45 (s,1), 7.65 (s,1), 8.2 (s,1), 9.95 (s,1), 10.35 (s,1); UV (H$_2$O) 291 nm (35,600), 236.

EDTA-triethyl ester 9

To a solution of 10 g (0.034 mol) EDTA in 250 mL dry ethanol was added with stirring 1.5 mL of H$_2$SO$_4$. The reaction was refluxed for 24 hours and the solvent was removed. Saturated aqueous sodium bicarbonate (50 ml) was added followed by 250 mL dichloromethane. The layers were separated and the organic layer was washed three times with saturated aqueous sodium bicarbonate, two times with water, dried (Na$_2$SO$_4$), and concentrated to afford 11 g (80%) of the crude tetraethylester. The triethyl ester 9 was prepared according to the procedure of Hay and Nolan, R. W. Hay, K. B. Nolan, *J. Chem. Soc. Dalton,* 1348 (1975). To a solution of the unpurified tetraester and 4.6 g (0.027 mol) of cupric chloride dihydrate in 500 mL water was added with stirring 1.3 g (0.032 mol) f sodium hydroxide in 7 mL water at such a rate as to maintain the pH at ca. 5. The solution was then treated with H$_2$S and filtered. The filtrate was concentrated and purified by flash chromatography on silica gel with 10% methanol in dichloromethane to yield 9 g (90%) of the triethylester 9: IR(CH$_2$Cl$_2$) 3000, 1745, 1380, 1210 cm$^{-1}$; NMR (CHCl$_3$) $\delta$ 1.3 (t,9), 3.25 (m,4), 3.7 (m,8), 4.2 (m,6); m/e 376 (M+); tlc (silica gel, 10% MeOH in CH$_2$Cl$_2$)R$_f$=0.55.

EDTA-triethylester-linker 10

To a solution of 5 g (0.013 mol) EDTA-triethylester 9 and 1.52 g (0.13 mol) N-hydroxysuccinimide G. W. Anderson, J. E. Zimmerman, F. M. Callahan, *J. Am. Chem. Soc.,* 86, 1839 (1964) in 100 mL dioxane was added with stirring 2.7 g (0.013 mol) of dicyclohexylcarbodiimide in 20 mL dioxane. The solution was stirred for 12 hours, filtered and the filtrate concentrated. This residue was dissolved in 100 mL of dimethoxyethane and added with stirring to a solution of 2 g (0.02 mol) of 4-aminobutyric acid and 1.68 g (0.02 mol) of sodium bicarbonate in 100 mL water. After 12 hours the solvent was removed in vacuo and the residue purified by flash chromatography on silica gel with 10% methanol in dichloromethane to give 4 g (65%) of 10: IR (CH$_2$Cl$_2$) 3000, 1740, 1665, 1210 cm$^{-1}$; NMR (DMSO-d$_6$) 1.10 (t,9), 1.63 (m,2), 2.2 (t,2), 2.2 (t,2), 2.7 (t.2), 3.1 (m,2), 3.19 (s,2), 3.45 (s,2), 3.53 (s,4), 4.08 (m,6), 8.0 (t,1); m/e 461 (M+).

Nitro amine 6

To a solution of 2.5 g (6.0 mmol) nitro acid 5, 0.68 g (6.6 mmol) 3-dimethylaminopropylamine, and 0.89 g (6.6 mmol) N-hydroxybenzotriazole, W. Koenig, R. Geiger, *Chem. Ber.,* 103, 788 (1970), in 10 mL dimethylformamide was added with stirring at 0° C. 1.36 g (6.6 mmol) dicyclohexylcarbodiimide. The solution was stirred at 0° C. for 1 hour and 25° C. for 12 hours. The dimethylformamide was removed under high vacuum at 35° C., and the residue purified by flash chromatography on silica gel with 3% concentrated aqueous ammonia in methanol to give 2.1 g (70%) of nitro amine 6: IR(KBr) 3130, 2950, 1638, 1580, 1530, 1500, 1308, 1250 cm$^{-1}$; NMR (DMSO-d$_6$) $\delta$ 1.6 (m,2), 2.15 (s,6), 2.28 (t,2), 3.2 (m,2) 3.8 (s,3), 3.95 (s,3), 6.85 (s,1), 7.05 (s,1), 7.2 (s,1), 7.27 (s,1), 7.6 (s,1), 8.05 (t,1), 8.15 (s,1), 9.95 (s,1), 10.35 (s,1); UV (H$_2$O) 286 nm, 238; m/e 499 (M+).

Diamine 7

The nitro amine 6 was reduced to the diamine 7 with hydrogen over palladium catalyst 5% in dimethyl formamide.

Distamycin-EDTAOtriethylester 11

A solution of 1 g (2.0 mmol) of nitro amine 6 in 20 mL dimethylformamide was hydrogenated over 200 mg of 5% palladium on charcoal at atmospheric pressure for 12 hours. The mixture was filtered through Celite affording the crude amine 7. To a solution of 0.93 g (2.0 mmol) acid 10 in 25 mL dimethylformamide was added with stirring 0.36 g (2.2 mmol) of N,N'-carbonyldiimidazole in 5 mL dimethylformamide. After 2 hours, amine 7 was added and the resulting solution was stirred for 12 hours. Dimethylformamade was removed under high vacuum at 35° C. and the residue purified by flash chromatography on silica gel with 3% concentrated aqueous ammonia in methanol to yield 0.9 g (48%) 11:

IR(KBr) 2940, 1730, 1650, 1570, 1530, 1460, 1430, 1400, 1250, 1200 cm$^{-1}$; NMR (DMSO-d$_6$) δ 1.19 (t,9), 1.6 (m,2), 1.75 (m,2), 2.13 (s,6), 2.2 (t,2), 2.26 (t,2), 2.7 (m,4), 3.1 (m,2), 3.2 (m,2), 3.2 (s,2), 3.45 (s,2), 3.55 (s,4), 3.84 (s,3), 3.88 (s,3), 3.90 (s,3), 4.08 (m,6), 6.8 (s,1), 6.86 (s,1), 7.0 (s,1), 7.16 (s,1), 7.18 (s.1), 7.22 (s,1), 8.0 (t,1), 8.05 (t,1), 9.8 (t,1), 9.88 (t,1), 10.37 (s,1); UV (H$_2$O) 298 nm, 234; m/e 912 (M+).

1465, 1435, 1260, 1210, 1105 cm$^{-1}$; NMR (DMSO-d$_6$): δ 1.73 (m,2), 1.85 (m,2), 2.3 (t,2), 2.72 (s,6) 3.05 (t,2), 3.13 (m,2), 3.22 (m.2), 3.4 (t,2), 3.45 (t,2), 3.8 (s,3), 3.82 (s,3), 3.83 (s,3), 3.93 (s.4), 4.04 (s,2), 4.17 (s,2), 6.91 (s.1), 6.93 (s,1), 7.05 (s,1), 7.18 (s,1), 7.22 (s,1), 7.26 (s,1), 8.25 (t,1), 8.86 (t,1), 9.95 (s,1), 9.97 (s,1), 10.15 (s,1); UV (H$_2$O: 297 nm (35,600), 236 (29,400; m/e 866 (C$_{37}$H$_{53}$N$_{11}$O$_{11}$K+).

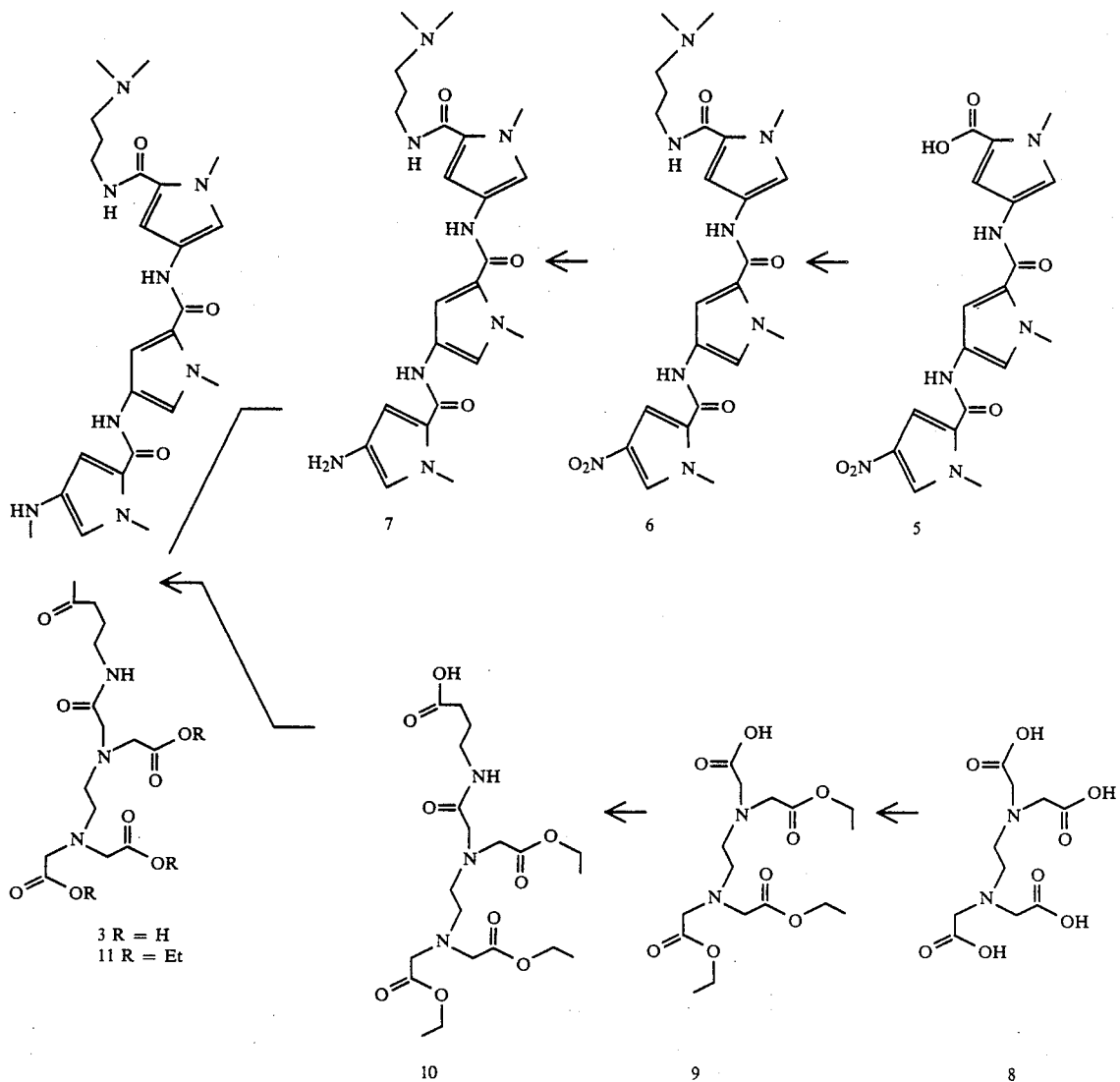

Distamycin-EDTA 3

To a solution of 0.25 g (0.37 mmol) 11 in 5 mL ethanol was added with stirring 5 mL of 0.5M aqueous lithium hydroxide. The resulting solution was stirred for 12 hours and acidified to pH 4 with 10% aqueous hydrochloric acid. The solvent was removed under vacuum at 35° C. and the residue purified by flash chromatography on silica gel with 20% concentrated aqueous ammonia in ethanol. Final purification was carried out by loading the product dissolved in water on to an Amberlite XAD-2 column and washing with 2 L of water. Elution with 0.1% HCl in methanol afforded 0.15 g (66%) 3: IR(KBr): 2960, 1730, 1640, 1565, 1550,

EXAMPLE IV

Synthesis of EDTA-Distamycin

Nitro amine 12

To a solution of 2.5 g (6.0 mmol) nitro acid 5 in 50 ml dimethylformamide was added with stirring 1.07 g (6.6 mmol) of N,N'-carbonyldiimidazole, R. Paul, G. W. Anebrison, *J. Org. Chem.*, 27, 2094 (1962), in 10 mL dimethylformamide. After 2 hours, 9.6 g (66 mmol) of 3,3'-diamino-N-methyl-dipropylamine was quickly added and the resulting solution was stirred for 12 hours. The dimethylformamide was removed under high vacuum at 35° D and the residue was triturated three times with ether. The crude product was purified by flash chromatography on silica gel with 12% concentrated aqueous ammonia in methanol to yield 2.3 g (68%) of the nitro amine 12: IR(KBr) 2960, 1640, 1580, 1530, 1311, 1210 cm$^{-1}$; NMR (DMSO-d$_6$) δ 1.46 (m,2), 1.6 (m,2), 2,12 (s,3), 2.33 (t,4), 2.55 (s,2), 3.2 (m,4), 3.80 (s,3), 3.86 (s,3), 3.96 (s,3), 6.8 (s,1), 7.04 (s,1), 7.2 (s,1) 7.27 (s,1), 7.6 (s,1), 8.05 (t,1), 8.2 (s,1), 0.94 (s,1), 10.3 (s,1); UV (H$_2$O) 294 nm, 239; m/e 542 (M+).

Nitro EDTA-triethylester 13

To a solution of 1.39 g (3.7 mmol) acid 9 in 25 mL dimethylformamide was added with stirring 0.66 g (4.07 mmol) of N,N'-carbonyldiimidazole in 5 mL dimethylformamide. After 2 hours, 2 g (3.7 mmol) of nitro-amine 12 was added and the resulting solution was stirred for 12 hours. Dimethylformamide was removed under high vacuum at 35° C. and purified by flash chromatography on silica gel with 3% concentrated aqueous ammonia in ethanol to yield 2.5 g (75%) of 13: IR(KBr) 2950, 1735, 1640, 1590, 1525, 1500, 1438, 1400, 1310, 1255, 1210; NMR (DMSO-d$_6$) δ 1.15 (t,9), 1.55 (m,2), 1.6 (m,2), 2.12 (s,3), 2.7 (m,4), 3.12 (m,2), 3.18 (s.2), 3.20 (m,2), 3.44 (s,2) 3.5 (s,4), 3.8 (s,3), 3.86 (s,3), 3.97 (s,3), 4.05 (m,6), 6.82 (s,1), 7.05 (s,1), 7.27 (s,1), 7.59 (s,1), 7.96 (t,1), 8.03 (t,1), 8.03 (t,1), 8.18 (s,1) 8.56 (s,1), 8.9 (s,1); UV (H$_2$O) 288 nm, 240; m/e 900 (M+).

EDTA-DistamycinOtriethylester 14

A solution of 1 g (1.11 mmol) 13 in 10 mL dimethylformamide was hydrogenated over 200 mg of 5% palladium on charcoal at atmospheric pressure for 12 hours. The mixture was filtered through Celite affording the crude amine 15. To a solution of 0.08 g (1.33 mmol) acetic acid in 3 mL dimethylformamide was added with stirring 0.22 g (1.33 mmol) of N,N'-carbonyldiimidazole in 3 mL dimethylformamide. After 2 hours, amine 15 was added and the resulting solution was stirred to 12 hours. Dimethylformamide was removed under high vacuum at 35° C. and the residue purified by flash chromatography on silica gel with 2% concentrated aqueous ammonia in methanol to yield 0.55 g (54%) of 14: IR(KBr) 2950, 1730, 1650, 1580, 1550, 1535, 1460, 1440, 1400, 1260, 1210 cm$^{-1}$; NMR (DMSO-d$_6$) δ 1.17 (t,9), 1.55 (m,2), 1.6 (m,2), 1.97 (s,3), 2.12 (s,3), 2.12 (s,3), 2.28 (m,4), 2.65 (m,2), 2.70 (m,2), 3.12 (m.2), 3.17 (s,2), 3.17 (s,2), 3.44 (s,2), 3.5 (s,4), 3.85 (s,3), 3.88 (s,3), 3.9 (s,3), 6.8 (s,1), 6.84 (s,1), 6.98 (s,1) 7.02 (s,1), 7.14 (s,1), 7.17 (s,1), 7.17 (s,1), 7.22 (s,1), 7.62 (s,1), 7.97 (t,1), 8.02 (t,1), 9.83 (s.1), 9.9 (s,1); UV (H$_2$O) 304 nm, 235; m/e 912 (M+).

EDTA-Distamycin 4

To a solution of 0.25 g (0.27 mmol) 14 in 5 mL ethanol was added with stirring 5 mL of 0.5M aqueous lithium hydroxide. The resulting solution was stirred for 12 hours and acidified to pH 4 with 10% aqueous hydrochloric acid. The solvent was removed under high vacuum at 35° C. and the residue purified by flash chromatography on silica gel with 3% concentrated ammonia in methanol to yield 0.17 g (75%) of the ammonium salt of ED 4: IR (KBr) 2950, 1635, 1580, 1460, 1430, 1400, 1255, 1205, 1105 cm$^{-1}$; NMR (D$_2$O) δ 1.87 *s,3), 1.9 (m,4), 2.8 (s,3), 2.9–3.13 (m,12), 3.17–3.3 (m,6), 3.53 (s,3), 3.57 (s,3), 3.6 (s,3), 3.67 (s,2), 6.42 (s,1), 6.48 (s,1), 6.56 (s,1), 6.8 (s,1), 6.83 (s,1), 6.87 (s,1), UV (H$_2$O)303 nm (35,000 est.) 235 (29,500 est.); m/e 828 (M+).

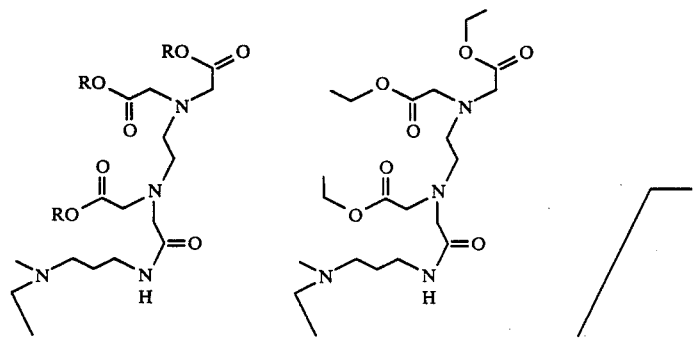

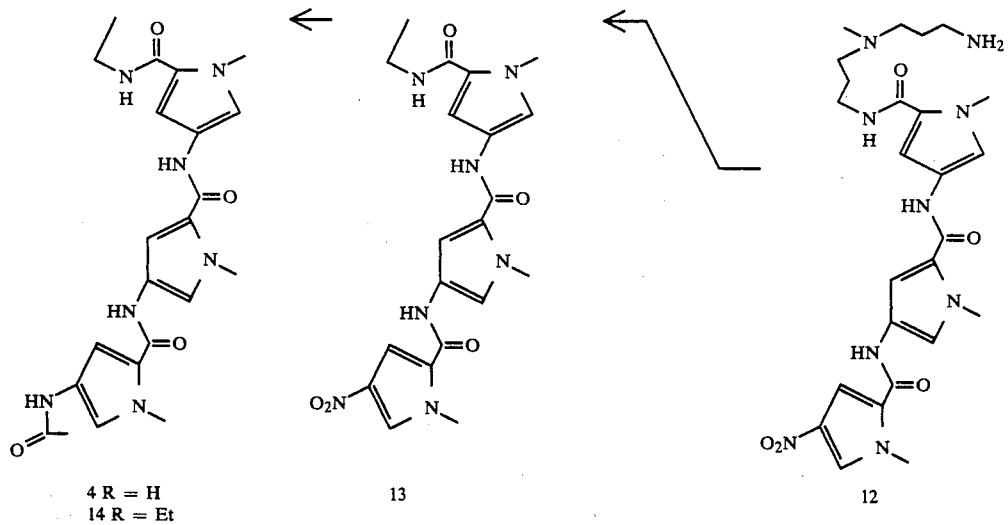

4 R = H
14 R = Et

13

12

DNA Cleavage Efficiency: DNA cleavage by DE·Fe(II) and ED·Fe(II) was followed by monitoring the conversion of supercoiled (form I) pBR322 plasmid DNA ($10^{-5}$M in base pairs) to open circular and linear forms (forms II and III, respectively). (a) J. E. Strong, S. T. Crooke, in "Bleomycin: Chemical, Biochemical, and Biological Aspects", Hecht, S. M., Ed. Springer-Verlag, New York, 1979, p. 244. (b) P. H. Johnson, L. I. Grossman, *Biochemistry*, 16, 4217 (1977). The introduction of one single strand break converts form I to form II. We find that at $10^{-6}$M concentrations DE·Fe(II) and ED·Fe(II) in the presence of $O_2$ and DTT cleave DNA, although the cleavage is less efficient than with MPE·Fe(II) or bleomycin·Fe(II) (Table IV).

TABLE IV

| Cleavage of pBR322-Plasmid in the Presence of DTT | | | | |
|---|---|---|---|---|
| | | % Form | | |
| Reagent | conc, M | I | II | III |
| EDTA.Fe (II) | $10^{-6}$ | 93 | 7 | 0 |
| DE.Fe (II) | $10^{-6}$ | 30 | 70 | 0 |
| ED.Fe (II) | $10^{-6}$ | 4 | 92 | 4 |
| MPE.Fe (II) | $10^{-7}$ | 0 | 91 | 9 |
| Bleomycin.Fe (II) | $10^{-7}$ | 0 | 48 | 52 |

Form I pBR322 ($10^{-5}$M bp), DNA cleaving reagent, buffer (10 mM Tris HCl, 50 mM NaCl, pH 7.4) and DTT (1 mM) were allowed to react at 25° D for 30 minutes and quenched. In all cases reactions were carried to completion. Forms I, II and III were analyzed by agarose gel electrophoresis and quantitated by densitometry after ethidium bromide staining.

Sequence Specific Cleavage: The sequence specific cleavage of heterogeneous double helical DNA by DE·Fe(II) and ED·Fe(II) in the presence of DTT and $O_2$ was examined on three DNA restriction fragments. These fragments (167, 279, and 381 base pairs in length) were prepared by the usual methods from bacterial plasmid pBR322 and were 3' end labeled with $^{32}$P, A. M. Maxam, W. Gilbert, *Methods Enzymol.*, 65, 499 (1980), F. Sanger and A. R. Coulson, *J. Mol. Biol.*, 94, 441–448 (1975). Each DNA cleaving reagent was allowed to react at two different concentrations with each DNA restriction fragment for 30 minutes at 25° C. The samples were frozen, lyophilized, suspended in formamide, and electrophoresed on a 0.4 mm, 9% polyacrylamide/50% urea Maxam-Gilbert sequencing gel capable of resolving DNA fragments differing in length by one nucleotide. An autoradiogram of a Maxam-Gilbert gel was prepared. The MPE·Fe(II) lanes show a uniform DNA cleavage pattern indicative of relatively non-sequence specific cleavage. In contrast, DE·Fe(II) and ED·Fe(II) both show a nonrandom pattern with DNA cleavage confined to highly localized sites. A comparison with the Maxam-Gilbert G-lane reveals the A+T rich sites cleaved by DE·Fe(II) and ED·Fe(II). Importantly, the cleavage patterns of DE·Fe(II) and ED·Fe(II) occur in similar locations but opposite intensity.

167 Restriction Fragment: The 70 bases analyzed from the autoradiogram of the Maxam-Gilbert gel for the 167 base pair restriction fragment show two cleavage sites by DE·Fe(II) and three by ED·Fe(II) (12.5M concentration formal binding density of 0.125 DE or ED/base pairs). These cleavage sites cover 2–5 contiguous base pairs separated by the sequence 3'-TTT-5' (base pairs 91–93). The cleavage sites flanking this sequence are of unequal intensity. The major cleavage site for DE·Fe(II) is on the 3' end of the 3'-TTT-5' sequence. The major cleavage site for ED·Fe(II) is on the 5' end.

279 Restriction Fragment: The 70 base pairs analyzed from the autoradiogram of the Maxam-Gilbert gel for the 279 base pair restriction fragment shows two cleavage sites by DE·Fe(II) and ED·Fe(II). The cleavage sites covering 3–5 base pairs are of unequal intensity and flank the sequence 3'-ACA-5' (base pairs 125–127). For DE·Fe(II) the major cleavage is on the 5' end of the 3'-ACA-5' sequence and for ED·Fe(II) it is on the 3' end.

381 Restriction Fragment: The 100 baes analyzed from the autoradiogram of the Maxam-Gilbert gel for the 381 base pair restriction fragment show two cleavage sites by both DE·Fe(II) and ED·Fe(II). The cleavage sites covering 3–5 base pairs are of unequal intensity and flank the sequence 3'-TTT-5' (base pairs 124–126). For DE·Fe(II), the major cleavage site is on the 3' end of the 3'-TTT-5' sequence and for ED·Fe(II) it is on the 5' end.

Opposite Strand Analysis: The 381 base pair fragment was labeled at the 5' end of the Bam HI restriction site. The cleavage patterns for DE·Fe(II) and ED·Fe(II) on this 5' end labeled 381 fragment were directly compared to the cleavage patterns labeled on the 3' end of the Bam HI site. The 70 bases analyzed from the autoradiogram of the Maxam-Gilbert gel for the 5' end labeled restriction fragment show a DNA cleavage pattern that is asymmetric, shifted to the 3' end for both DE·Fe(II) and ED·Fe(II).

Preparation of Supercoiled pBR322 and End-Labeled Restriction Fragments

DNA for this investigation was bacterial plasmid pBR322 whose entire sequence is known. J. G. Suttcliffe, *Cold Spring Harbor Symp. Quant. Biol.* 43, 77–90 (1979). The plasmid was grown in E.coli strain HB101 and isolated by the methods of Tanaka and Weissblum. T. Tanaka, B. Weisblum, *J. Bacteriol.* 121, 354–362 (1974). Superhelical pBR322 plasmids, containing 98.5% form I DNA, were first digested with the restriction endonuclease Eco RI and then labeled at the 3' end with [α-$^{32}$P]dATP and the Klenow fragment of DNA polymerase I. F. Sanger and A. R. Coulson, *J. Mol. Biol.*, 94, 441–448 (1975). A second enzymatic digest with the restriction endonuclease Rsa I yielded two end labeled fragments, 167 and 516 nucleotides in lengths. These were isolated by gel electrophoresis on a 5% polyacrylamide, 1:30 crosslinked, 2 mm thick gel. Isolation of the two fragments from the gel and subsequent procedures were similar to those of Maxam-Gilbert, A. M. Maxam, W. Gilbert, *Methods Enzymol.*, 65, 499 (1980). In a similar fashion, pBR322 was restricted with Bam HI and labeled at the 3' end. Further restriction with Eco RI and Sal I yielded a 381 and a 279 base pair fragment, respectively. The 381 base pair was 5' labeled at the Bam HI site by cleavage of pBR322 with Bam HI, treatment with bacterial alkaline phosphatase, followed by treatment with 5'(α$^{32}$P)-ATP and polynucleotide kinase. Further restriction with Eco RI yielded the desired fragment.

Cleavage Reactions

All reactions were run with freshly prepared drug-iron complexes. Equimolar drug-iron(II) complexes were made by combining aqueous drug stock solutions (~10 mM, checked spectrophotometrically before use) with a 10 mM aqueous ferrous ammonium sulfate solution and then diluting with water to the appropriate drug-iron concentration. The cleavage reactions were initiated by adding 2 µl of a buffered DNA solution (final concentrations and buffers are in figure legends) followed by 2 µl of an aqueous 10 mM DTT solution. The reactions were thoroughly mixed by vortexing, spun down and incubated at 25° C. for 30 minutes.

Analysis of the Cleavage Efficiency

The cleavage reactions were conducted with 10 µM pBR322 superhelical DNA containing >98% form I DNA. After ½ hour at 25° C. the reactions were quenched with 4 µl of a 50 mM disodium EDTA, 10% ficol solution and electrophoresed on a 1% agarose gel at 120 V for 4 hours. The gel was then stained with ethidium bromide, destained and photographed with polaroid type 55 positive-negative land film under long wavelength UV irradiation. The negative film was then scanned at 485 nm on a Cary 219 spectrophotometer and the peak areas of the form I, II and III bands were determined by a gel scanning program. The data was then corrected for the decreased stainability of form I DNA and for the presence of 1.5% form II in the original sample.

Analysis of the Sequence Specificity of the Cleavage Reactions

The cleavage reactions were run with >600 cpm of $^{32}$P 3' end labeled restriction fragments made up to a total DNA concentration of 100 µM (bp) with sonicated calf thymus DNA. The reactions were run at 25° C. for ½ hour and terminated by lyophilization and suspension in 4 l of a pH 8.3 100 mM TrisBorate, 50% formamide solution. These were then loaded on a 0.4 mm thick, 40 cm long, 8% polyacrylamide, 1:20 crosslinked, 50% urea gel and electrophoresed at 1500 V until xylene cylanol tracking dye was at the bottom of the gel. Autoradiography of the gels was carried out at −50° C. on Kodak, X-Omat AR film and the autoradiograms were then scanned at 485 nm. The relative peak area for a particular site was equated to the relative cleavage efficiency.

EXAMPLE V

Penta-N-methylpyrrolecarboxamide-EDTA (P5E) was synthesized and purified by procedures analogous to those described for distamycin-EDTA (DE) and EDTA-distamycin (ED) above. The NMR, IR, UV, and mass spectral data are consistent with the assigned structure which is as follows:

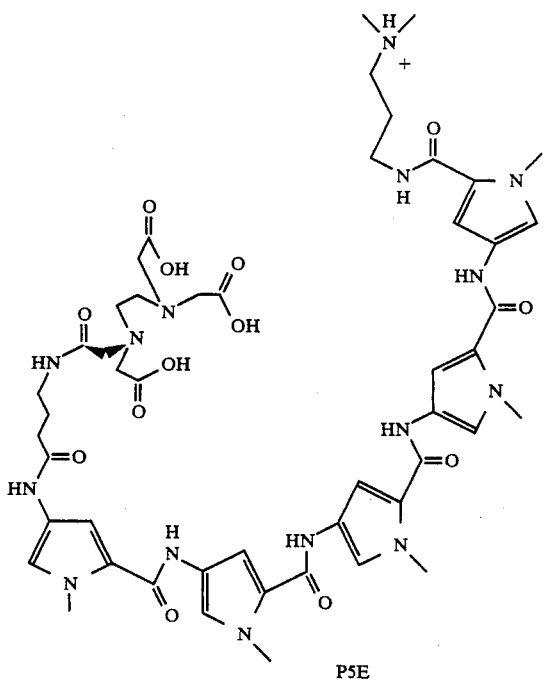

P5E

N-Methyl-4-[N-methyl-4(N-methyl-4-nitropyrrole-2-carboxamide)-pyrrole-2-carboxamide]-pyrrole-2-carboxylic acid and N-Methyl-4-[N-methyl-4(N-methyl-4-nitropyrrole-2-carboxamide)-pyrrole-2-carboxamide]-pyrrole-2-carboxamide-dimethylpropylamine, compounds 2 and 11, respectively, in the following reaction schemes were prepared as disclosed by Bailer M. et al, J. Tetrahedron (1978) Vol. 34, p. 2389 et seq.

EDTA-triethyl ester 9—To a solution of 10 g (0.034 mol) EDTA in 250 mL dry ethanol was added with stirring 1.5 mL of $H_2SO_4$. The reaction was refluxed for 24 hours and the solvent was removed. Saturated aqueous sodium bicarbonate (50 ml) was added followed by 250 mL dichloromethane. The layers were separated and the organic layer was washed three times with saturated aqueous sodium bicarbonate, two times with water, dried ($Na_2SO_4$), and concentrated to afford 11 g (80%) of the crude tetraethylester. The triethyl ester 9 was prepared as follows. To a solution of the unpurified tetraester and 4.6 g (0.027 mol) of cupric chloride dihydrate in 500 mL water was added with stirring 1.3 g (0.032 mol) of sodium hydroxide in 7 mL water at such a rate as to maintain the pH at ca. 5. The solution was then treated with $H_2S$ and filtered. The filtrate was concentrated and purified by flash chromatography on silica gel with 10% methanol in dichloromethane to yield 9 g (90%) of the triethylester 9: IR($CH_2Cl_2$) 3000, 1745, 1380, 1210 cm$^{-1}$; NMR (CHCl$_3$) δ 1.3 (t,9H, J=7 Hz)), 2.75 (s.4H), 3.3 (s,2H), 3.4 (s,4H), 3.5 (s,4H), 4.1 (q,4H,J=7 Hz); m/e 376 (M+); tlc (silica gel, 10% MeOH in $CH_2Cl_2$) $R_f=0.55$.

EDTA-triethylester-linker 5—To a solution of 5 g (0.013 mol) EDTA-triethylester 9 and 1.52 g (0.13 mol) N-hydroxysuccinimide in 100 mL dioxane was added with stirring 2.7 g (0.013 mol) of dicyclohexylcarbodiimide in 20 ml dioxane. The solution was stirred for 12 hours, filtered, and the filtrate concentrated. This residue was dissolved in 100 mL of dimethoxyethane and added with stirring to a solution of 2 g (0.02 mol) of 4-aminobutyric acid and 1.68 g (0.02 mol) of sodium bicarbonate in 100 mL water. After 12 hours the solvent was removed in vacuo and the residue purified by flash chromatography on silica gel with 10% methanol in dichloromethane to give 4 g (65%) of 5: IR ($CH_2Cl_2$) 3000, 1740, 1665, 1210 cm$^{-1}$; NMR (DMSO-d$_6$) δ 1.19 (t,9H,J=Hz) 1.63 (m,2), 2.2 (t,2H,J=6 Hz), 2.7 (t,2H,J=6 Hz), 3.1 (m,2H), 3.19 (s,2H), 3.45 (s,2H), 3.53 (s,4H), 4.08 (m,6H) 8.0 (t,1H); m/e 461 (M+).

Distamycin-EDTA-triethylester—A solution of 1 g (2.0 mmol) of nitro amine 11 in 20 mL dimethylformamide was hydrogenated over 200 mg of 5% palladium on charcoal at 52 psi hydrogen on a Parr rocker for 12 hours. The mixture was filtered through Celite and the celite was washed with 25 ml DMF affording a solution of the crude amine 3. To a solution of 0.93 g (2.0 mmol) acid 10 in 25 mL dimethylformamide was added with stirring 0.36 g (2.2 mmol) of N,N'-carbonyldiimidazole in 5 mL dimethylformamide. After 2 hours, amine 3 was added and the resulting solution was stirred for 12 hours. Dimethylformamide was removed under high vacuum at 35° C. the residue triturated three times with ether and purified by flash chromatography on silica gel with 3% concentrated aqueous ammonia in methanol to yield 0.9 g (48%) distamycin-EDTA-triethylester: IR(KBr) 2940, 1730, 1650, 1570, 1530, 1460, 1430, 1400, 1250, 1200 cm$^{-1}$; NMR (DMSO-d$_6$) δ 1.19 (t,9H,J=7 Hz), 1.6 (m,2H), 1.75 (m,2H), 2.13 (s,6H), 2.2 (t,2H,J=7 Hz), 2.26 (t,2H,J=7 Hz), 2.7 (m,4H), 3.1 (m,2H), 3.2 (m,2H), 3.2 (s,2H), 3.45 (s,2H), 3.55 (s,4H), 3.84 (s,3H) 3.88 (s,3H), 3.90 (s,3H), 4.08 (q,6H,J=Hz), 6.8 (d,1H), 6.86 (d,1H), 7.0 (d,1H), 7.16 (d,1H), 7.18 (d,1H), 7.22 (d,1H), 8.0 (t,1H), 9.8 (t,1H), 9.88 (t,1H), 10.37 (d,1H); UV ($H_2O$) 298 nm, 234; m/e 912 (M+).

Distamycin-EDTA 1—To a solution of 0.25 g (0.37 mmol) distamycin-EDTA-triethylester: in 5 mL ethanol was added with stirring 5 mL of 0.25M aqueous lithium hydroxide. The resulting solution was stirred to 12 hours and acidified to pH 4 with 10 aqueous hydrochloric acid. The solvent was removed under vacuum at 35° C., the residue triturated three times ether and purified by flash chromatography on silica gel with 20% concentrated aqueous ammonia in ethanol. Final purification was carried out by loading the product dissolved in water on to an Amberlite XAD-2 column and washing with 1 3% aqueous $Na_2EDTA$ and 2 l doubly distilled water. Elution with methanol afforded 0.15 g (66%) 1: IR(KBr): 2960, 1730, 1640, 1565, 1550, 1465, 1435, 1260, 1210, 1105 cm$^{-1}$; NMR (DMSO-d$_6$): δ 1.73 (m,2H), 1.85 (m,2H), 2.3 (t,2H,J=Hz), 2.72 (s,6H), 3.05 (t,2H,J=Hz), 3.13 (m,2H), 3.22 (m,2H), 3.4 (d,2H,J=6 Hz), 3.45 (d,2H,J=6 Hz), 3.8 (s,3H), 3.82 (s,3H), 3.83 (s,3H), 3.93 (s,4H), 4.04 (s,2H), 4.17 (s,2H), 6.91 (s,1H), 6.93 (s,1H), 7.05 (s,1H), 7.18 (s,1H), 7.22 (s,1H), 7.26 (s,1H), 8.25 (t,1H), 8.86 (t,1H), 9.95 (s,1H), 9.97 (s,1H), 10.15 (s,1H); UV ($H_2O$): 297 nm (35,600), 236 (29,400); m/e 866 ($C_{37}H_{53}N_{11}O_{11}K^+$).

Nitro amine 8—To a solution of 2.5 g (6.0 mmol) nitro acid 2 in 50 mL dimethylformaide was added with stirring 1.07 g (6.6 mmol) of N,N'-carbonyldiimidazole in 10 mL dimethylformamide. After 2 hours, 9.6 g (66 mmol) of 3,3'-diamino-N-methyl-dipropylamine was quickly added and the resulting solution was stirred for 12 hours. The dimethylformamide was removed under high vacuum at 35° C. and the residue was triturated three times with ether. The crude product was purified by flash chromatography on silica gel with 12% concentrated aqueous ammonia in methanol to yield 2.3 g (68%) of the nitro amine 8: IR(KBr) 2960, 1640, 1580, 1530, 1311, 1210 cm$^{-1}$; NMR (DMSO-d$_6$) δ 1.46 (m,2H), 1.6 (m,2H), 2.12 (s,3H), 2.33 (t,4H,J=7 Hz), 2.55 (s,2H), 3.2 (m,4H), 3.80 (s,3H), 3.86 (s,3H), 3.96 (s,3H), 6.8 (d,1H,J=1.5 Hz), 7.04 (d,1H,J=1.5 Hz), 7.2 (d,1H,J=1.5 Hz), 7.27 (d,1H,J=1.5 Hz), 7.6 (d,1H,H=1.5 Hz), 8.05 (t,1H,J=6 Hz), 8.2 (d,1H,J=1.5 Hz), 9.94 (d,1h), 10.3 (d,1h); UV (H$_2$O) 294 nm, 239; m/e 542 (M+).

Nitro EDTA-triethylester 10—To a solution of 1.39 g (3.7 mmol) acid 9 in 25 mL dimethylformamide was added with stirring 0.66 g (4.07 mmol) of N,N'-carbonyldiimidazole in 5 mL dimethylformamide. After 2 hours, 2 g (3.7 mmol) of nitroamine 8 was added and the resulting solution was stirred for 12 hours. Dimethylformamide was removed under high vacuum at 35° C. the residue triturated three times with ether and purified by flash chromatography on silica gel with 3% concentrated aqueous ammonia in ethanol to yield 2.5 g (75°) of 10: IR(KBr) 2950, 1735, 1640, 1590, 1525, 1500, 1438, 1400, 1310, 1255, 1210; NMR (DMSO-d$_6$) δ 1.15 (t,9H,J=7 Hz), 1.55 (m,2H), 1.6 (m,2H), 2.12 (s,3H), 2.7 (m,4H), 3.12 (m,2H), 3.18 (s,2H), 3.20 (m,2H), 3.44 (s,2H), 3.5 (s,4H), 3.8 (s,3H), 3.86 (s,3H), 3.97 (s,3H), 4.05 (q,6H,J=7 Hz), 6.82 (d,1H,J=1.5 Hz), 7.05 (d,1H,J=1.5 Hz), 7.19 (d,1H,J=1.5 Hz), 7.27 (d,1H,J-1.5 Hz), 7.59 (d,1H,J=1.5 Hz), 7.96 (t,1H,J-7 Hz), 8.03 (t,1H,J=7 Hz), 8.18 (d,1H,J=1.5 Hz), 8.56 (d,1), 8.9 (d,1); UV (H$_2$O) 288 nm, 240; m/e 900 (M+).

EDTA-Eistamycin-triethylester 7—A solution of 1 g (1.11 mmol) 10 in 10 mL dimethylformamide was hydrogenated over 200 mg of 5% palladium on charcoal at 52 psi hydrogen on a Parr rocker for 12 hours. The mixture was filtered through Celite and the celite was washed with 25 ml DMF to afford the crude amine which is the reduced form of compound 10. To a solution of 0.08 g (1.33 mmol) acetic acid in 3 mL dimethylformamide was added with stirring 0.22 g (1.33 mmol) of N,N'-carbonyldiimidazole in 3 mL dimethylformamide. After 2 hours, crude amine which is the reduced form of compound 10 was added and the resulting solution was stirred for 12 hours. Dimethylformamide was removed under high vacuum at 35° C., the residue triturated three times with ether and purified by flash chromatography on silica gel with 2% concentrated aqueous ammonia in methanol to yield 0.55 g (54%) of 7: IR(KBr) 2950, 1730, 1650, 1580, 1550, 1535, 1460, 1440, 1400, 1260, 1210 cm$^{-1}$; NMR (DMSO-d$_6$) δ 1.17 (t,9H,J=7 Hz), 1.55 (m,2H), 1.6 (m,2H), 1.97 (s,3H), 2.12 (s,3H), 2.28 (m,4H), 2.65 (m,2H), 2.70 (m,2H), 3.12 (m,2H), 3.17 (s,2H), 3.17 (m,2H), 3.44 (s,2H), 3.5 (s, 4H), 3.85 (s,3H), 3.88 (s,3H), 3.9 (s,3H), 4.08 (q,6H,J=7 Hz), 6.8 (d,1H), 6.84 (d,1H), 6.98 (d,1H), 7.02 (d,1H), 7.14 (d,1H), 7.17 (d,1H), 7.22 (d,1H), 7.62 (d,1H), 7.97 (t,1H,J=7 Hz), 8.02 (t,1H,J=7 Hz), 9.83 (d,1H), 9.9 (d,1H); UV (H$_2$O) 304 nm 235; m/e 912 (M+).

EDTA-Distamycin 6—To a solution of 0.25 g (0.27 mmol) 7 in 5 mL ethanol was added with stirring 5 mL of 0.25M aqueous lithium hydroxide. The resulting solution was stirred for 12 hours and acidified to pH 4 with 10 aqueous hydrochloric acid. The solvent was removed under high vacuum at 35° C. and the residue purified by flash chromatography on silica gel with 3% concentrated ammonia in methanol to yield 0.17 g (75%) of the ammonium salt of ED 6: IR (KBr) 2950, 1635, 1580, 1460, 1430, 1400, 1255, 1205, 1105 cm$^-$; NMR (D$_2$O) δ 1.87 (s,3H), 1.9 (m,4H), 2.8 (s,3H), 2.9–3.13 (m,12H), 3.17–3.3 (m,6H), 3.53 (s,3H), 3.57 (s,3H), 3.6 (s,3H), 3.67 (s,2H), 6.42 (d,1H), 6.48 (d,1H), 6.56 (d,1H), 6.8 (d,1H), 6.83 (d,1H), 6.87 (s,1H); UV (H$_2$O) 303 nm (35,000 est.) 235; m/e 828 (M+).

4-Nitro-tetra-N-methylpyrrole-carboxamide propyldimethyl amine 12—A solution of 3 g (6.0 mmol) nitro amine 11 in 25 mL dimethylformamide was hydrogenated over 400 mg of 5% palladium on charcoal at 52 psi hydrogen on a Parr rocker for 12 hours. The mixture was filtered through Celite and the celite was washed with 20 ml dimethylformamide to afford the crude amine. 200 mL of water and 0.6 g (7.2 mmol) NaHCO$_3$ were added with stirring to the filtrate, followed by a solution of 1.35 g (7.2 mmol) N-methyl-4-nitropyrrole-2-carbosylic acid chloride in 10 mL dimethylformamide. The mixture was stirred 12 hours, 200 mL water added and filtered. The product was washed with saturated aqueous sodium bicarbonate, water and dried to afford 2.6 g (70%) of the nitro amine 12: IR (KBr) 2950, 1630, 1580, 1530, 1465, 1430, 1308, 1255 cm$^{-1}$; NMR (DMSO-d$_6$) δ 1.6 (m,2H), 2.2 (s,6H), 2.3 (t,2H,J=7 Hz), 3.2 (m,2H), 3.8 (s,3H), 3.85 (s,3H), 3.88 (s,3H), 3.95 (s,3H), 6.85 (s,1H), 7.07 (m,2H), 7.2 (s,1H), 7.27 (s,1H), 7.31 (s,1H), 8.05 (t,1H,J=7 Hz), 8.1 (s,1H), 9.92 (s,1H), 9.97 (s,1H), 10.03 (s,1H), 10.35 (s,1H), UV (H$_2$O) 305 nm, 236; m/e 621 (M+).

4-Nitro-penta-N-methylpyrrole-carboxamide propyldimethyl amine 13—A solution of 2.6 g (4.2 mmol) nitro-tetrapyrrole amine 12 in 40 mL dimethylformamide was hydrogenated over 400 mg of 5% palladium on charcoal at 52 psi hydrogen on a Parr rocker for 12 hours. The mixture was filtered through Celite and the celite was washed with 10 ml DMF to afford the crude amine. 200 mL of water and 0.42 g (5.0 mmol) NaHCO$_3$ were added stirring to the filtrate, followed by a solution of 0.95 g (5.0 mmol) N-methyl-4-nitropyrrole-2-carboxylic acid chloride in 7 mL dimethylformamide. The mixture was stirred for 12 hours and the solvent removed under high vacuum at 35° C. The residue was triturated three times with ether and purified by chromatography on silica gel with 2% concentrated aqueous ammonia (33%) in methanol yielding 1.9 g (61%) of nitro aminde 13: IR (KBr) 3350, 2945, 1627, 1580, 1530, 1465, 1435, 1307, 1260, 1110 cm$^{-1}$; NMR (DMSO-d$_6$) δ 1.65 (m,2H), 2.2 (s,6H), 2.3 (t,2H=J=7 Hz), 3.2 (m,2H), 3.83 (s,3H), 3.9 (s,3H), 3.91 (s,3H), 4.0 (s,3H), 6.85 (s,1H), 7.1 (m,3H), 7.2 (m,3H), 7.27 (m,2H), 7.31 (s,1H), 8.1 (t,1H,J=7 Hz), 8.2 (s,1H), 9.92 (s,1H), 9.97 (s,1H), 10.03 (s,1H), 10.35 (s,1H); UV (H$_2$O) 310 nm, 236; m/e 743 (M+).

Penta-N-methylpyrrole-carboxamide-EDTA triethyl ester 16—A solution of 1 g (1.35 mmol) nitro amine 13 in 20 mL dimethylformamide was hydrogenated over 200 mg of 5% palladium on charcoal at atmospheric pressure for 24 hours. The mixture was filtered through Celite and the celite was washed with 25 ml DMF to afford the crude amine.

To a solution of 0.62 g (1.35 mmol) triethylester 5 in 10 ml dimethylformamide was added with stirring 0.24 g (1.5 mmol) of N,N'-carbonyldiimidazole in 5 mL dimethylformamide. After 2 hours, the reduced nitro compound was added and the resulting solution was stirred for 12 hours. Dimethylformamide was removed under high vacuum at 35° C., the residue was triturated three times with ether and purified by flash chromatography on silica gel with 4% concentrated aqueous ammonia (33%) in ethanol to afford 0.6 g (40%) of P5E ethyl ester 16: IR (KBr) 2960, 1725, 1650, 1585, 1540, 1470, 1440, 1410, 1260, 1210, 1110 cm$^{-1}$; NMR (DMSO-d$_6$) δ 1.2 (t,6H,J=7 Hz), 1.65 (m,2H), 1.74 (m,2H), 2.15 (s,6H), 2.2 (m,2H), 2.3 (t,2H,J=7 Hz), 2.7 (m,4H), 3.1 (m,2H), 3.2 (m,2H), 3.22 (s,2H), 3.45 (s,2H), 3.50 (s,4H), 3.8 (s,3H), 3.87 (m,12H), 4.07 (m,6H), 6.8 (s,2H), 7.07 (m,3H), 7.2 (s,2H), 7.25 (s,3H), 8.1 (t,1H,H=7 Hz) 9.9 (s,1H) 9.95 (s,1H) UV (H$_2$O) 306 nm, 236; m/e 1156 (M+).

Penta-N-methylpyrrole carboxamide-EDTA 15—To a solution of 250 mg (0.23 mmol) P5E triethyl ester 16 in 5 mL ethanol was added with stirring 5 mL of 0.25M aqueous lithium hydroxide. The resulting solution was stirred for 12 hours and acidified to pH 4 with 10% aqueous hydrochloric acid. The solvent was removed under high vacuum at 35° C. and the residue purified by flash chromatography on silica gel with 4% concentrated aqueous ammonia (33%) in methanol. Final purification was carried out by loading the product dissolved in water, onto an amberlite XAD-2 column and washing with 1 l of 3% aqueous Na$_2$EDTA and 2 L of water. Elution with methanol afforded 0.17 (73%) P5E 15: IR (KBr) 2950, 1730, 1640, 1570, 1460, 1438, 1430, 1400, 1252, 1205 cm$^{-1}$; NMR (DMSO-d$_6$) 1.77 (m,2H), 1.92 (m,2H), 2.33 (t,2H,J=7 Hz), 2.75 (s,6H), 3.08 (m,2H), 3.24 (m,2H), 3.3 (m,2H), 3.35 (m,2h), 3.8 (s,3H), 3.87 (m,12H), 3.98 (s,2H), 4.1 (s,2H), 6.95 (m,2H), 7.1 (m,3H), 7.2 (s,1H, 7.22 (s,1H), 7.32 (s,3H), 8.2 (s,1H), 8.65 (s,1H), 9.97 (m,4H), 10.05 (s,1H); UV (H$_2$O) 310 nm (45,000)[101] 238 nm; m/e 1072 (M+).

Penta-N-methylpyrrole-propyldimethyl amine P5 14—A solution of 250 mg (0.35 mmol) nitro-penta-N-methylpyrrolepropyl dimethyl amine 13 in 20 mL dimethylformamide was hydrogenated over 100 mg of 5% palladium on charcoal at 52 psi hydrogen on a Parr rocker for 12 hours. The mixture was filtered through celite yielding the crude amine. The celite was washed with 10 ml DMF.

To a solution of 0.024 g (0.40 mmol) acetic acid in 3 mL dimethylformamide was added with stirring 0.065 g (0.40 mmol) of N,N'-carbonyldiimidazole in 2 mL dimethylformamide. After 2 hours, the crude amine was added and the resulting solution was stirred for 12 hours. Dimethylformamide was removed under high vacuum at 35° C., the residue was triturated three times with ether and purified by flash chromatography on silica gel with 5% concentrated aqueous ammonia (33%) in ethanol to yield 150 mg (60%) of P514: IR (KBr) 2940, 1640, 1580, 1530, 1460, 1430, 1400, 1255, 1200, 1100 cm$^{-1}$; NMR (DMSO-d$_6$) δ 1.65 (m,2H), 2.0 (s,3H), 2.2 (s,6H), 2.3 (t,2H,J=7 Hz), 3.2 (m,2H), 3.83 (s,3H), 3.9 (m,12H), 6.85 (s,1H) 6.0 (s,1H), 7.07 (m,3H), 7.15 (s,1H), 7.18 (s,1H), 7.25 (s,3H), 8.10 (t,1H,J=6 Hz), 9.85 (s,1H), 9.91 (m,2H), 9.97 (s,2H); UV (H$_2$O) 312 nm, (45,000)[101] 236 nm: m/e 755 (M+).

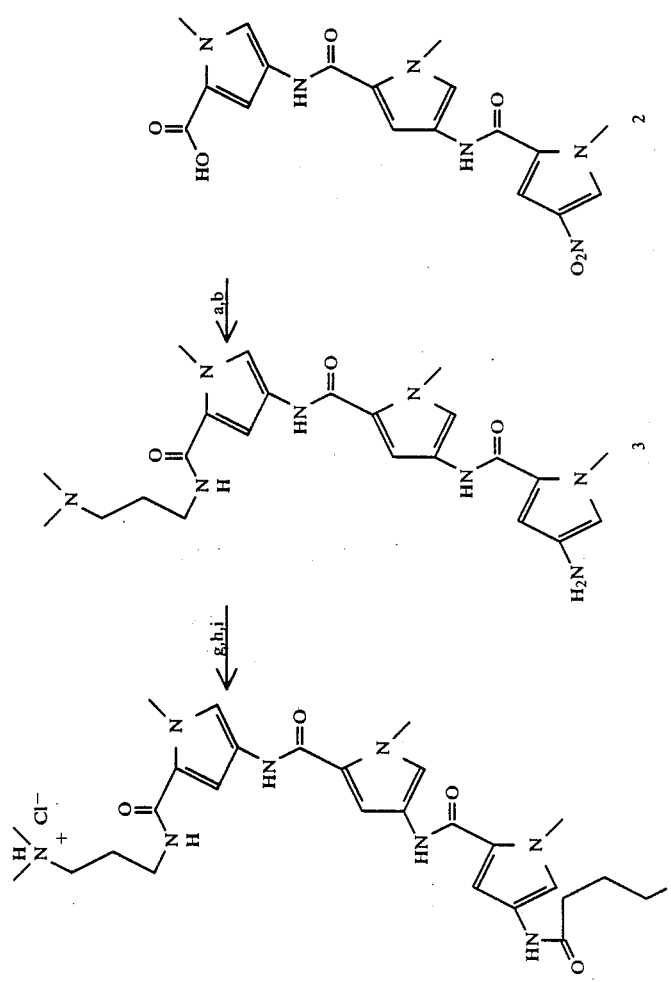

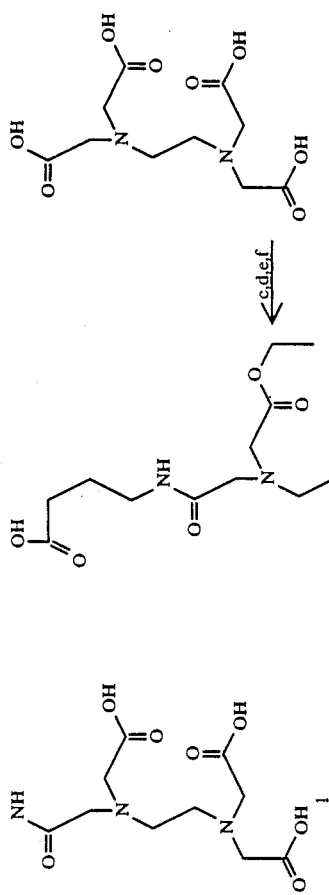
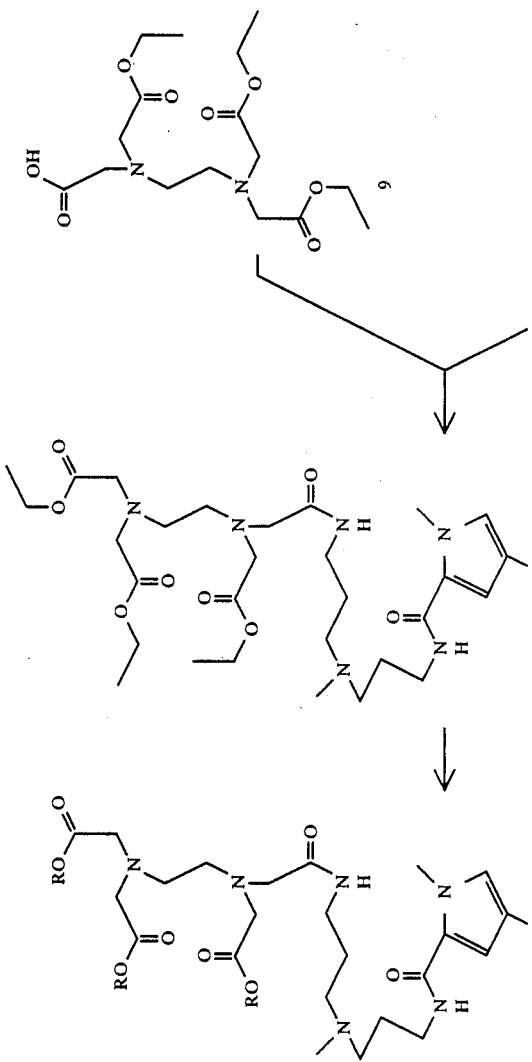
a. H₂N(CH₂)₃N(CH₃)₂, HOBt, DCC
b. H₂, Pd/C
c. H₂SO₄, EtOH
d. CuCl₂, NaOH
e. DCC, NHS
f. H₂N(CH₂)₃CO₂H, NaHCO₃
g. CDI
h. LiOH
i. HCl

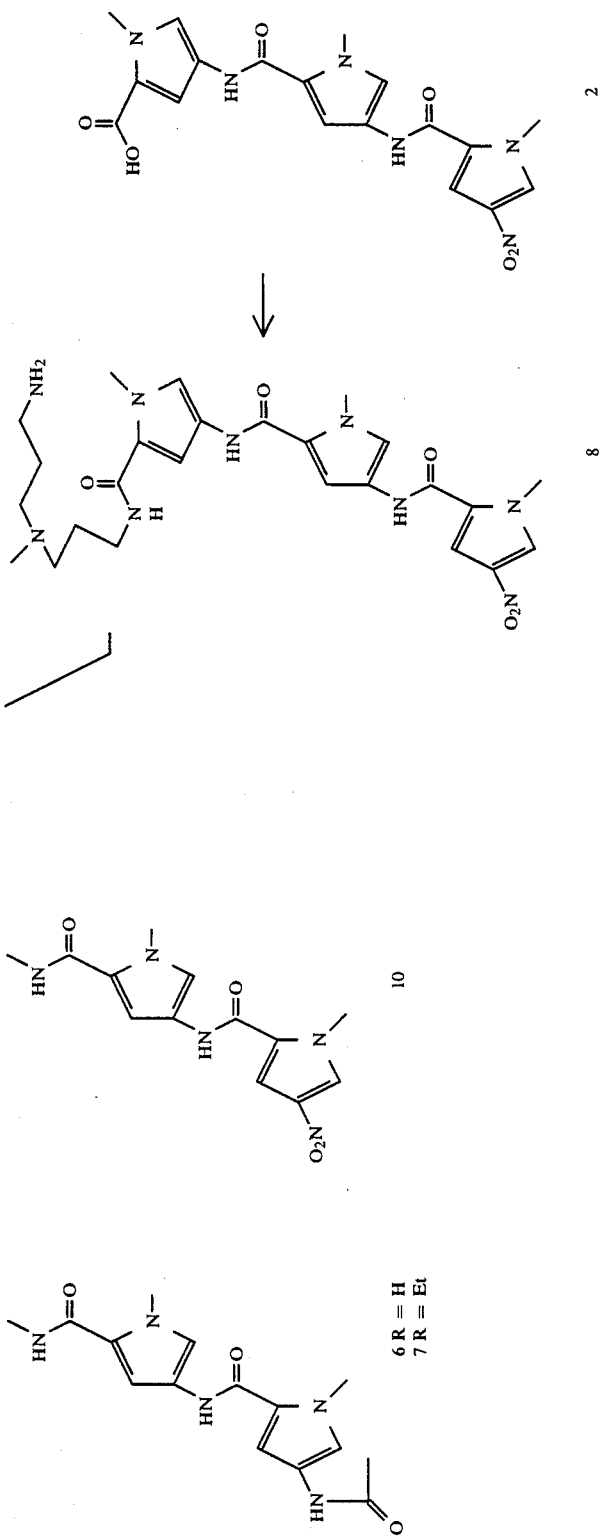

-continued
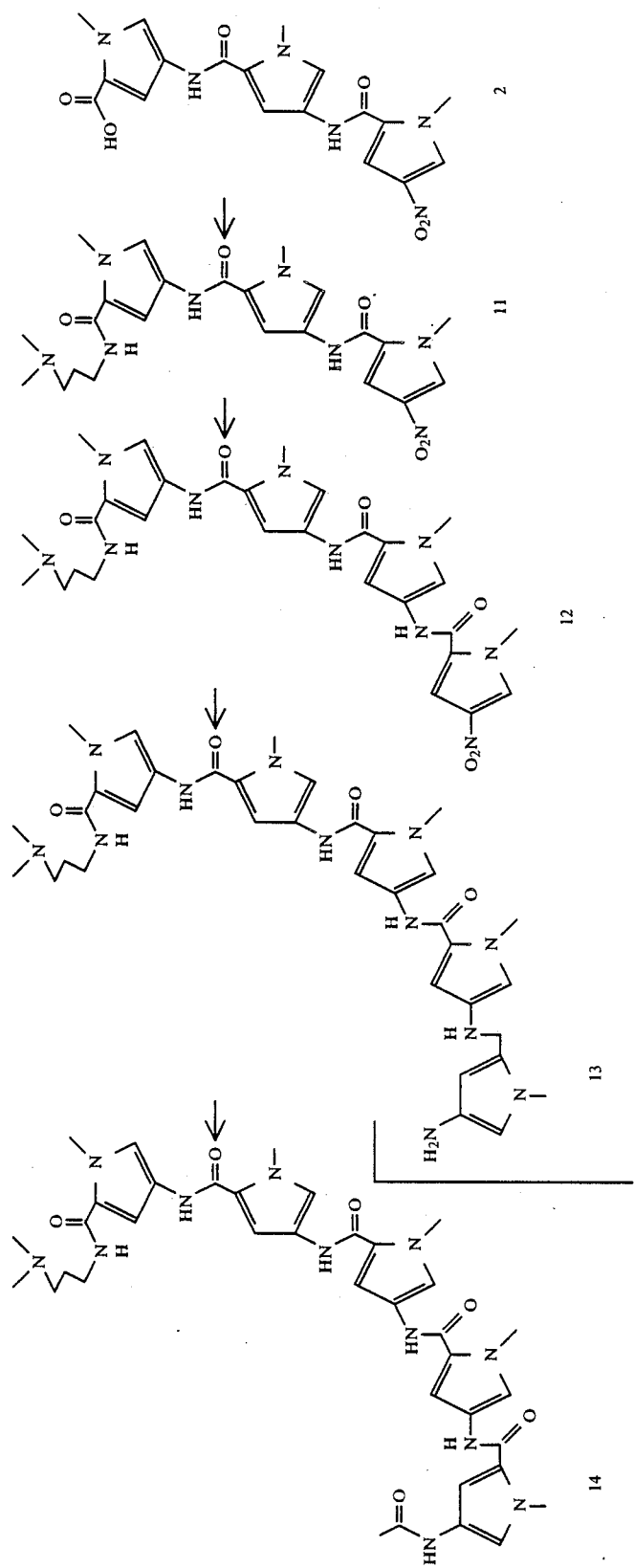

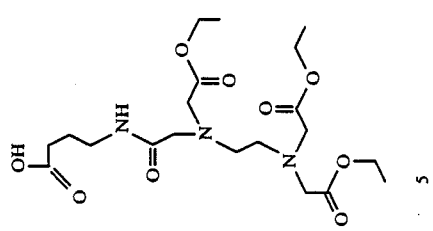
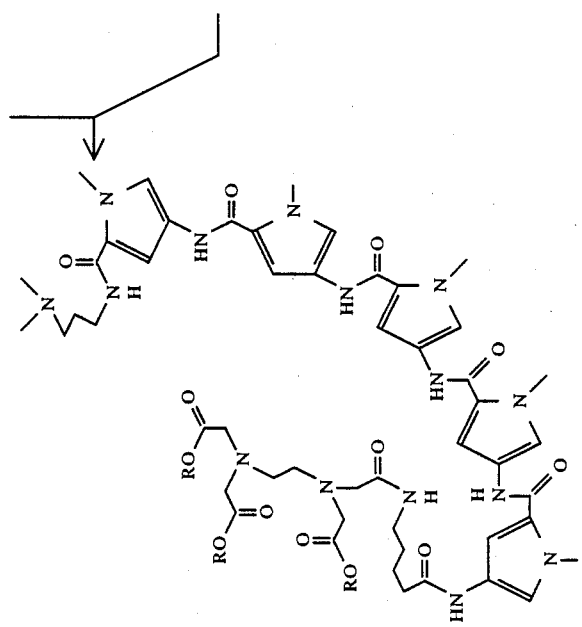

Fe(NH$_4$)$_2$(SO$_4$)$_2$.6H$_2$O was obtained from Baker and DTT from Calbiochem. Aqueous 5'-($\alpha^{32}$p)dATP triethylammonium salt, 3000 Ci/mmole, was from Amersham and aqueous 3'-($\gamma^{32}$p)dATP, 5000–9000 Ci/mmole, was from ICN. Nucleotide triphosphates were from Boehringer Mannheim. All enzymes were from New England Biolabs except bacterial alkaline phosphatase and T4 polynucleotide knase which were from BRL. Solutions of Fe(NH$_4$)$_2$(SO$_4$)$_2$, DTT and P5E were prepared freshly. P5E was characterized spectroscopically before use. DE and P5E were mixed immediately before use with Fe(II) at 1 mM concentrations and diluted approximately to yield P5E.Fe(II). DNA for this investigation was isolated from the bacterial plasmid pBR322 whose entire sequence is known, Sutcliffe, J. G. (1979) *Cold Spring Harbor Symp. Quant. Biol.*, 43, 77. Milligram quantities of the plasmid were grown in Escherichia coli, strain HB 101, and isolated by procedures similar to those of Tanaka and Weisblum. Calf thymus DNA (Sigma was sonicated, deproteinized and extensively dialyzed.

Cleavage Efficiency Assay

Each DNA cleaving reagent (DE.Fe(II) and P5E.Fe(II)) was allowed to equilibrate for 1 hour at 37° with supercoiled (form I) pBR322 DNA (10 µM in base pairs) in a buffer containing 40 mM Tris base and 5 mM NaOAc at pH 7.9. The reaction was initiated by adding an aqueous solution of DTT (5 mM final concentration). Final concentrations are given in Table V. The cleavage reactions were allowed to run to completion (1:5 hours, 25°), quenched with 4 µl of a 50 mM Na$_2$EDTA, 10% ficol solution and electrophoresed on a 1% agarose gel at 120 V for 4 hours. Forms I, II, and III were analyzed by ethidium bromide staining, quantitated by densitometry and corrected for decreased stainability of form I DNA and for the presence of 1.5% form II in the original sample.

Double Strand Cleavage Assay

Linear pBR 322 plasmid DNA was obtained by digestion of superhelical plasmids with the restriction endonuclease Eco RI, followed by ethanol precipitation. P5E.Fe(II)/DTT reactions were carried out as described above. The final concentrations were: 0.5 µM P5E.Fe(II); 5 mM DTT; and 50 µM DNA. Reactions were analyzed by 1% agarose gel electrophoresis and ethidium bromide staining. The approximate P5E.Fe(II) cleavage sites were located by digestion of pBR 322 with several restriction enzymes followed by P5E.Fe(II) (0.5 µM) cleavage. Changes in the lengths of the resulting DNA fragments could be correlated with cleavage sites. Mapping restriction enzymes used were Eco RI, Sal I, Nde I, Ava I, Hind II+Ava I, Taq I, and Rsa I.

Preparation of Specific Labeled DNA Fragments

Superhelical pBR 322 plasmid DNA was digested with the restriction endonuclease Eco RI and then labeled at the 3' end with ($\alpha^{-32}$P)dATP using the Klenow fragment of DNA polymerase I. A second enzymatic digest with the restriction endonuclease Rsa I yielded two end labeled fragments, 167 and 517 nucleotides in length. These were isolated by gel electrophoresis on a 5% polyacrylamide, 1:30 crosslinked, 2 mm thick gel. Isolation of the two fragments from the gel and subsequent procedures were similar to those of Maxam and Gilbert. Cleavage of pBR 322 with Eco RI, and successive treatment with bacterial alkaline phosphatase, ($\gamma^{-32}$P)ATP and T4 polynucleotide knase, followed by restriction with Rsa I yielded the 517 and 167 bp DNA fragments labeled with $^{32}$P at the 5' end.

High Resolution Denaturing Gel

The cleavage reactions were run as described above with >600 cpm of $^{32}$P end labeled restriction fragments made up to a total DNA concentration of 100 µM (bp) with sonicated calf thymus DNA. Final concentrations are: 1.2 µM P5E.Fe(II) and 1 mM DTT. The reactions were run at 25° for 1 hour, terminated by freezing ($-78°$ C.), lyophilized and suspended in 4 µl of a pH 8.3 100 mM Tris-Borate, 50% formamide solution. These samples were heat denatured and loaded on a 0.4 mm thick, 40 cm long, 8% polyacrylamide, 1:20 crosslinked, 50% urea gel and electrophoresed at 1500 V. Autoradiography of the gels was carried out at $-50°$ on Kodak, X-Omat Ar film and the autoradiograms were scanned at 485 nm on a Cary 219 spectrophotometer. The relative peak area for each site was equated to the relative cleavage efficiency.

RESULTS

Cleavage Efficiency

The DNA cleavage efficiency of P5E.Fe(II) was followed by monitoring the conversion of supercoiled pBR 322 plasmid DNA (form I) to open circular (form II) and linear forms (form III). Unlike DE.Fe(II), P5E.Fe(II) requires equilibration (37°, 1 hour) with the DNA before initiation of cleavage with DTT for optimum efficiency. In the presence of O$_2$ and DTT (5 mM), P5E.Fe(II) at 0.01 µM concentration cleaves DNA (10 µM base pairs) almost two orders of magnitude more efficiently than distamycin-EDTA.Fe(II) (DE.Fe(II)). Importantly, P5E.Fe(II) at 0.01 µM concentration in the presence of 5 mM DTT cleaves form I pBR 322 DNA at 0.22 µM plasmid (1 mM bp) to 40% form II DNA. (Table V). Assuming the conversion of form I to form II represents a minimum of one strand scission, this result corresponds to a minimum of nine single strand cleavage events per P5E.Fe(II) molecule.

TABLE V

Cleavage of pBR 322 Plasmid DNA (10 µM bp) in the Presence of 5 mM DDT[a,b]

| Reagent | conc, M | Form % I | II | III |
|---|---|---|---|---|
| EDTA.Fe (II) | $10^{-6}$ | 96 | 4 | 0 |
| DE.Fe (II) | $10^{-6}$ | 32 | 68 | 0 |
| P5E.Fe (II) | $10^{-6}$ | 3 | 59 | 38 |
| P5E.Fe (II) | $10^{-7}$ | 48 | 47 | 5 |
| P5E.Fe (II)[c] | $10^{-7}$ | 60 | 40 | 0 |

[a]All reactions were run to completion.
[b]P5E was preequilibrated at 37° for 1 hour.
[c]DNA at 1 mM bp.

Double Strand Cleavage

The sequence specific double strand cleavage of DNA by P5E.Fe(II)/DTT was examined on linear pBR 322 plasmid DNA, 4362 base pairs in length, obtained by cleavage of supercoiled pBR 322 plasmid with Eco RI. P5E.Fe(II) (0.5 to 1.0 μM) was allowed to equilibrate at 37° for 1 hour with the linear plasmid DNA (50 μM) followed by addition of DTT (5 mM) to initiate reaction. After 1 hour the reaction mixture was analyzed by agarose gel electrophoresis. The major observarion is that P5E.Fe(II) (P5E/bp=0.01) cleaves linear pBR 322 DNA into discrete DNA fragments. Restriction mapping indicates major double strand cleavage sites are centered at approximately 4.3, 4.2, 3.3 and 3.2 kilobases (kb) with minor sites at 2.6, 2.4, 2.0 and 1.8 kb. At higher P5E concentrations ($\geq 1.0$ μM) the specificity of the cleavage reaction is diminished.

DNA Cleavage Pattern Analyses

The cleavage sites of P5E.Fe(II) can be resolved in greater detail by analysis of the DNA cleavage patterns using $^{32}P$ end labeled restriction fragments and high resolution denaturing gel electrophoresis. A 517 base pair Rsa I-Eco RI restriction fragment from pBR 322, nucleotides 3848–4362, containing two major P5E.-Fe(II) cleavage sites (4.3 and 4.2 kb) was chosen for study. The Eco RI site was labeled separately with $^{32}P$ on the 5' and 3' ends. The resulting DNA fragments were allowed to react with P5E.Fe(II) (P5E/base pair=0.012) for 1 hour, then stopped by freezing, lyophilized and suspended in formamide buffer. The $^{32}P$ end labeled DNA cleavage products were analyzed by Maxam-Gilbert sequencing gel methods. A histogram of the DNA cleavage patterns obtained from densitometric analysis of the autoradiogram reveals major cleavage sites covering 3–5 base pairs contiguous to a six base pair region of A+T rich DNA (base pairs 4323–4324). The cleavage sites flanking this region are of unequal intensity with major cleavage on the adenine side of a six base pair 5'-TTTTTA-3' sequence. Minor cleavage sites flank the sequence 5'-TAATAAT-3', located at base pairs 4300–4306. The cleavage patterns produced on opposite strands are asymmetric, shifted to the 3' side of each DNA strand.

EXAMPLE VI

Bis(EDTA distamycin) and EDTA-(bisdistamycin) were prepared as follows:

Bisdistamycin 19—A solution of 0.25 g (0.5 mmol) nitro amine 2 in 10 mL dimethylformamide was hydrogenated over 2000 mg of 5% palladium on charcoal at 50 psi hydrogen on a Parr rocker for 12 hours. The mixture was filtered through Celite affording the crude amine 3. The celite was washed with 10 ml DMF. To this solution was added with stirring 0.09 g (0.28 mmol) of di-N-hydroxysuccinimide-heptane dicarbosylic acid which was prepared as follows. To a solution of 5t (31.0 mmol) pimelic acid and 7.9 g (68 mmol) N-hydroxysuccinimide was added with stirring 14 g (68 mmol) of dicyclohexylcarbodiimide in 20 ml dioxane. The solution was stirred for 12 hours, filtered, concentrated and chromatographed on silica gel with 25% ethyl acetate in dichloromethane.

After 12 hours DMF was removed from the bisdistamycin under high vacuum at 35° C., the residue was triturated three times with ether and purified by flash chromatography on silica gel with 5% concentrated aqueous ammonia (33%) in methanol affording 0.30 g (70%) BD: IR (KBr) 3280, 2940, 1640, 1580, 1530, 1460, 1430, 1400, 1250, 1200 cm$^{-1}$; NMR (DMSO-d$_6$) δ 1.3 (m,2H), 1.5 (m,8H), 2.1 (s,12H), 2.2 (m,8H), 3.15 (m,4H), 3.8 (s,3H), 3.85 (s,3H), 3.77 (s,3H), 6.8 (d,2H,J=1.65 Hz), 6.85 (d,2H,J=1.5 Hz), 7.04 (d,2H,J=1.5 Hz), 7.15 (m,4H), 7.25 (d,2H,J=1.5 Hz), 8.05 (t,2H,J=6 Hz), 9.8 (s,2H), 9.9 (s,4H), UV (EtOH) 305 nm (70,000)$^{103}$ 230 nm, m/e 1061 (M+).

Bis(EDTA-triethylester distamycin BED.Et$_3$—A solution of 0.25 g (0.23 mmol) nitro-EDTA triethylester 10 in 10 ml DMF was hydrogenated over 200 mg of 5% Pd/C at 50 psi hydrogen on a Parr rocker for 12 hours. The mixture was filtered through celite and the celite was washed with 10 ml DMF. To this solution was added with stirring 0.041 g (0.1 mmol) di-N-hydroxysuccinimide heptane dicarboxylic acid. After 12 hours, DMF was removed under high vacuum at 35° C., the residue was triturated three times with ether and purified by flash chromatography on silica gel with 35% concentrated aqueous ammonia in methanol to yield 0.2 g (80%) BED.Et$_3$31: IR (KBr) 3290, 2940, 1735, 1660, 1640, 1580, 1530, 1460, 1430, 1255, 1200 cm$^{-1}$; NMR (DMSO-d$_6$) δ 1.18 (t,18H,J=8 Hz), 1.3 (m,2H), 1.6 (m,12H), 2.13 (s,6H), 2.25 (t,4H,J=7 Hz), 2.3 (m,8H), 2.68 (m,4H), 2.73 (m,4H), 3.13 (m,4H), 3.18 (m,4H), 3.2 (m,4H), 3.5 (m,4H), 3.59 (m,8H), 3.8 (s,6H), 3.86 (s,6H), 3.97 (s,6H), 4.05 (m,12H), 6.82 (d,2H,J=1.5 Hz), 6.86 (d,2H,J=1.5 Hz), 7.05 (d,2H,J=1.5 Hz), 7.18 (d,2H,J=1.5 Hz), 7.20 (d,2H,J=1.5 Hz), 7.23 (d,2H,H=1.5 Hz), 7.96 (s,2), 8.02 (s,2H), 9.77 (s,2H), 9.88 (s,2H), 10.0 (s,2H); UV (H$_2$O) 306 nm, 235; m/e 1864 (M+).

Bis(EDTA-distamycin) BED 17—To a solution of 0.25 g (0.14 mmol) BED.Et$_3$ in 5 mL ethanol was added with stirring 5 mL of 0.25M aqueous lithium hydroxide. The resulting solution was stirred for 12 hours and acidified to pH4 with 10% aqueous hydrochloric acid. The solvent was removed under high vacuum at 35° C., the residue was triturated three times with ether and purified by flash chromatography on silica gel with 5% concentrated aqueous ammonia (33%) in methanol. Final purification was carried out by loading the product dissolved in water onto an amberlite XAD-2 column and washing with 1 1 3% aqueous Na$_2$EDTA and 2 1 doubly distilled water. Elution with methanol afforded 0.15 g (62%) BED 17; IR (KBr): 3300, 2940, 1740, 1660, 1640, 1570, 1540, 1470, 1440, 1410, 1260 cm$^{-1}$; NMR (DMSO-d$_6$): 1.25 (m,2H), 1.65 (m,4H), 1.9 (m,8H), 2.3 (t,4H,J=7 Hz), 2.7 (s,6H), 3.1 (m,8H), 3.25 (m,4H), 3.3 (m,4H), 3.4 (m,4H), 3.45 (m,4H), 3.8 (3s,18H), 3.94 (s,8H), 4.0 (s,4H), 4.1 (s,4H), 6.9 (s,4H), 7.0 (d,2H,J=1.5 Hz), 7.17 (d,2H,J=1.5 Hz), 7.20 (d,2H,J=1.5 Hz), 7.23 (d,2H,J=1.5 Hz), 8.2 (s,2H), 8.83

(s,2H), 9.95 (3s,6H); UV (H$_2$O) 306 (70,000)$^{103}$ 235 nm; m/e 1696 (M+).

Dimethylamino tri-N-methylpyrrole heptanoic acid 21—A solution of 0.5 g (1 mmol) nitro amine 2 in 10 ml dimethylformamide was hydrogenated over 200 mg pd/C at 50 psi hydrogen on a Parr rocker for 12 hours. The mixture was filtered through celite and the celite was washed with 10 ml DMF. The combined solution was added with stirring to 2 mmol heptane dicarboxylic acid monoimidazolide in 10 ml DMF. Heptane dicarboxylic acid monoimidazolide was synthesized by adding with stirring 0.4 g (2 mmol) acyldiimidazole to 1.6 g (10 mmol) heptane dicarboxylic acid in 10 ml DMF and stirring an additional 1 hour. After 12 hours, 10 ml H$_2$O was added to the reaction mixture, solvent was removed under vacuum at 35° C., the residue was triturated three times with ether and purified by flash chromatography on silica gel with 2% concentrated aqueous ammonica in methanol to afford 0.5 g (5%) amino acid 21; IR (KBr) 3300, 2950, 1660, 1640, 1570, 1530, 1460, 1430, 1400, 1260, 1200 cm$^{-1}$; NMR (DMSO-d$_6$) δ 1.3 (m,2H), 1.4–1.6 (m,3H), 2.15 (s,6H), 2.25 (m,6H), 3.2 (m,2H), 3.75 (s,3H), 3.8 (s,3H), 3.83 (s,3H), 6.85 (d,1H,J=1.5 Hz), 6.90 (d,1H,J=1.5 Hz), 7.05 (d,1H,J=1.5 Hz), 7.15 (m,2H), 7.2 (d,1H,J=1.5 Hz), 8.1 (t,1H,J=6 Hz), 9.8 (s,1H), 9.9 (s,1H), 9.93) (s,1H); UV (H$_2$O) 302 nm, 238 nm; m/e 611 (M+).

EDTA bisdistamycin triethylester E(Et$_3$)BD—0.37 g (0.41 mmol) nitro EDTA triester 10 in 15 ml DMF was hydrogenated over 200 mg Pd/C at 50 psi hydrogen on a Parr rocker for 12 hours. This solution was filtered through celite and the celite was washed with 10 ml DFM to afford the crude amine. To 0.25 g (0.41 mmol) amino acid 21 in 15 ml dimethylformamide was added with stirring 0.09 g (0.49 mmol) acyldiimidazole. After 1 hour the crude amine solution was added to the imidazolide with stirring and the resulting solution stirred for 12 hours at 25° C. The DMF was removed under vacuum at 35° C., the resulting residue triturated three times with ether and purified by flash chromatography on silica gel with 4.5% concentrated aqueous ammonia in methanol to afford 0.45 g (73%) EBD triethyl ester: IR (KBr) 3290, 2950, 1740, 1670, 1640, 1590, 1560, 1470, 1440, 1410, 1260, 1210 cm$^{-1}$; NMR (DMSO-d$_6$) δ 1.2 (t,9H,J=7 Hz), 1.3 (m,2H), 1.6 (m,10H), 2.15 (s,9H), 2.3 (t,4H,J=7 Hz), 2.35 (m,6H), 2.7 (m,4H), 3.15 (m,2H), 3.2 (m,6H), 3.5 (s,4H), 4.6 (s,2H), 3.85 (s,m3H), 3.9 (s,3H), 3.92 (s,3H), 6.85 (s,1H), 6.87 (s,1H), 6.9 (s,2H) 7.06 (s,2H), 7.15 (s,2H), 7.17 (s,2H), 7.23 (s,2H), 7.95 (t,1H,J=7 Hz), 8.0 (t,1H,J=7 Hz), 8.05 (t,1H,J=7 Hz), 9.85 (s,2H), 9.95 (s,2H), 9.96 (s,2H); UV (EtOH) 303 nm, 235 nm; m/e 1463 (M+).

EDTA—bis distamycin—EBD 18—To a solution of 0.2 g (0.14 mmol) triester 33 in 5 ml ethanol was added with stirring 5 ml of 0.25M aqueous lithium hydroxide. The resulting solution was stirred for 12 hours and acidified to pH 4 with 10% hydrochloric acid. The solvent was removed under high vacuum at 35° C. and the residue purified by flash chromatography on silica gel with 5% concentrated ammonia hydroxide in methanol. Final purification was carried out by loading the product, dissolved in distilled H$_2$O onto a nonionic amberlite XAD-2 column and washing, with 1 l 3% aqueous Na$_2$EDTA and 2 l doubly distilled water. Elution with methanol afforded 0.1 g (52%) EBD: IR (KBr) 3310, 2950, 1730, 1650, 1640, 1560, 1530, 1460, 1430, 1400, 1260, 1200 cm$^{-1}$; NMR (DMSO-d$^6$) 1.3 (m,2H), 1.65 (m,4H), 1.9 (m,6H), 2.25 (t,4H,J=7 Hz), 2.75 (s,9H), 3.05 (m,6H), 3.2 (m,6H), 3.4 (m,4H), 3.9 (3s, 9H), 3.95 (s,4H), 4.0 (s,2H), 4.1 (s,2H), 6.9 (s,4H), 7.03 (d,2H,J=1.5 Hz), 7.15 (d,2H,J=1.5 Hz), 8.3 (s,2H), 8.9 (t,1H,J=7 Hz), 9.9 (3s,6H); UV (H$_2$O) 303 (70,000)$^{103}$, 235 nm; m/e 1396 (M+).

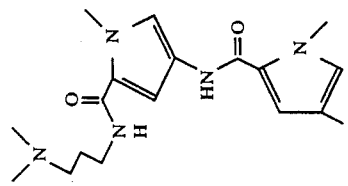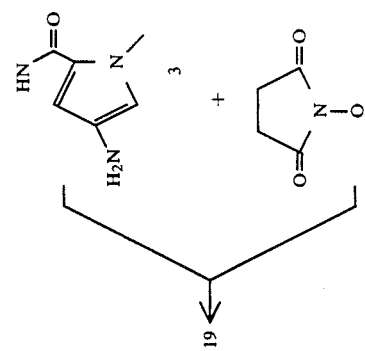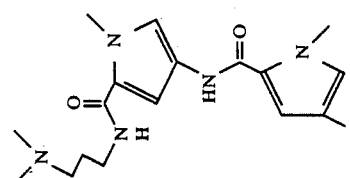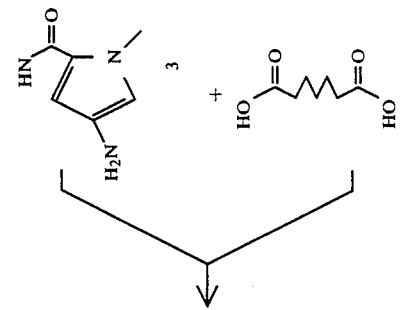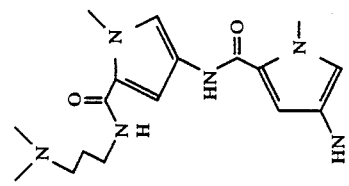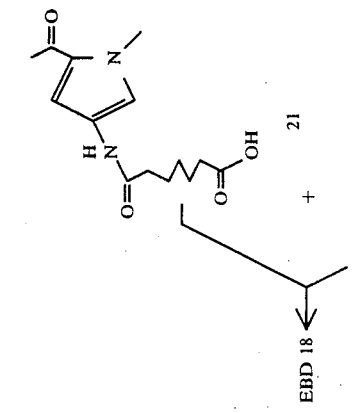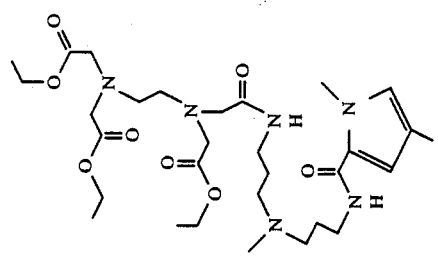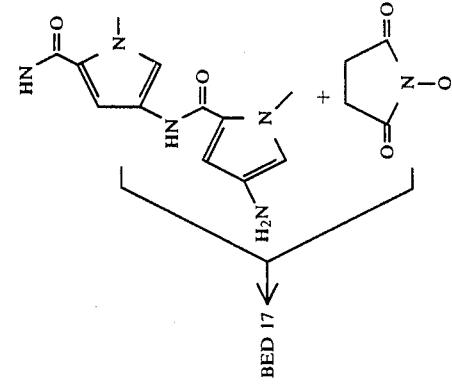

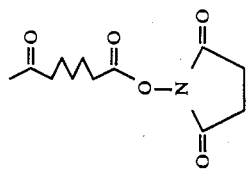
-continued
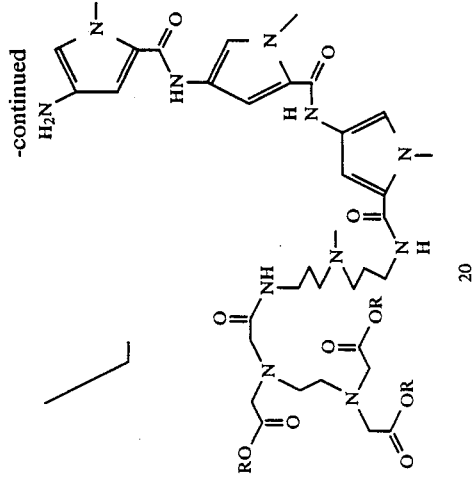
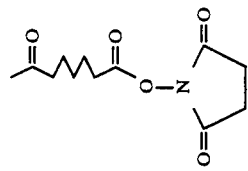

BED and EBD were converted to BED.Fe(II) and EBD.Fe(II), respectively by mixing with Fe(NH$_4$)$_2$.(SO$_4$)$_2$ and DTT at 1 mM concentrations.

The DNA cleavage efficiency of BED.Fe(II) and EBD.Fe(II) was followed by monitoring the conversion of supercoiled pBR 322 plasmid DNA (form I) to open circular (form II) and linear forms (form III). One single strand scission converts from form I to form II. In the presence of O$_2$ and DTT, nanomolar concentrations of BED.Fe(II) and EBD.Fe(II) cleave DNA (10 μM base pair), almost three orders of magnitude lower concentration than required for efficient ED.Fe(II) cleavage. (Table VI) BED.Fe(II) affords a higher proportion of form III linear DNA than EBD.Fe(II) at 10$^{-7}$ and 10$^{-8}$M suggesting that BED.Fe(II) may cleave on opposite strands in a single binding event.

TABLE VI

Cleavage of pBR 322 Plasmid

| Reagent | conc. μM | Form % I | II | III |
|---|---|---|---|---|
| ED.Fe (II) | 10.0 | 0 | 80 | 20 |
| ED.Fe (II) | 1.0 | 10 | 85 | 5 |
| EBD.Fe (II) | 0.010 | 0 | 82 | 18 |
| EBD.Fe (II) | 0.001 | 43 | 48 | 9 |
| BED.Fe (II) | 0.010 | 9 | 55 | 36 |
| BED.Fe (II) | 0.001 | 48 | 42 | 10 |

Form I pBR 322 (10 μM bp), reagent, buffer (40 mM Tris base, 5 mM NaOAc, pH 7.9) and DTT (5 mM) were allowed to react at 25° C. for one hour and quenched. In all cases reactions were carried to completion. Forms I, II, and III were analyzed by agarose gel electrophoresis and qualtitated by densitometry after ethidium bromide straining.

Sequence specific double strand cleavage of DNA by BED.Fe(II) and EBD.Fe(II) was examined on linear pBR 322 plasmid DNA (4362 bp). (Linear pBR-322 was obtained by digestion of supercoiled pBR 322 with Eco RI and Sal I restriction enzymes, respectively). BED.Fe(II) or EBD.Fe(II) (0.25 μM or 0.06 μM) was equilibrated with linear pBR 322 DNA (50 μMbp) for 30 min (37° C.), followed by addition of DTT (5 mM). After one hour, the reaction was quenched and analyzed by agarose gel electrophoresis. Both BED.Fe(II) and EBD.Fe(II) (0.06 μM) cleave linear pBR 322 into discrete fragments. Restriction mapping indicates the major cleavage sites are at approximately 3.3 and 4.2 kilobases, (The cleavage sites were located by initially linearizing pBR-322 with Eco RI, Sal I, Nde I, Ava I, Eco RI+Sal I, Hind II+Ava I, Taq I, and Rsa I restriction enzymes, followed by BED.Fe(II) or EBD.Fe(II) cleavage. Changes in the lengths of the resulting DNA fragments could be correlated with cleavage sites.) regions of pBR 322 with high poly (dA).poly(dT) content. Cleavage specificity diminishes at higher concentrations of BED.Fe(II) and EBD.Fe(II), presumably due to cleavage at sites of diminished binding affinity.

The sequence and size of BED.Fe(II)/EBD.Fe(II) recognition sites can be resolved by analysis of DNA cleavage patterns using $^{32}$P end-labeled restriction fragments and high resolution denaturing polyacrylamide gel electrophoresis. A 517 base pair Rsa I/Eco RI restriction fragment (3848–4362 bp) from pBR 322 was labeled separately with $^{32}$P (Eco RI site) on the 5' and 3' ends. The resulting DNA fragments were allowed to react with BED.Fe(II) or EBD.Fe(II) at dimer/bp ratios of 0.01 in the presence of DTT (1 mM) for one hour (The reactions were run with >600 cpm of $^{32}$P end labeled restriction fragments made up to a total DNA concentration of 100 μM (bp) with sonicated calf thymus DNA. The reactions were run at 25° C. for 1 hour and terminated by freezing, lyophilized and suspended in 4 μl of a pH 8.3 100 mM Tris-Borate, 50% formamide solution. These solutions were heat denatured and loaded on a 0.4 mm thick, 40 cm long, 8% polyacrylamide, 1:20 crosslinked, 50% urea gel and electrophoresed at 1500 V. Autoradiography of the gels was carried out at −50° C. on Kodak, X-Omat AR film and the autoradiograms scanned at 485 nm. The relative peak area for each site was equated to the relative cleavage efficiency.) and analyzed by gel electrophoresis. A histogram of the DNA cleavage patterns obtained from densitometric analysis of the autoradiograms reveals a major cleavage site contiguous to the eight base pair sequence 5'-TTTTTATA-3' and a minor site contiguous to the five base pair sequence 5'-AATAA-3'.

The multiple asymmetric cleavage patterns on opposite DNA strands presumably result from a diffusible oxidizing species, such as hydroxyl radical, generated in the minor groove of a right-handed DNA double helix. (The DNA cleavage products are consistent with oxidative cleavage of the deoxyribose ring affording a 5' phosphate DNA terminus and approximately equal proportions of 3' phosphate and 3' phosphoglycolate termini. Like the tripeptides DE and ED, the dimer EBD can apparently assume two orientations on the DNA. The eight base pair 5'-TTTTTATA-3' and the five base pair 5'-AATAA-3' binding sites suggest that the hydrocarbon tether allows both dimeric and monomeric binding modes. Changes in linker length and/or flexibility might lead to exclusive dimeric binding.

In conclusion, we have found that the dimer of a sequence specific single strand DNA cleaving molecule results in molecules capable of double strand cleaving plasmid pBR 322 into discrete fragments. This work illustrates a general strategy for the design of double strand DNA cleaving molecules with defined target sequences and binding site sizes.

EXAMPLE VII

The synthesis of bis (EDTA-distamycin) phenoxazone and the sequence specific cleavage of DNA restriction fragments is carried out as follows.

The synthetic route to bis (EDTA-distamycin) phenoxazone (BEDP) is as follows:

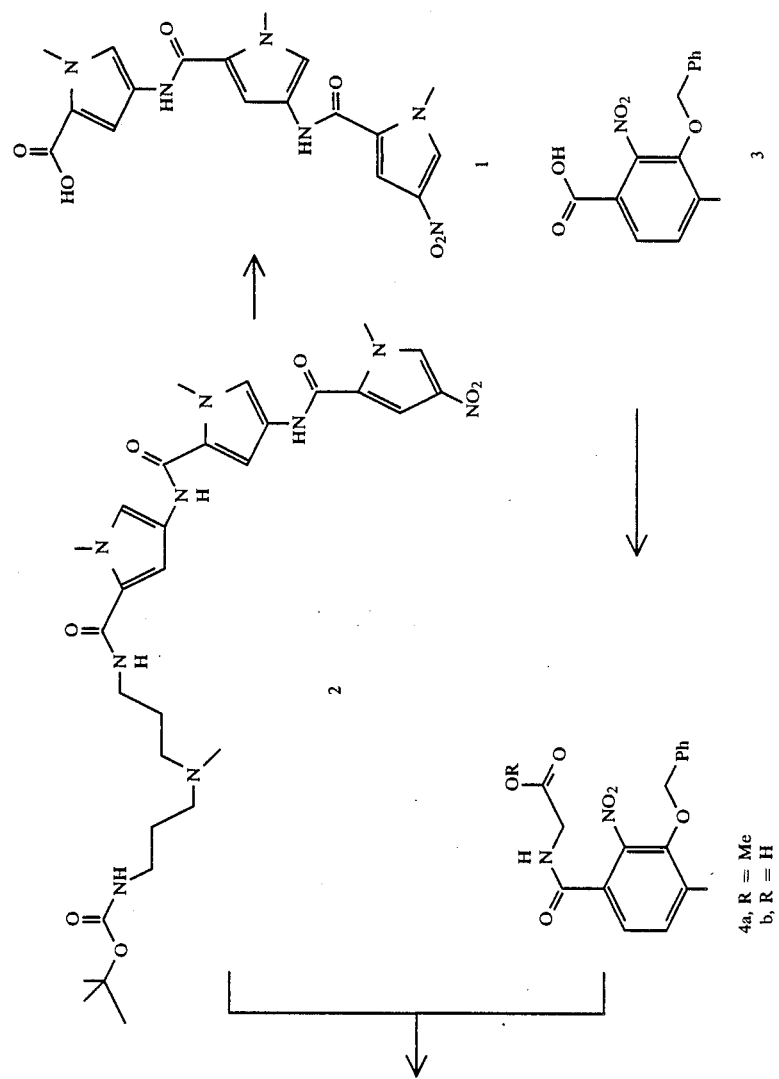

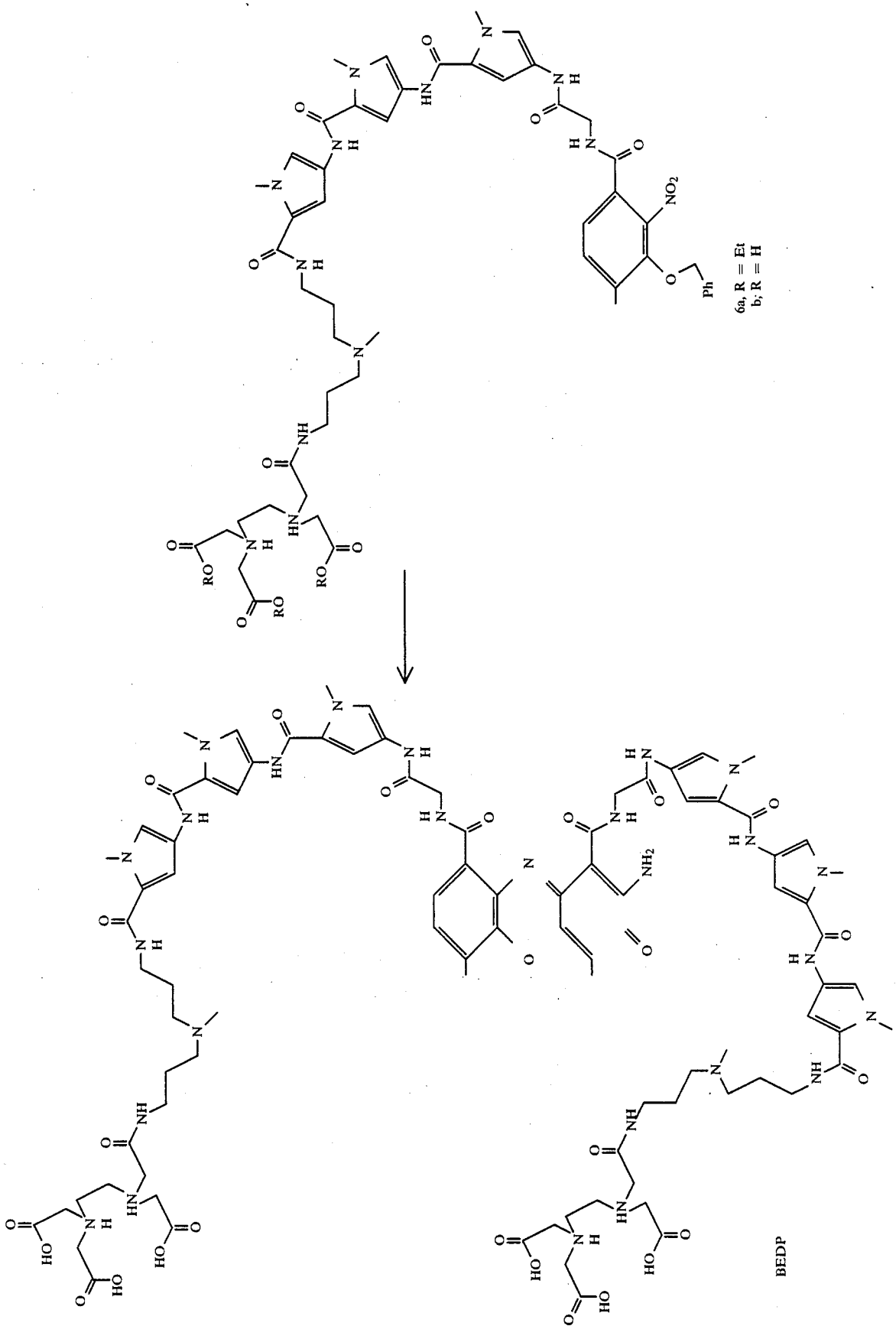

Compound 1 was prepared in eight steps (27% overall) from N-methylpyrrole-2-carboxylic acid.[40] N,N'-Carbonyldiimidazole mediated coupling of 1 with mono-tBOC protected 3,3'-diamino-N-methyldipropylamine (13) afforded 2 in 79% yield. The protected aromatic precursor to the phenoxazone ring system (4b) was prepared in three steps from the commercially available 3-hydroxy-4-methyl-2-nitrobenzoic acid in 83% overall yield. Catalytic hydrogenation of 2 and subsequent condensation with the carbonyldiimidazole adduct of 4b gave 5a in 48% yield. Deprotection of 5a (5b, 93%) and condensation with excess carbonyldiimidazole activated EDTA-triethyl ester afforded 6a in 95% yield. Saponification of 6a, catalytic hydrogenation of 6b and subsequent oxidative coupling with pottassium ferricyanide in 1:1 methanol/phosphate buffer (pH 7.1) followed by chromatography on Amberlite XAD-2 gave the red-orange hexazwitter ion of BEDP in 60% yield. The details are as follows:

3-Benzyloxy-4-methyl-2-nitrobenzamide glycine methyl ester, 4a: A solution of 7.0 g (24 mmol) 3-benzyloxy-4-methyl-2nitrobenzoic acid[43]) and 4.4 g (27 mmol) acydiimidazole in 60 ml DMF was allowed to stir for 24 hours under a dry atmosphere. N-ethylmorpholine (3.4 g, 27 mmol) and 3.4 g (27 mmol) glycine methyl ester hydrochloride were added and stirring continued for 12 hours. The reaction mixture was diluted with 600 ml chloroform and extracted with 2.5% sodium bicarbonate (3×150 ml), 5% hydrochloric acid (2×150 ml), water (3×150 ml) and saturated sodium chloride (150 ml). The organic layer was dried (Na$_2$SO$_4$) and the chloroform removed under reduced pressure affording 8.0 g (91%) 4a as a cream colored solid which was pure by TLC:NMR(CDCl$_3$)δ 7.33 (m, 7H), 6.74 (t, 1H, j=5 Hz), 4.89 (s, 2H), 4.06 (d, 2H, j=5 Hz), 3.74 (s, 3H), 2.31 (s, 3H).

2-Nitro-3-benzyloxy-4-methylbenzamide glycine, 4b: To a solution of 7.5 g (21 mmol) 4a in 250 ml methanol were added 100 ml of 1N lithium hydroxide and the mixture was allowed to stir at room temperature for 2 hours. The methanol was removed under reduced pressure followed by dilution with 150 ml water and slow acidification with 6N hydrochloric acid to pH 1. The product was removed by filtration and washed with 0.1N hydrochloric acid and ether followed by vacuum drying. The 6.8 g of crude product were digested in 250 ml boiling chloroform then allowed to stand at 5° C. overnight. Filtration followed by vacuum drying gave 6.5 g (90%) 4b as marble white crystals: NMR (DMSO-d$_6$) δ 12.7 (s.1H), 9.12 (t, 1H, j=6 Hz), 7.59 (s, 2H), 7.41 (s,5H), 4.94 (s, 2H), 3.86 (d, 2H, j=6 Hz), 2.37 (s, 3H).

3-(t-Butylcarbamide)-3'-amino-N-methyldipropylamine, 13: To 5 g (34 mmol) 3,3'-diamino-N-methylpropylamine (Aldrich) were added 1.9 g (8.7 mmol) di-t-butyldicarbonate (Fluka) and the mixture held at 50° C. for one hour. The mixture was diluted with 30 ml water and extracted with dichloromethane (3×30 ml). The organic layer was concentrated and the crude product flash chromatographed with 12% concentrated aqueous ammonium in methanol. Drying in vacuo gave 0.71 g (34%) 13 as a colorless: NMR (CDCl$_3$) δ 5.75 (bs, 1H) 3.13 (p, 2H, j=6 Hz), 2.73 (t, 2H, j=6 Hz), 2.37 (t, 4H, j=6.8 Hz), 2.17 (s, 3H), 1.7 (m, 6H), 1.49 (s, 9H).

2: To a cold (OC) solution of 1.16 g (2.8 mmol) 1[40]) and 0.91 g (6.7 mmol) N-hydroxybenzotriazole monohydrate in 50 ml DMF were added 0.69 g (3.4 mmol) dicyclohexylcarbodiimide. The mixture was allowed to warm to room temperature overnight with stirring. A solution of 0.72 g (2.9 mmol) 13 in 5 ml DMF was added and stirring continued for 15 hours. Dicyclohexylurea was removed by filtration followed by removal of DMF in vacuo at 40° C. After triturating with ether (3x), the crude product was chromatographed with 0.25% concentrated aqueous ammonia in methanol, giving 1.4 g (79%) 2 as a yellow solid: NMR (DMSO-d$_6$) δ 10.25 (s, 1H), 9.90 (s, 1H), 8.14 (d, 1H, j=1.5 Hz), 8.00 (m, 1H), 7.57 (d, 1H, j=1.5 Hz), 7.22 (d, 1H, j=1.5 Hz), 7.19 (d, 1H, Aj=1.5 Hz), 7.02 (d, 1H, j=1.5 Hz), 6.80 (d, 1H, j=1.5 Hz), 6.7 (m, 1H), 3.92 (s, 3H), 3.83 (s, 3H), 3.78 (s, 3H), 3.2 (m, 4H), 3.25 (m, 4H), 2.12 (s, 3H), 1.6 (m, 4H), 1.37 (s. 9H).

5a: A solution of 1.16 g (1.81 mmol) 2 and 0.2 g palladium on charcoal in 3 ml DMF was hydrogenated under one atom hydrogen for 20 hours followed by removal of the catalyst by filtration through celite. A solution of 0.65 g (1.9 mmol) 4b and 0.34 g (2.1 mmol) acydiimidazole in 0.7 ml DMF, after stirring for one hour, was added to the filtered hydrogenation mixture and allowed to stir for 12 hours. DMF was removed in vacuo at room temperature and the crude product triturated with ether (3x). The product was chromatographed twice with 30% methanol in dichloromethane giving 0.82 g (48%) 5a as a bright yellow solid: NMR (DMSO-d$_6$) δ 10.01 (s, 1H), 9.96 (s, 1h), 9.91 (s, 1H), 9.12 (t, 1H, j=5.8 Hz), 8.06 (t, 1H, j=5.6 Hz), 7.65 (s, 2H), 7.45 (m, 5H), 7.27 (d, 1H, j=1.0 Hz), 7.20 (s, 2H), 7.06 (d, 1H, j=1.1 hz), 6.96 (d, 1H, 1.2 Hz), 6.86 (d, 1H, j=1.3 Hz), 6.82 (t, 1H, 4.8 Hz), 5.00 (s, 2H), 4.01 (d, 2H, j=4.3 Hz), 3.87 (s, 6H), 3.82 (s, 3H), 3.21 (q, 2H, j=5.8 Hz), 2.96 (q, 2H, j=5.8 Hz), 2.53 (s, 3H), 2.32 (m, 4H), 2.16 (s, 3H), 1.64 (p, 2H, j=6.8 Hz), 1.54 (p, 2H, j=6.7 Hz), 1.39 (s, 9H).

5b: To a solution of 725 mg (0.77 mmol) 5a in 15 ml dichloromethane was added 10 ml trifluoroacetic acid. After 10 minutes the mixture was slowly diluted with 75 ml of ether which precipitated the di-trifluoracetic acid salt of 5b. The crude product was chromatographed with 12% concentrated ammonia in methanol giving 605 mg (93%) of 5b as a light yellow solid: NMR (DMSO-d$_6$) δ 10.21 (s, 1H), 9.95 (s, 1H), 9.90 (s, 1h), 9.2 (broad singlet, 1H), 8.05 (t, 1H, j=6 Hz), 7.65 (d, 1H, j=9 Hz), 7.60 (d, 1H, j=9 Hz), 7.42, (m, 5H), 7.25 (d, 1H, 1.0 Hz), 7.19 (s, 2H), 7.05 (d, 1H, j=1 Hz), 6.94(d, 1H, j=1 Hz), 6.83 (d, 1H, j=1 Hz), 4.97 (s, 2H), 3.98(s, 2H), 3.86 (s, 6H), 3.80 (s, 3H), 3.18 (m, 2H), 2.56 (broad singlet, 2H), 2.43 (s, 3H), 2.31 (m, 4H), 2.13 (s, 3H), 1.62 (p, 2H, j=8 Hz), 1.48 (p, 2H, j=7 Hz).

6a: A solution of 900 mg (2.4 mmol) ethylendiamine tetraacetic acid triethyl ester[45]) and 410 mg (2.5 mmol) acydiimidazole in 3 ml DMF was allowed to stir under a dry atmosphere for one hour followed by the addition of 466 mg (0.56 mmol) 5b in 0.5 ml DMF. After stirring for 15 hours, the DMF was removed in vacuo at room temperature and the product triturated with ether (4x). Flash chromatography with 1% concentrated aqueous ammonia in methanol afforded 630 mg (95%) 6a as a yellow solid: NMR (DMSO-d$_6$) δ 9.97 (s, 1H), 9.90 (s, 1H), 9.87 (s, 1H), 9.08 (t, 1H, j=5 Hz), 8.00 (t, 1H, j=4 Hz), 7.95 (t, 1H, j=5 Hz), 7.64 (d, 1H, j=10 Hz), 7.62 (d, 1H, j=10 Hz), 7.41 (m, 5H), 7.24 (d, 1H, j=1.5 Hz), 7.16 (s, 2H), 7.03 (d, 1H), j=1.5 Hz), 6.93 (d, 1H, j=1.5 Hz), 7.84 (d, 1H, j=1.5 Hz), 4.96 (s, 2H), 4.05 (q, 6H, j=7 Hz), 3.97 (s, 2H), 3.85 (s, 6H), 3.79 (s, 3H), 3.50 (s, 6H), 3.12 (q, 2H, j=6.7 Hz), 2.72 (t, 2H, j=6.3 Hz), 2.67 (t, 2H, j=6.3 Hz), 2.42 (s, 3H), 2.31 (t, 2H, j=8.3 Hz), 2.29 (t, 2H, j=8.3 Hz), 2.13 (s, 3H), 1.62 (p, 2H, j=7 Hz), 1.56 (p, 2H, j=7 Hz), 1.17 (t, 9H, j=7 Hz).

6b: To a solution of 200 mg (167 μmol) 6a in 5 ml of methanol was added 1.5 ml of 1M lithium hydroxide and the mixture was allowed to stir in the dark at room temperature for 4 hours. The solvents were removed under reduced pressure and the product chromatographed on silica gel with 2% concentrated aqueous ammonia in methanol affording 170 mg (91%) 6b as a light yellow solid. NMR (1:10 trifluoroacetic acid/DMS-O-d$_6$) δ 10.00 (s, 1H), 9.96 (s, 1H), 9.94 (s, 1H), 9.42 (bs, 1H), 9.13 (t, 1H, j=6 Hz), 8.53 (t, 1H, j=6 Hz), 8.22 (bs, 1H), 7.67 (d, 1H, j=8 Hz), 7.61 (d, 1H, j=8 Hz), 7.44 (m, 4H), 7.41 (m, 1H), 7.25 (d, 1H, j=1.3 Hz), 7.20 (s, 2H), 7.12 (d, 1H, j=1.3 Hz), 7.01 (d, 1H, j=1.7 Hz), 6.99 (d, 1H, j=1.3 Hz), 4.99 (s, 2H), 4.07 (s, 2H), 4.01 (d, 2H, j=5 Hz), 3.98 (s, 2H), 3.94 (s, 2H), 3.88 (s, 9H), 3.85 (s, 4H), 3.36 (m, 2H), 3.30 (m, 4H), 3.25 (q, 2H, j=6 Hz), 3.08 (m, 2H), 2.81 (d, 3H, j=4 Hz), 2.45 (s, 3H), 1.90 (m, 4H).

BEDP: A mixture of 120 mg (108 μmol) 6b and 30 mg 5% palladium on carbon was hydrogenated under one atmosphere hydrogen in the dark for three hours. Under an argon atmosphere the catalyst was removed by filtration through celite and the celite was washed with 2 ml methanol. The solution was diluted with 12 ml of 67 mM phosphate buffer (pH 7.1) and 89 mg (270 μmol, 2.5 eq.) pottasium ferricyanide in 1 ml phosphate buffer was added. The solution was stirred for two minutes during which time it turned deep red-orange characteristic of the phenoxazone moeity. The solution was allowed to stand for two hours followed by removal of solvents under reduced pressure. The crude product was dissolved in minimal water and loaded on an Amberlite XAD-2 (Kodak) column. The column was washed with water (150 ml), 3% EDTANa$_2$ (500 ml) and water (1 L). The BEDP was eluted with 50% aqueous methanol. The solvents were removed in vacuo, the product was triturated with 2 ml methanol and dried; 67 mg (68%) BEDP as a red-orange solid. UV/VIS (H$_2$O) 438 nm (phenoxazone), 305 nm (pyrroles), 235 nm; ε305/ε438=3.0, expected ε305/ε438=3.0. NMR (1:10 triflouroacetic acid/D-MSO-d$_6$) δ 10.02 (s, 1H), 9.93 (s, 3H), 9.90 (s, 1H), 9.83 (s, 1H), 9.44 (bs, 2H), 9.08 (t, 1H, j=6 Hz), 8.59 (t, 2H, j=5 Hz), 8.24 (bs, 1H), 8.10 (bs, 2H), 7.72 (d, 1H, j=8 Hz), 7.46 (d, 1H, j=8 Hz), 7.25 (s, 1H), 7.23 (s, 1H), 7.20 (s, 4H), 7.17 (s, 1H), 7.15 (s, 1H), 7.07 (s, 2H), 7.02 (s, 2H), 4.44 (s, 8H), 4.03 (s, 4H), 4.00 (s, 8H), 3.88 (m, 18H), 3.57 (s, 3H), 3.52 (q, 6H, j=7 Hz), 3.48 (m, 6H), 3.34 (bs, 4H), 3.29 (q, 6H, j=7 Hz), 3.21 (m, 4H), 3.14 (m, 4H), 2.84 (d, 6H, j=4 Hz), 2.56 (s, 3H), 2.20 (s, 3H), 1.95 (m, 8H).

The DNA cleavage efficiency of BEDP.Fe(II) was investigated by monitoring the conversion of supercoiled pBR322 plasmid DNA (form I) to open circular (form II) and linear form (form III) (Table 1). One single strand scission converts form I to II. In the presence of O$_2$ and dithiothreitol (DTT), 0.1 μM concentration of BEDP.2Fe(II) converts form I to 82% form II and 18% form III.

TABLE I

| Cleavage[a] of pBR322 by BEDP.Fe (II). | | | | |
|---|---|---|---|---|
| BEDP.Fe (11) (μM) | I[b] | % II | III | % low mw linear DNA |
| 1.0 | 0 | 15 | 28 | 58 |
| 0.1 | 0 | 82 | 18 | 0 |
| 0.01 | 58 | 39 | 3 | 0 |
| 0.001 | 86 | 14 | 0 | 0 |

[a]10 μM bp,buffer (40 mM Tris,5 mM NaOAc, pH 7.9), 5 mM DTT. Reactions run 1 hour at 25° C. BEDP.2 Fe(II) annealed with pBR 322 5 min at 65° C. prior to addition of DTT.
[b]Corrected for decreased stainability of form I DNA.

The sequence and site size of the DNA binding sites were exmined by analysis of DNA cleavage on $^{32}$P end-labeled DNA restriction fragments by denaturing polyacrylamide gel electrophoresis. A 517 base pair Rsa I/Eco RI restriction fragment (base pairs 3848 to 4362) from plasmid pBR322 DNA was labeled separately with $^{32}$P on the 5' and 3' ends. The DNA fragments were allowed to react with BEDP.2Fe(II) (5 μM concentration) at BEDP/DNA base pair ratio of 0.05 in the presence of DTT (5 mM) for two hours (37° C., pH 7.9). The DNA cleavage sites were visualized by high resolution gel electrophoresis (FIG. 7). From densitometric analysis of the autoradiogram (lower third of FIG. 8), the DNA cleavage patterns reveals a major cleavage site flanking the ten base pair sequence, 5'-TATAGGT-TAA-3' (FIG. 8). One interpretation of the data suggests that the tripeptides are binding simultaneously at A-T rich sequences, four base pairs in size, flanking a central 5'-GG-3' phenoxazone binding site. Although not a proof, this is consistent at least in a formal sense with the groove binder-intercalator-groove binder mode.

However, at two other sites (middle of the autoradiogram) single cleavage loci are observed. One interpretation of this data is that only one tripeptide or possibly a tripeptide-phenoxazone (groove binding-intercalation) is binding at these sites. The absence of two cleavage loci does not allow the assignment of binding location and site size.

EXAMPLE VIII

The general reaction scheme is as follows:

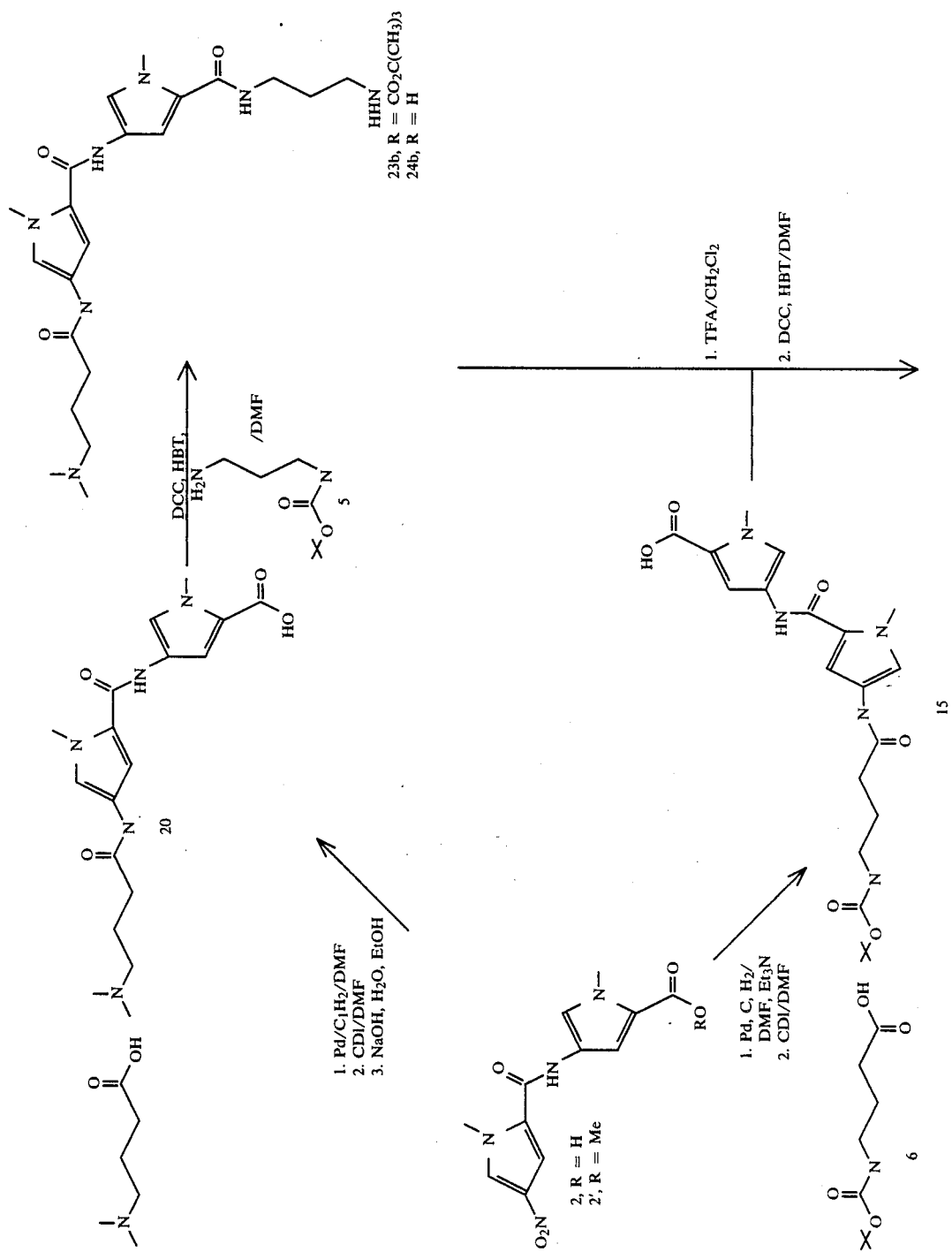

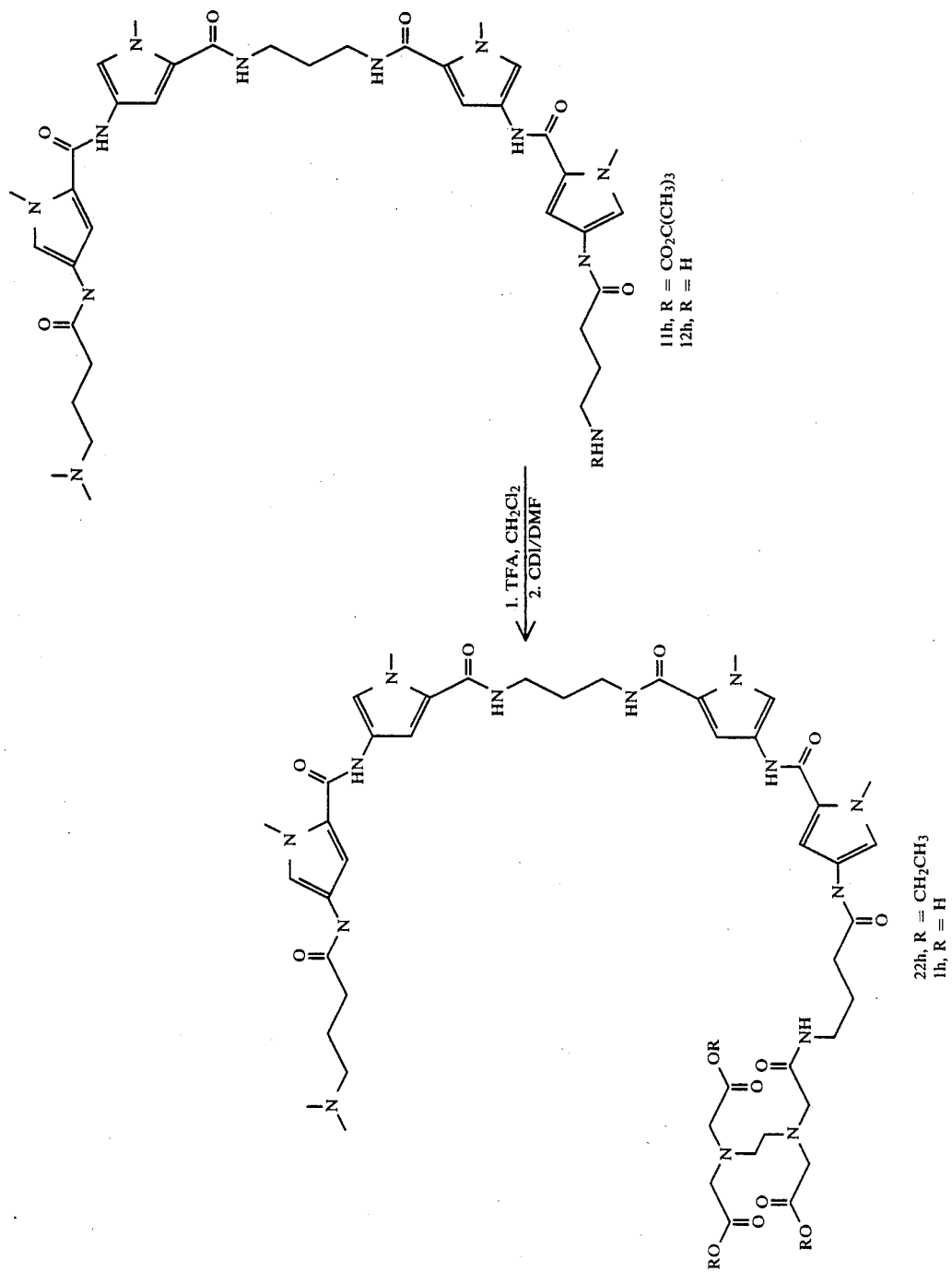

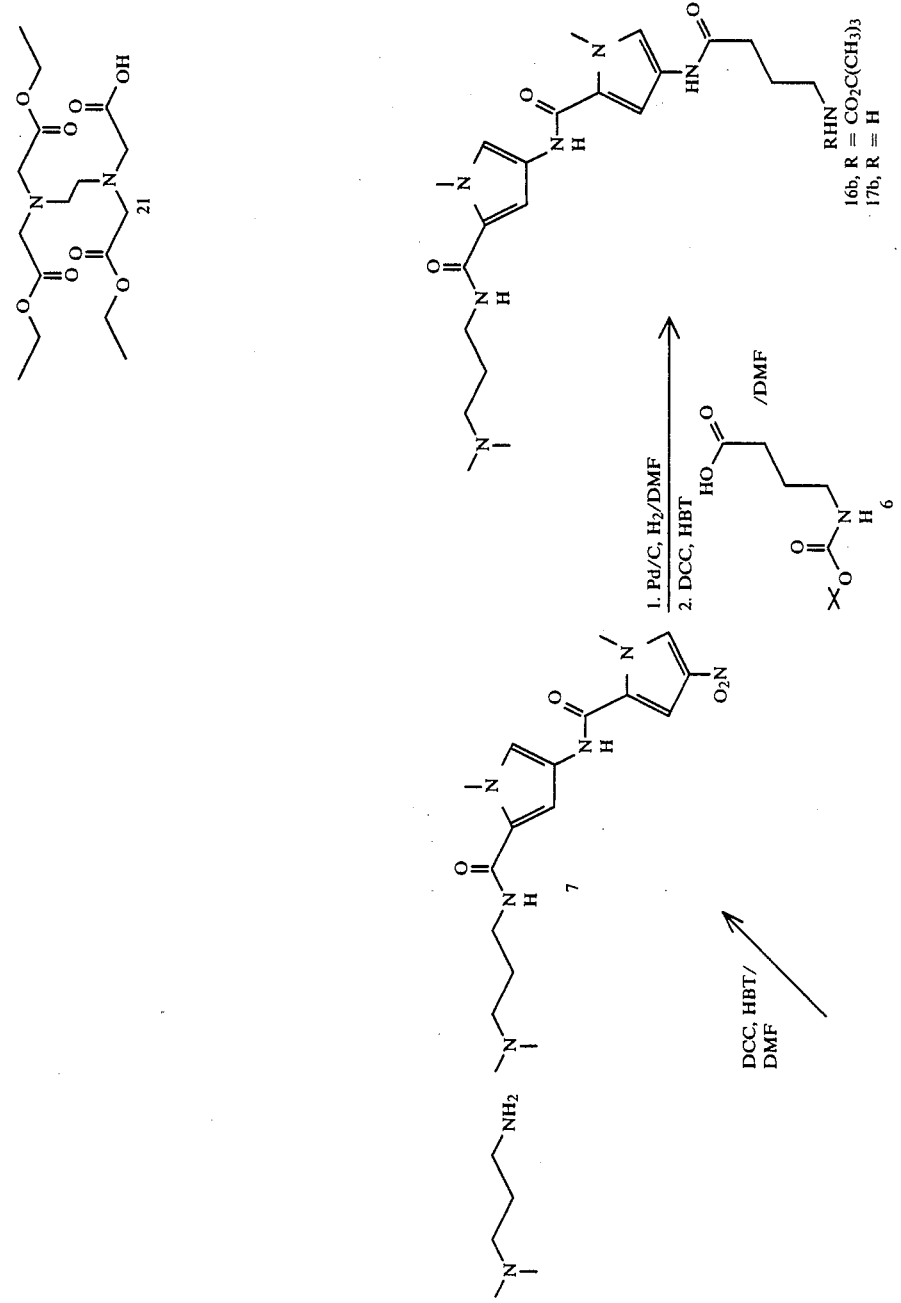

-continued
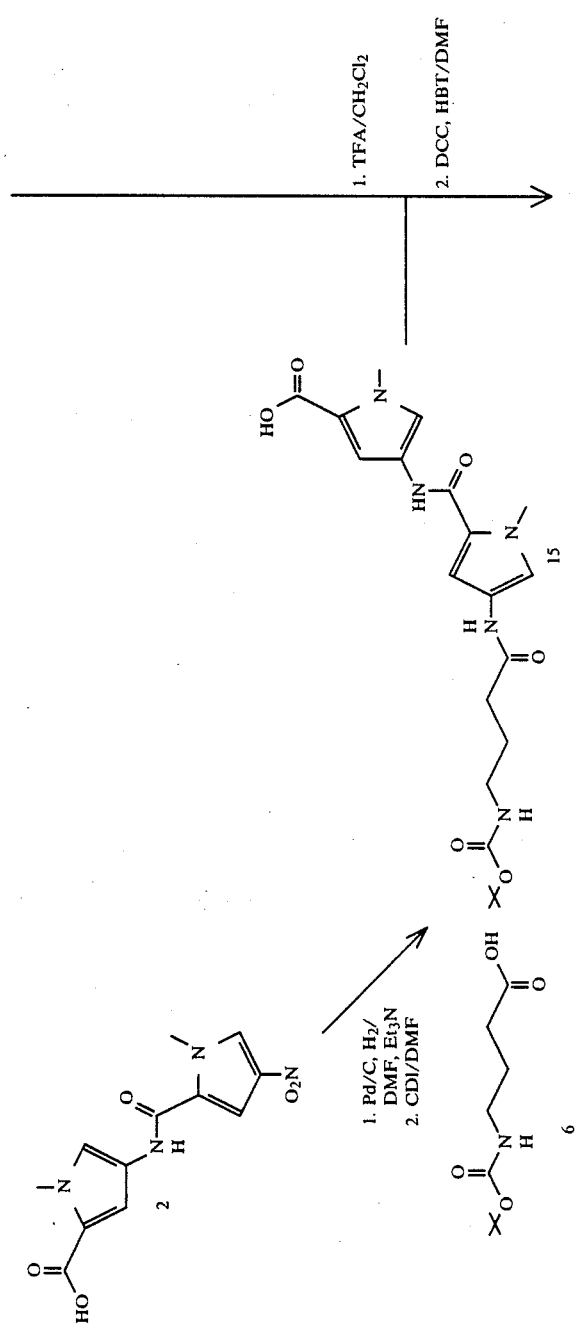

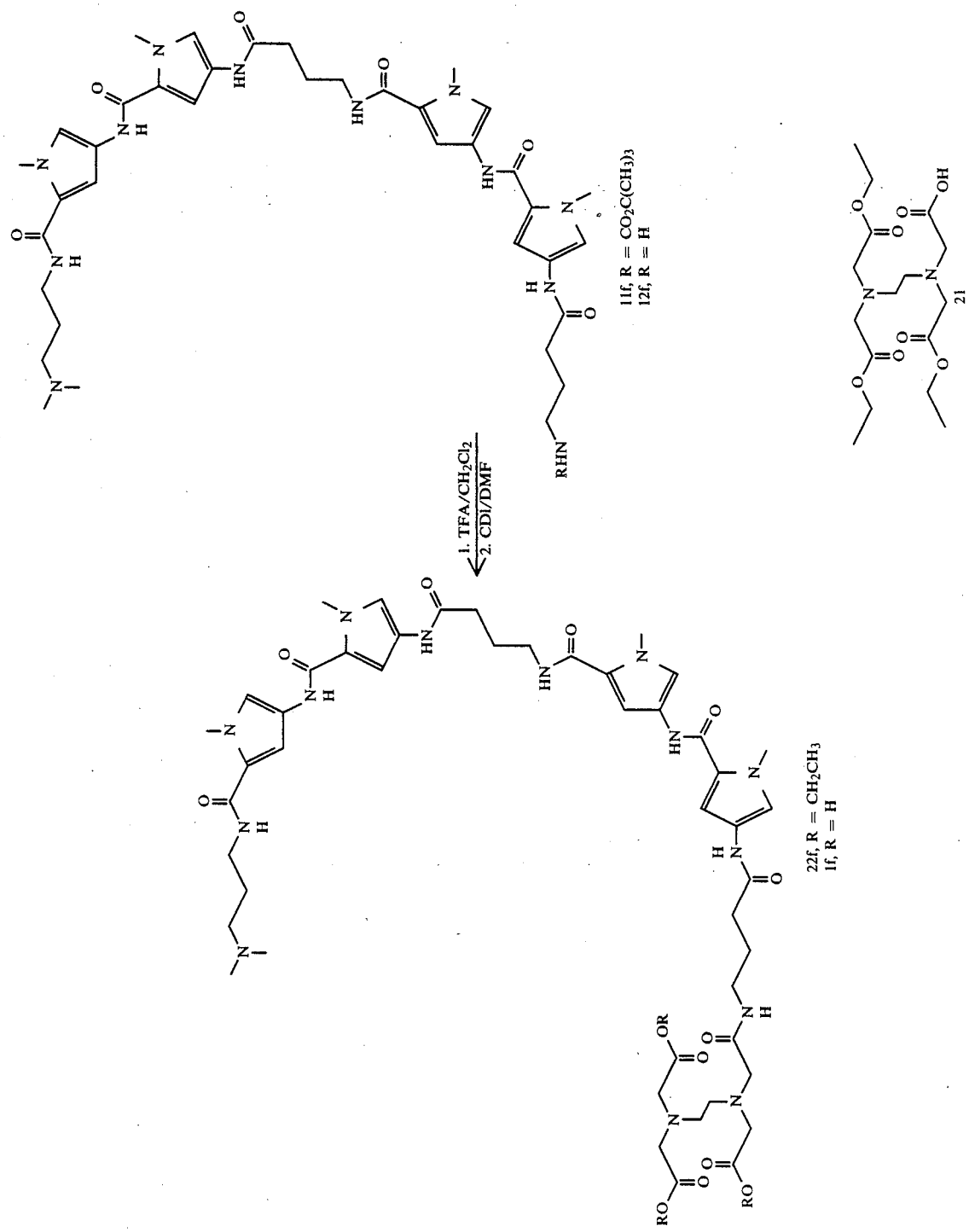

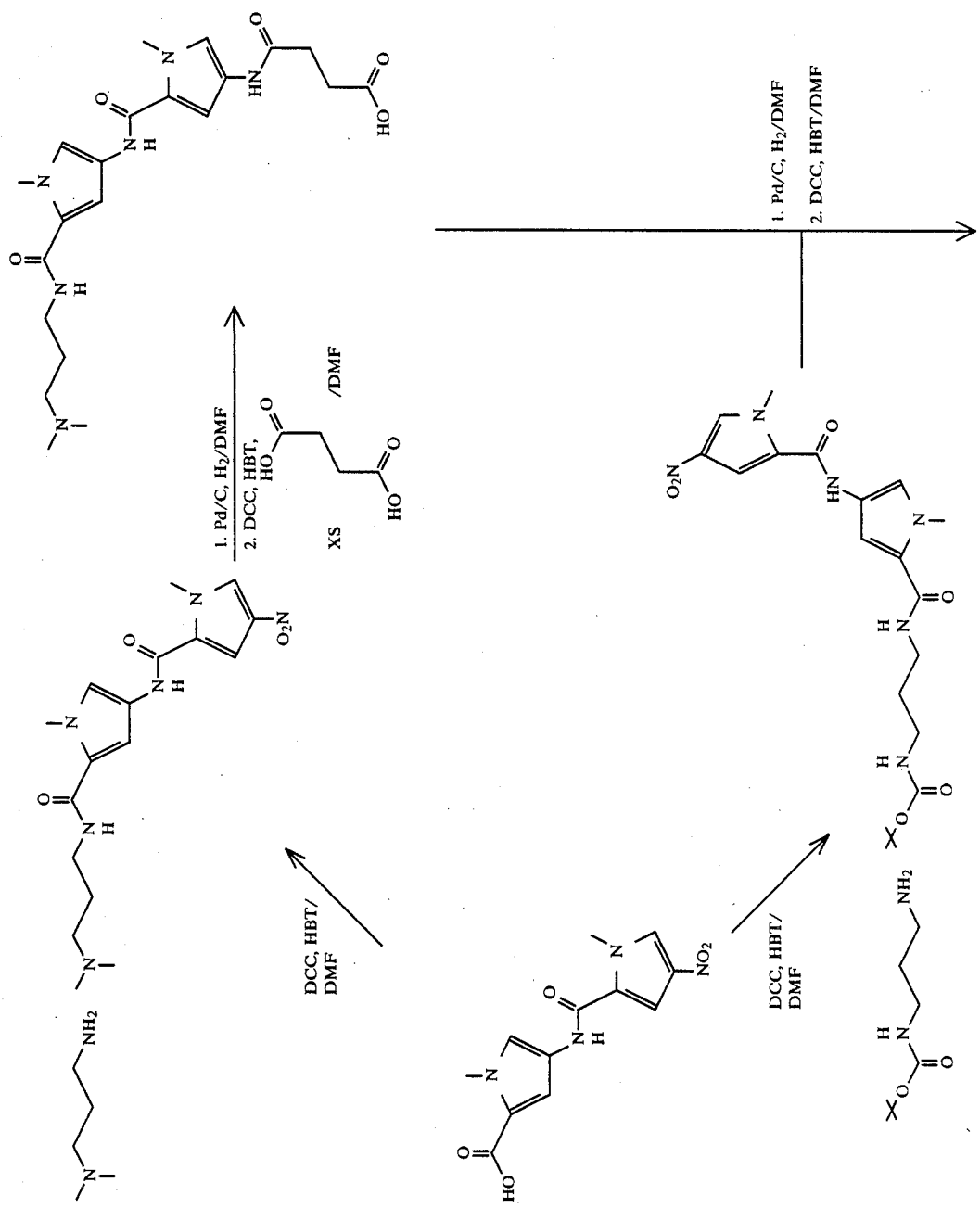

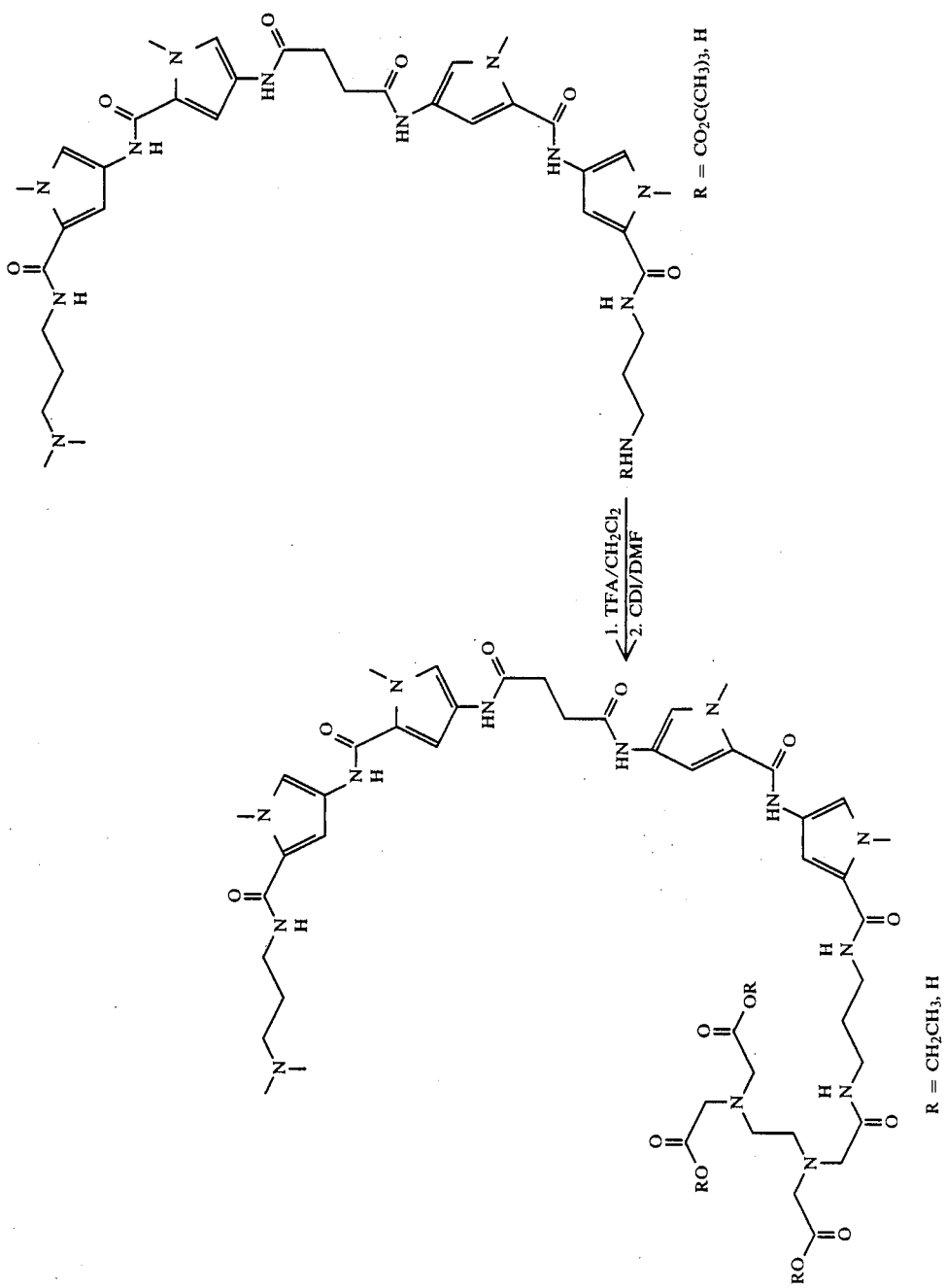

-continued
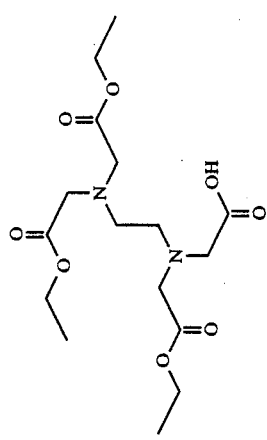
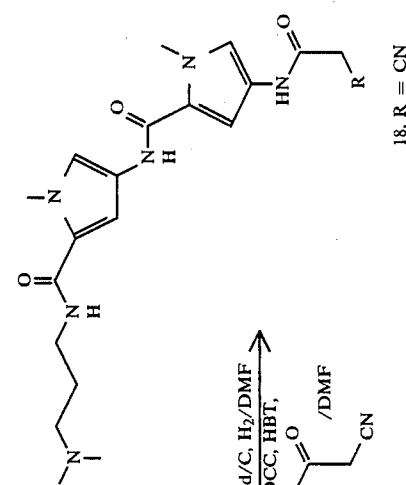
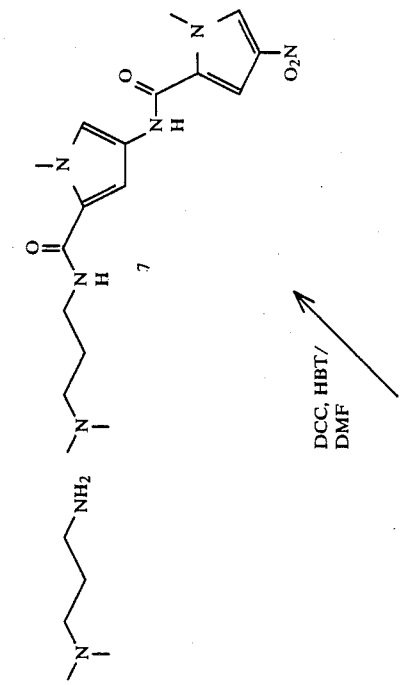

-continued
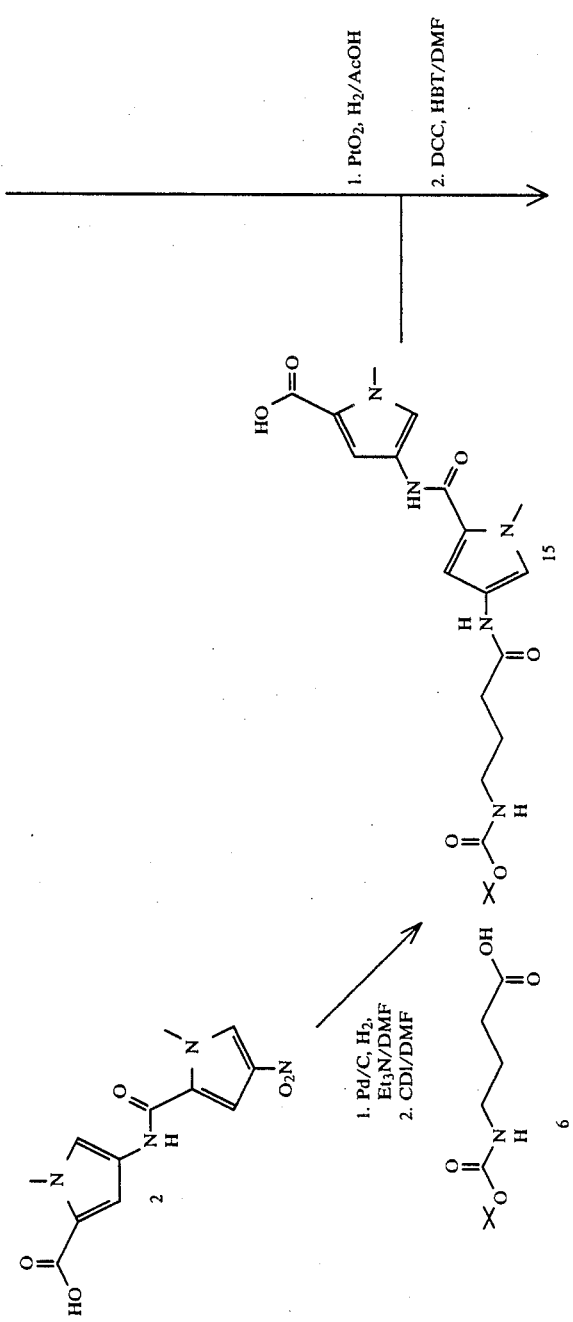

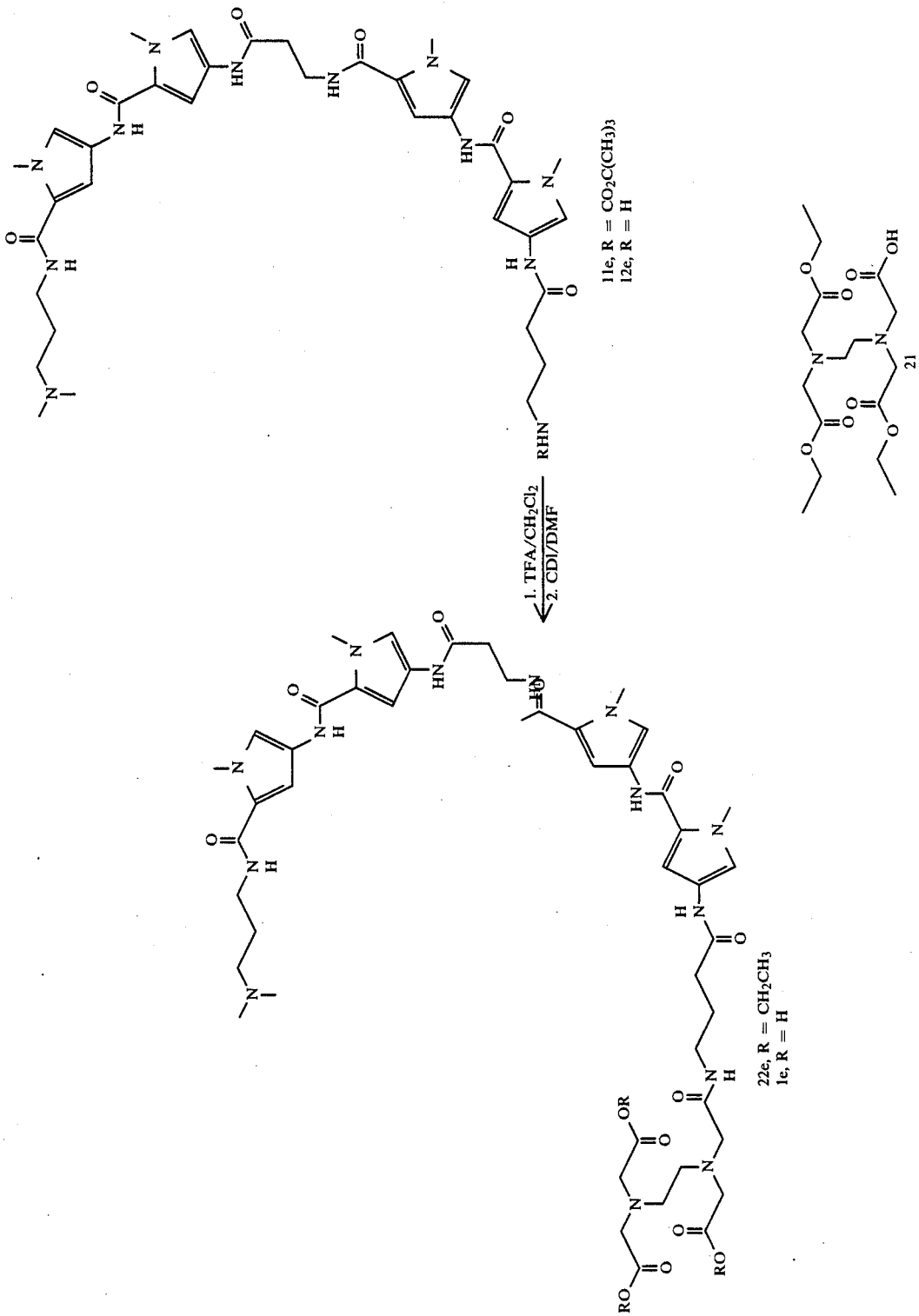

Synthesis. General. ¹H NMR spectra were recorded at 90 MHz on Varian EM-390 or JEOL FX-90Q instruments, or at 400 MHz on a JEOL JNM-GX400. Solvent for NMR was $Me_2SO\text{-}d_6$ unless otherwise noted. Chemical shifts are reported in parts per million downfield from internal $Me_4Si$. High resolution fast atom bombardment mass spectra (FAB MS) were obtained from the Midwest Center for Mass Spectrometry at the Univesity of Nebraska, Lincoln, to which acknowledgement is made. IR spectra were recorded on a Schimadzu Ir-435 instrument. UV spectra were recorded on a Cary 219 Spectrophotometer in the baseline correct mode.

Chromatography was carried out under positive air pressure using EM Science Kieselgel 60 (230–400 Mesh). Reagent grade chemicals were used as received except for N,N-dimethylformamide (DMF, Mallinckrodt), which was dried over 4A° molecular sieves. All non-aqueous reactions were carried out under argon.

N-Methyl-4(N-methyl-4-nitropyrrole-2-carboxamide)-pyrrole-2-carboxylic acid (2) was prepared as previously described[1] from commercially available N-methylpyrrole-2-carboxylic acid.

Mono-t-boc diamines(3–5). To a stirred solution of Imidazole-N-carboxylic acid, t-butylester[2] (0.85 g, 5 mmol) and sodium imidazole (0.045 g, 0.5 mmol) in 10 mL dry THF was added 5.5 mmol of ethane-, propane-, or butanediamine. The mixture was stirred overnight at room temperature (RT), and the solvent removed at RT under reduced pressure. The residue was taken up in water and extracted 3 times with $CH_2Cl_2$. The combined extracts were dried over sodium sulfate, and concentrated to a thick oil. Chromatography on silica gel using 3% $NH_4OH$/MeOH eluent afforded 3–5 as pale yellow oils.

1,2-diaminoethane, mono-t-butylcarbamate (4), 53%. ¹H NMR ($CDCl_3$) δ 3.18 (q, 2H), 2.80 (t, 2H), 1.45 (s, 11H).

1,3-Diaminopropane, mono-t-butylcarbamate (3), 49%. ¹H NMR ($CDCl_3$) δ 4.93 (br s, 1H), 3.18 (q, 2H). 2.72 (t, 2H), 1.66 (s, 2H), 1.58 (m, 2H), 1.42 (s, 9H).

1,4-Diaminobutane, mono-t-butylcarbamate (5), 81%. ¹H NMR δ 6.78 (t, 1H), 2.89 (q, 2H), 2.50 (t, 2H), 1.37 (s, 9H), 1.30 (m, 4H).

4-Aminobutyric acid, t-butylcarbamate (6).[3] To a stirred, cooled solution of 4-aminobutyric acid (10.3 g, 100 mmol) in 400 mL 2:1:1 dioxane:$H_2O$:1 N NaOH was added di-t-butyldicarbonate (24.0 g, 10 mmol) in 10 mL dioxane over 30 min. The mixture was stirred for 30 min in the cooling bath and then for 45 min at RT. Dioxane was removed at RT under reduced pressure. The aqueous solution was treated with 400 mL of ethyl acetate, and then acidified to ph using 2 N $KHSO_4$ with cooling and vigorous stirring. The layers were separated and the aqueous phase extracted with 2×200 mL ethyl acetate. The combined extracts were washed with 200 mL $H_2O$, dried over $Na_2SO_4$, and concentrated to a thick oil which solidified upon standing. Stirring the crushed solid with 100 mL hexane removed remaining t-butanol. Filtration afforded 13.5 g (68 mmol, 68%) of 6 as a fluffy white solid. ¹H NMR δ 6.81 (t, 1H), 2.92 (m, 2H), 2.19 (t, 2H), 1.59 (m, 2H), 1.37 (s, 9H).

N-Methyl-4-(N-methyl-4-nitropyrrole-2-carboxamide)-pyrrole-2-carboxamide-N,-N-dimethylpropylamine (7). A solution of 2 (1.46 g, 5.0 mmol), 1-hydroxybenzotriazole hydrate (1-HBT, 1.35 g, 10.0 mmol), and 3-dimethylaminopropylamine (0.7 mL, 5.5 mmol) in 50 mL DMF was stirred under argon in an ice/water bath. Dicyclohexycarbodiimide (DCC, 1.15 g, 5.5 mmol) in 5 mL DMF was added and the reaction mixture allowed to warm to RT and stir for 24 h. The mixture was filtered, the solvent distilled in vacuo, and the residue triturated with ether. Chromatography on silica gel using 1% (v/v) concentrated aqueous ammonia in methanol (1% $NH_4OH$/MeOH) afforded 1.67 g (4.4 mmol, 88%) of 7 as a yellow solid. ¹H NMR δ 10.23 (s, 1H), 8.13 (s, 1H), 8.07 (t, 1H), 7.53 (s, 1H), 7.17 (s, 1H), 6.77 (s, 1H), 3.90 (s, 3H), 3.77 (s, 3H), 3.2 (m, 2H); FAB MS, calcd. for $C_{17}H_{25}N_6O_4$ (M+H+): 377.1937. Found: 377.1925.

N-Methyl-4-(N-methyl-4-nitropyrrole-2-carboxamide)pyrrole-2-carboxamidepropyl-t-butylcarbamate (8). A solution of 2 (1.46 g, 5.0 mmol), 1-HBT (1.35 g, 10.0 mmol), and 4 (0.87 g, 5.0 mmol) in 50 mL DMF was stirred under argon in an ice/water bath. DCC (1.13 g, 5.5 mmol) in 1 mL DMF was added and the reaction mixture allowed to warm to RT and stir for 24 h. The mixture was filtered, and the solvent distilled in vacuo. Trituration with ether afforded a fluffy solid which could be precipitated from $CHCl_3$ to afford 1.70 g (3.8 mmol, 76%) of 8 as a white solid in two crops. ¹H NMR δ 10.25 (s, 1H), 8.17 (s, 1H) 7.97 (t, 1H), 7.50 (s, 1H), 7.18 (s, 1H), 6.83 (s, 1H), 6.74 (t, 1H), 3.93 (s, 3H), 3.78 (s, 3H), 3.20 (m, 2H), 2.96 (m, 2H), 1.61 (m, 2H), 1.40 (s, 9H): FAB MS calcd. for $C_{20}H_{29}N_6O_6$ (M+H+): 449.2149. Found: 449.2145.

N,N-Dimethylamino acids (10a–c). Compound 7 (0.42 g, 1.1 mmol) was dissolved in 10 mL DMF and treated with 50 mg of 5% palladium on charcoal (5% Pd/C). This mixture was hydrogenated at atmospheric pressure and RT for 16 h, then treated with 1-HBT (0.27 g, 2.0 mmol) and 5–10 mmol of malonic, succinic, or fumaric acid (9a, 9b, or 9c, respectively). This mixture was stirred under argon in an ice bath and treated with DCC (0.23 g, 1.1 mmol) in 1 mL DMF. The cooling bath was removed and the mixture stirred overnight at RT. The mixture was filtered, the solvent distilled in vacuo, and the residue triturated with ether, Chromatography on silica gel using 1–2% $NH_4O\text{-}H$/MeOH eluent afforded 10a–c as yellow solids.

N-Methyl-4-[N-mehtyl-4-(malonamic acid)-pyrrole-2-carboxamide]pyrrole-2-carboxamide-N,N-dimethylpropylamine (10a), 49%. ¹H NMR δ 10.55 (s, 1H), 9.83 (s, 1H), 8.08 (t, 1H), 7.18 (d, 1H), 7.16 (d, 1H), 6.89 (s, 1H), 6.84 (s, 1H), 3.83 (s, 3H), 3.80 (s, 3H), 3.18 (m, 2H), 3.17 (s, 2H), 2.46 (t, 2H), 2.30 (s, 6H), 1.68 (m, 2H); FAB MS, calcd. for $C_{20}H_{29}N_6O_5$ (M+H+): 433.2199. Found: 433,2204.

N-Methyl-4[N-methyl-4-(succinamic acid)-pyrrole-2-carboxamide]-pyrrole-2-carboxamide-N,N-dimethylpropylamine (10b), 81%. ¹H NMR δ 9.91 (s, 1H), 9.85

(s, 1H), 8.07 (t, 1H), 7.18 (d, 1H), 7.14 (d, 1H), 6.86 (d, 1H), 6.81 (d, 1H), 3.81 (s, 3H), 3.79 (s, 3H), 3.18 (m, 2H), 2.45 (s, 4H), 2.15 (t, 2H), 2.15 (s, 6H), 1.61 (m, 2H); FAB MS, calcd. for $C_{21}H_{31}N_6O_5$ (M+H+): 447.2355. Found: 0.

N-Methyl-4-[N-methyl-4(fumaramic acid)-pyrrole-2-carboxamide]-pyrrole-2-carboxamide-N,N-dimethylpropylamine (10c), 83%. $^1$H NMR δ 10.38 (s, 1H), 9.92 (s, 1H), 8.06 (t, 1H), 7.28 (s, 1H), 7.18 (s, 1H), 6.94 (s, 1H), 6.84 (s, 2H), 6.69 (s, 1H), 3.83 (s, 3H), 3.80 (s, 3H), 3.2 (m, 2H), 2.50 (t, 2H), 2.38 (s, 6H), 1.7 (m, 2H); FAB MS, calcd. for $C_{21}H_{29}N_6O_5$ (M+H+): 445.2199. Found: 0.

Bis(netropsin)t-butylcarbamates (11a–c). A solution of 10a, 10b, or 10c in 1 mL DMF was treated with 2.0 equiv. of 1-HBT and 1.1–1.5 equiv. of 8, which had been hydrogenated for 48–60 h at 50 psi and RT using 5% Pd/C in DMF. This mixture was treated with 1.1 equiv. of DCC and stirred 24–48 h at RT. The mixture was filtered, the solvent distilled in vacuo, and the residue triturated with ether. Chromatography on silica gel using 1% NH₄Oh/MeOH eluent affored 11a–c as yellow to orange solids.

Bis(netropsin) malonamide-t-butylcarbamate (11a), 57%. $^1$H NMR δ 10.07 (s, 2H), 9.86 (s, 1H), 9.85 (s, 1H), 8.06 (t, 1H), 7.96 (t, 1H), 7.18 (s, 4H), 6.89 (m, 2H), 6.84 (d, 1H), 6.82 (d, 1H), 6.78 (t, 1H), 3.84 (s, 6H), 3.80 (s, 6H), 3.34 (s, 2H), 3.17 (m, 4H), 2.96 (m, 2H), 2.26 (t, 2H), 2.15 (s, 6H), 1.6 (m, 4H), 1.38 (s, 9H): FAB Ms calcd. for $C_{40}H_{57}N_{12}O_8$ (M+H+): 833,4422. Found: 833.4400.

Bis(netropsin) succinamide-t-butylcarbamate (11b), 57%. $^1$H NMR δ 9.88 (s, 2H), 9.85 (s, 1H), 9.84 (s, 1H), 8.05 (t, 1H), 7.95 (t, 1H), 7.17 (s, 2H), 7.15 (s, 2H), 6.85 (s, 2H), 6.84 (s, 1H), 6.81 (s, 1H), 6.79 (t, 1H), 3.82 (s, 6H), 3.79 (s, 6H), 3.17 (m, 4H), 2.95 (m, 2H), 2.56 (s, 4H), 2.23 (t, 2H), 2.13 (s, 6H), 1.59 (m, 4H), 1.38 (s, 9H); FAB MS, calcd. for $C_{41}H_{59}N_{12}O_8$ (M+H+): 847.4578. Found: 0.

Bis(netropsin) fumaramide-t-butylcarbamate (11c), 70%. $^1$H NMR δ 10.48 (s, 2H), 9.93 (s, 1H), 9.92 (s, 1H), 8.06 (t, 1H), 7.97 (t, 1H), 7.33 (s, 2H), 7.19 (d, 2H), 7.09 (s, 2H), 6.94 (s, 2H), 6.86 (s, 1H), 6.83 (d, 1H), 6.79 (t, 1H), 3.86 (s, 6H), 3.80 (s, 6H), 3.18 (m, 4H), 2.96 (m, 2H), 2.26 (t, 2H), 2.15 (s, 6H), 1.62 (m, 2H), 1.59 (m, 2H), 1.39 (s, 9H); FAB MS, calcd. for $C_{41}H_{57}N_{12}O_8$ (M+H+): 845,4421. Found: 0.

N-Methyl-4[N-methyl-4-(4-t-butylcarbamoyl-butyramide)pyrrole-2-carboxamide]-pyrrole-2-carboxylic acid (15). A solution of 2 (0.64 g, 2.2 mmol) and triethylamine (0.84 mL, 6.0 mmol) in 10 mL DMF was treated with 100 mg 5% Pd/C and hydrogenated at atmospheric pressure and RT for 20 h. This mixture was added to a stirred solution of the imidazolide of 6 (prepared by stirring 0.41 g, 2.0 mmol 6 with 0.36 g, 2.2 mmol CDI in 5 mL DMF for 2 h). After stirring at RT for 16 h, the reaction mixture was filtered, the solvent distilled in vacuo, and the residue triturated with ether. Chromatography on silica gel using 10% MeOH/CH₂Cl₂ followed by 33% MeOH/CH₂Cl₂ eluent afforded 0.93 g of brown solid, shown by NMR to be a 1.1 mixture of 15 and imidazole. Rechromatography using 15% MeOH/CH₂Cl₂ eluent afforded pure 15. $^1$H NMR δ 9.69 (br s, 2H), 7.20 (d, 1H), 7.08 (d, 1H), 6.79 (d, 1H), 6.76 (t, 1H), 6.70 (d, 1H), 3.85 (s, 3H), 3.83 (s, 3H), 2.92 (m, 2H), 2.22 (q, 2H), 1.67 (m, 2H), 1.39 (s, 9H); FAB MS, calcd. for $C_{21}H_{30}N_5O_5$ (M+H+): 432.2247. Found: 448.2185.

N-Methyl-4-[N-methyl-4-(4-t-butylcarbamoyl-butyramide)pyrrole-2-carboxamide]-pyrrole-2-carboxamideN,N-dimethylpropylamine (16b). 7 (0.41 g, 1.1 mmol) was hydrogenated at atmospheric pressure and RT for 20 h in 10 mL DMF using 35 mg 5% Pd/C. The mixture was then cooled in an ice/water bath and treated with 1-HBT (0.27 g, 2.0 mmol), and 6 (0.20 g, 1.0 mmol), DCC (0.23 g, 1.1 mmol) in 1 mL DMF was added. The cooling bath was removed and the mixture stirred at RT under argon for 20 h. The mixture was filtered, the solvent distilled in vacuo, and the residue triturated with ether. Chromatography on silica gel using 1% NH₄OH/MeOH eluent afforded 0.45 g (0.85 mmol, 85%) of 16b as a yellow solid. $^1$H NMR δ 9.84 (s, 1H), 9.78 (s, 1H), 8.06 (t, 1H), 7.17 (d, 1H), 7.15 (d, 1H), 6.85 (d, 1H), 6.81 (d, 1H), 6.8 (br s, 1H). 3.83 (s, 3H), 3.80 (s, 3H), 3.19 (m, 2H), 2.95 (m, 2H), 2.23 (m, 4H), 2.15 (s, 6H), 1.67 (m, 2H), 1.62 (m, 2H), 1.39 (s, 9H); FAB MS, calcd. for $C_{26}H_{42}N_7O_5$ (M+H+): 532.3247. Found: 532.3236.

N-Methyl-4-[N-methyl-4-(2-t-butylcarbamoylacetamide)pyrrole-2-carboxamide]-pyrrole-2-carboxamideN,N-dimethylpropylamine (16a), 85% from 7 and commercially available t-boc glycine using the procedure for 16b. $^1$H NMR δ 9.85 (s, 1H), 9.81 (s, 1H), 8.06 (t, 1H), 7.18 (d, 1H), 7.15 (d, 1H), 7.00 (t, 1H), 6.89 (d, 1H), 6.81 (s, 1H), 3.83 (s, 3H), 3.79 (s, 3H), 3.65 (d, 2H), 3.17 (m, 2H), 2.24 (t, 2H), 2.14 (s, 6H), 1.60 (m, 2H), 1.39 (s, 9H): FAB MS, calcd. for $C_{24}H_{38}N_7O_5$ (M+H+): 504.2934. Found: 0.

N-Methyl-4-[N-methyl-4-(4-aminobutyramide)-pyrrole-2carboxamide]-pyrrole-2-carboxamideN,N-dimethylpropylamine (17c). Compound 16b (0.30 g, 0.56 mmol) was dissolved in 4 mL CH₂Cl₂, cooled in an ice/water bath under argon, and treated with 1.5 mL trifluoroacetic acid (TFA). The mixture was removed from the cooling bath and stirred for 15 min. The product was precipitated with 15 mL ether and the supernatant discarded. The residue was dissolved in 10 mL 10% NH₄OH/MeOH, and then concentrated at reduced pressure. Chromatography on silica gel using the same solvent afforded 200 mg (0.46 mmol, 83%) of 17c as a yellow solid. $^1$H NMR δ 9.84 (s, 1H), 9.81 (s, 1H), 8.07 (t, 1H), 7.18 (d, 1H), 7.15 (d, 1H), 6.85 (d, 1H), 6.81 (d, 1H), 3.82 (s, 3H), 3.80 (s, 3H), 3.18 (m, 2H), 2.55 (t, 2H), 2.25 (m, 4H), 2.14 (s, 6H), 1.63 (m, 4H); FAB MS calcd. for $C_{21}H_{34}N_7O_3$ (M+H+): 432.2723. Found: 432.2713.

N-Methyl-4-[N-methyl-4-(2-aminoacetamide)-pyrrole-2carboxamide]-pyrrole-2-carboxamideN,N-dimethylpropylamine (17a), 83% from 16a using the procedure for 17c. $^1$H NMR δ 9.84 (s, 2H), 8.06 (t, 1H), 7.19 (s, 1H), 7.18 (s, 1H), 6.93 (s, 1H), 6.81 (s, 1H), 3.83 (s, 3H), 3.79 (s, 3H), 3.22 (s, 2H), 2.13 (s, 6H), 1.60 (m, 2H); FAB MS, calcd. for $C_{19}H_{30}N_7O_3$ (M+H+): 404.2410. Found: 0.

N-Methyl-4-[N-methyl-4-(2-cyanoacetamide)-pyrrole-2carboxamide]-pyrrole-2-carboxamide-N,N-dimethylpropylamine (18) was prepared from 7 and commercially available cyanoacetic acid in 79% yield using the procedure for 16b. $^1$H NMR δ 10.21 (s, 1H), 9.85 (s, 1H), 8.04 (t, 1H), 7.17 (d, 1H), 7.14 (d, 1H), 6.88 (d, 1H), 6.80 (d, 1H), 3.83 (s, 3H), 3.79 (s, 2H), 3.79 (s, 3H), 3.17 (m, 2H), 2.23 (t, 2H), 2.12 (s, 6H), 1.60 (m, 2H); FAB MS, calcd. for $C_{20}H_{28}N_7O_3$ (M+H+): 414.2254. Found: 414.2239.

N-Methyl-4-[N-methyl-4-(3-aminopropionamide)-pyrrole2-carboxamide]-pyrrole-2-carboxamide-N,N-dimethylpropylamine (17b). 18 (350 mg, 0.85 mmol) was dissolved in 7 mL acetic acid and treated with 70 mg of $PtO_2$. This mixture was hydrogenated at 50 psi and RT for 12 h, then filtered, evaporated, treated with 10 mL 10% $NH_4OH$/MeOH, and evaporated again. Chromatography on silica gel using 5% $NH_4OH$/MeOH eluent afforded 230 mg (0.55 mmol, 65%) of 17b as a yellow solid. $^1$H NMR δ 9.94 (s, 1H), 9.82 (s, 1H), 8.05 (t, 1H), 7.16 (d, 1H), 7.15 (d, 1H), 6.84 (d, 1H), 6.80 (d, 1H), 3.81 (s, 3H), 3.78 (s, 3H), 3.17 (m, 2H), 2.81 (t, 2H), 2.32 (t, 2H), 2.22 (t, 2H), 2.12 (s, 6H), 1.59 (m, 2H): FAB MS, calcd. for $C_{20}H_{32}N_7O_3$ (M+H+): 418.2567. Found: 418.2590.

Bis(netropsin)-t-butylcarbamates (11d–f). A solution of 17a, 17b, or 17c in DMF was treated with 2.0 equiv. of 1-HBT, 1.1 equiv. of 15, and then 1.2 equiv. of DCC in 1 mL DMF. After stirring 24 h at RT, the mixture was filtered, the solvent distilled in vacuo, and the residue triturated with ether. Chromatography on silica gel using 1% $NH_4OH$/MeOH eluent afforded 11d–f as yellow solids.

Bis(netropsin)-2-amidoacetamide-t-butylcarbamate (11d), 68%. $^1$H NMR δ 9.90 (s, 1H), 9.87 (s, 1H), 9.85 (s, 1H), 9.79 (s, 1H), 8.28 (t, 1H), 8.06 (t, 1H), 7.24 (s, 1H), 7.18 (s, 1H), 7.17 (d, 1H), 7.15 (s, 1H), 6.94 (s, 1H), 6.91 (s, 1H), 6.87 (s, 1H), 6.83 (br s, 1H), 6.81 (d, 1H), 3.90 (d, 2H), 3.83 (s, 6H), 3.81 (s, 3H), 3.79 (s, 3H), 3.18 (m, 2H), 2.94 (m, 2H), 2.24 (m, 4H), 2.13 (s, 6H), 1.66 (m, 2H), 1.60 (m, 2H), 1.38 (s, 9H); FAB MS, calcd. for $C_{40}H_{57}N_{12}O_8$ (M+H+): 833.4421. Found: 0.

Bis(netropsin)-3-amidopropionamide-t-butylcarbamate (11e), 64%. $^1$H NMR δ 9.89 (s, 1H), 9.85 (s, 2H), 9.77 (s, 1H), 8.05 (m, 2H), 7.17 (m, 3H), 7.13 (d, 1H), 6.84 (m, 2H), 6.82 (s, 1H), 6.80 (d, 1H), 3.81 (s, 3H), 3.80 (s, 6H), 3.78 (s, 3H), 3.43 (m, 2H), 3.17 (m, 2H), 2.92 (m, 2H), 2.50 (t, 2H), 2.23 (t, 2H), 2.20 (t, 2H), 2.12 (s, 6H), 1.65 (m, 2H), 1.59 (m, 2H), 1.36 (s, 9H); FAB MS, calcd. for $C_{41}H_{59}N_{12}O_8$ (M+H+): 847.4578. Found: 847.4584.

Bis(netropsin)-4-amidobutyramide-t-butylcarbamate(11f), 69%. $^1$H NMR δ 9.85 (2s, 2H), 9.84 (s, 1H), 9.78 (s, 1H), 8.05 (m, 2H), 7.17 (s, 3H), 7.15 (s, 1H), 6.89 (s, 1H), 6.86 (s, 1H), 6.83 (t, 1H), 6.81 (s, 1H), 3.83 (s, 6H), 3.81 (s, 3H), 3.80 (s, 3H), 3.25 (m, 4H), 2.95 (m, 2H), 2.25 (m, 6H), 2.15 (s, 6H), 1.79 (m, 2H), 1.67 (m, 2H), 1.61 (m, 2H), 1.38 (s, 9H); FAB MS, calcd. for $C_{42}H_{61}N_{12}O_8$ (M+H+): 861.4735.

N-Methyl-4[N-methyl-4-(4-N,N-dimethylaminobutyramide)pyrrole-2-carboxamide]-pyrrole-2-carboxylic acid, methyl ester (19). A solution of 2, methyl ester$^1$ (0.306 g, 1.0 mmol) in 15 mL DMF was treated with 33 mg 5% Pd/C and hydrogenated at atmospheric pressure and RT for 20 h. This mixture was filtered into a stirred solution of the imidazolide of N,N-dimethylaminobutyric acid (prepared by stirring dimethylaminobutyric acid, hydrochloride (0.34 g, 1.1 mmol) with CDI (0.36 g, 2.2 mmol) in 30 mL DMF for 2 h). After stirring at RT for 23 h the solvent was distilled in vacuo and the residue triturated with ether. Chromatography using 2.5% $NH_4OH$/MeOH afforded 0g of 19 as a tan solid. $^1$H NMR δ 9.88 (s, 1H), 9.81 (s, 1H), 7.45 (d, 1H), 7.15 (d, 1H), 6.88 (d, 1H), 6.86 (d, 1H), 3.83 (d, 6H), 3.73 (s, 3H), 2.20 (t, 2H), 2.15 (t, 2H), 2.13 (s, 6H), 1.69 (m, 2H).

N-Methyl-4-[N-methyl-4-(4-N,N-dimethylaminobutyramide)pyrrole-2-carboxamide]-pyrrole-2-carboxylic acid (20). A solution of 19 (0.55 g, 1.4 mmol) and NaOH (0.18 g, 4.55 mmol) in 20 mL 1:1 $H_2O$:EtOH was refluxed for 3 h and then allowed to cool to RT. 1N HCl (4.7 mL) was slowly added to the stirred solution which was then frozen at 78K and lyophilized to give a tan solid. Chromatography on silica gel using 3% $NH_4OH$/MeOH eluent afforded 0g of 20. $^1$H NMR δ 10.13 (s, 1H), 9.94 (s, 1H), 7.42 (d, 1H), 7.18 (d, 1H), 6.90 (d, 1H), 6.85 (d, 1H), 3.82 (d, 6H), 3.04 (m, 2H), 2.73 (d, 6H), 2.37 (t, 2H), 1.97 (m, 2H).

N,N-Dimethylamino-t-butylcarbamates (23a–c). A solution of 20 in DMF was treated with 2.0 equiv. of 1-HBT, 1.0 equiv. of 3, 4 or 5 in 1 mL DMF and then 1.1 equiv. of DCC. After stirring 24 h at RT the mixture was filtered, the solvent distilled in vacuo, and the residue triturated with ether. Chromatography on silica gel using 3% $NH_4OH$/MeOH eluent afforded 23a–c as tan solids.

N-Methyl-4-[N-methyl-4-(4-N,N-dimethylaminobutyramide)pyrrole-2-carboxamide]-pyrrole-2-carboxamide-ethyl-t-butylcarbamate (23a), 0%. $^1$H NMR δ 9.84 (s, 1H), 9.79 (s, 1H), 7.95 (t, 1H), 7.17 (d, 1H), 7.15 (d, 1H), 6.85 (br s, 3H), 3.80 (d, 6H), 3.20 (q, 2H), 3.05 (q, 2H), 2.24 (m, 4H), 2.14 (m, 6H), 1.69 (p, 2H), 1.38 (s. 9H).

N-Methyl-4-[N-methyl-4-(4-N,N-dimethylaminobutyramidepyrrole-2-carboxamide]-pyrrole-2-carboxamide-propyl-t-butylcarbamate (23b), 0%. $^1$H NMR δ 9.85 (s, 1H), 9.80 (s, 1H), 7.96 (t, 1H), 7.17 (d, 1H), 7.15 (d, 1H), 6.84 (d, 2H), 6.79 (t, 1H), 3.80 (d, 6H), 3.16 (m, 2H), 2.95 (m, 2H), 2.24 (t, 2H), 2.20 (t, 2H), 1.68 (m, 2H), 1.58 (m, 2H), 1.38 (s, 9H).

N-Methyl-4-[N-methyl-4-(4-N,N-dimethylaminobutyramide)pyrrole-2-carboxamide]-pyrrole-2-carboxamide-butyl-t-butylcarbamate (23c) 0%. $^1$H NMR δ 9.83 (s, 1H), 9.80 (s, 1H), 7.98 (t, 1H), 7.16 (d, 1H), 7.15 (d, 1H), 6.84 (m, 2H), 6.79 (m, 1H), 3.80 (d, 6H), 3.14 (q. 2H), 2.92 (q, 2H), 2.25 (m, 4H), 2.16 (s. 6H), 1.70 (p. 2H), 1.41 (m, 4H), 1.37 (s, 9H).

N,N-Dimethylamino amines (24a–c). A solution of 23a, b, or c (100 mg) was dissolved in 1 mL $CH_2Cl_2$, cooled in an ice/water bath and stirred under argon. TFA (0.5 mL) was added and the mixture removed from the cooling bath and stirred at RT for 15 min. The product was precipitated by adding 3 volumes of ether.

The supernatant was then discarded, and the residue was dissolved in 10 mL 3% NH4OH/MeOH and concentrated under reduced pressure. Chromatography on silica gel usign 10% NH4OH/MeOH eluent afforded 24a–c as yellow solids.

N-Methyl-4-[N-methyl-4-(4-N,N-dimethylaminobutyramide)pyrrole-2-carboxamide]-pyrrole-2-carboxamide-ethylamine (24a), 81%. $^1$H NMR none available at present.

N-Methyl-4-[N-methyl-4-(4-N,N-dimethylaminobutyramide)-pyrrole-2-carboxamide]-2-pyrrole-2-carboxamide-propylamine (24b), 68%. $^1$H NMR δ 9.84 (s, 1H), 9.80 (s, 1H), 8.31 (t, 0.5H), 8.08 (m, 0.5H), 7.17 (s, 1H), 7.15 (s, 1H), 6.85 (s, 2H), 3.81 (d, 6H), 3.22 (m, 2H), 2.97 (q, 1H), 2.63 (t, 1H), 2.24 (t, 2H), 2.20 (t, 2H), 2.11 (s, 6H), 1.68 (p, 2H), 1.60 (m, 2H).

N-Methyl-4-[N-methyl-4-(4-N,N-demethylaminoburyramide)-pyrrole-2-carboxamide]-2-pyrrole-2-carboxamide-butylamine (24c), 68%. $^1$H NMR none available at present.

Bis(netropsin)-t-butylcarbamates (11g–i). A solution of 24a, b or c in DMF was treated with 2 equiv. of 1-HBT, 1.1 equiv. of 15, and then 1.1 equiv. of DCC. After stirring 24 h at RT, the mixture was filtered, the solvent distilled in vacuo, and the residue triturated with ether. Chromatography on silica gel using 1% NH4OH/MeOH eluent afforded 11g–i as tan solids.

Bis(netropsin)-1,2-diamidoethane-t-butylcarbamate (11g), 61%. $^1$H NMR δ 9.86 (s, 2H), 9.79 (s, 1H), 9.78 (s, 1H), 8.09 (br s, 2H), 7.19 (d, 2H), 7.15 (s, 2H), 6.87 (d, 2H), 6.85 (s, 2H), 6.84 (t, 1H), 3.82 (s, 12H), 3.36 (s, 4H), 2.94 (q, 2H), 2.20 (m, 6H), 2.11 (s, 6H), 1.68 (m, 4H), 1.38 (s, 9H).

Bis(netropsin)-1,3-diamidopropane-t-butylcarbamate (11h), 86%. $^1$H NMR δ 9.86 (s, 2H), 9.81 (s, 1H), 9.79 (s, 1H), 8.04 (t, 2H), 7.19 (s, 2H), 7.15 (s, 2H), 6.86 (s, 2H), 6.85 (s, 2H), 6.84 (t, 1H), 3.81 (d, 12H), 3.22 (m, 4H), 2.94 (q, 2H), 2.21 (m, 6H), 1.70 (m, 6H), 1.38 (s, 9H).

Bis(netropsin)-1,4-diamidobutane-t-butylcarbamate(11i), 90%. $^1$H NMR δ 9.83 (s, 2H), 9.79 (s, 1H), 9.78 (s, 1H), 8.01 (t, 2H), 7.16 (d, 2H), 7.15 (s, 2H), 6.84 (s, 4H), 6.83 (t, 1H), 3.81 (d, 12H), 3.19 (m, 4H), 2.94 (q, 2H), 2.21 (m, 6H), 2.11 (br s, 6H), 1.68 (m, 4H), 1.50 (s, 4H), 1.38 (s, 9H). Found: 861.4706.

Bis(netropsin)s (12a-1). A solution or slurry of 11a–i in CH2Cl2 (0.1M) was cooled in an ice/water bath and stirred under argon. One-half volume of TFA was added and the mixture removed from the cooling bath and stirred at RT for 15 min. The product was precipitated by adding 2–3 volumes of ether, and the supernatant was discarded. The residue was dissolved in 10 mL of 10% NH4OH/MeOH, and concentrated under reduced pressure. Chromatography on silica gel using the same solvent afforded the diamines 12a–i as yellow solids.

Bis(netropsin) malonamide (12a), 75%. $^1$H NMR δ 10.08 (s, 2H), 9.86 (s, 2H), 8.06 (m, 2H), 7.18 (s, 4H), 6.90 (s, 2H), 6.84 (s, 1H), 6.81 (s, 1H), 3.84 (s, 6H), 3.80 (s, 6H), 3.34 (s, 2H), 3.21 (m, 4H), 2.61 (t, 2H), 2.24 (t, 2H), 2.13 (s, 6H), 1.59 (m, 4H); FAB MS, calcd. for $C_{35}H_{49}N_{12}O_6$ (M+H+): 733.3898. Found 733.3865.

Bis(netropsin)succinamide (12b), 79%. $^1$H NMR δ 9.88 (s, 2H), 9.83 (s, 2H), 8.04 (t, 2H), 7.17 (s, 2H), 7.15 (d, 2H), 6.86 (d, 2H), 6.83 (d, 1H), 6.81 (d, 1H), 3.82 (s, 6H), 3.79 (s, 6H), 3.19 (m, 4H), 2.58 (t, 2H), 2.56 (s, 4H), 2.23 (t, 2H), 2.13 (s, 6H), 1.60 (m, 2H), 1.55 (m, 2H); FAB MS, calcd. $C_{36}H_{51}N_{12}O_6$(M+H+): 747.4054. Found: 0.

Bis(netropsin)fumaramide (12c), 84%. $^1$H NMR δ 10.49 (s, 2H), 9.92 (s, 2H), 8.06 (m, 2H), 7.32 (s, 2H), 7.17 (s, 2H), 7.08 (s, 2H), 6.93 (s, 2H), 6.87 (s, 1H), 6.81 (s, 1H), 3.85 (s, 6H), 3.79 (s, 6H), 3.16 (m, 4H), 2.66 (br s, 2H), 2.22 (t, 2H), 2.12 (s, 6H). 1.60 (m, 4H); FAB MS, calcd. for $C_{36}H_{49}N_{12}O_6$ (M+H+): 745.3897. Found: 0.

Bis(netropsin)-2-amidoacetamide (12d), 71%. $^1$H NMR δ 9.90 (s, 1H), 9.88 (s, 1H), 9.85 (s, 1H), 9.80 (s, 1H), 8.28 (t, 1H), 8.06 (t, 1H), 7.24 (s, 1H), 7.18 (s, 1H), 7.18 (s, 1H), 7.17 (d, 1H), 7.15 (d, 1H), 6.94 (s, 1H), 6.91 (s, 1H), 6.87 (s, 1H), 6.81 (s, 1H), 3.90 (d, 2H), 3.83 (s, 6H), 3.81 (s, 3H), 3.79 (s, 3H), 3.18 (m, 2H), 2.54 (t, 2H), 2.26 (t, 2H), 2.23 (t, 2H), 2.13 (s, 6H), 1.61 (m, 4H); FAB MS, calcd. for $C_{35}H_{49}N_{12}O_6$ (M+H+): 733.3897. Found: 0.

Bis(netropsin)-3-amidopropionamide (12e), 80%. $^1$H NMR δ 9.89 (s, 1H), 9.84 (s, 2H), 9.80 (s, 1H), 8.05 (m, 2H), 7.17 (m, 3H), 7.14 (d, 1H), 6.84 (m, 2H), 6.82 (s, 1H), 6.79 (d, 1H), 3.81 (s, 3H), 3.80 (s, 6H), 3.78 (s, 3H), 3.43 (m, 2H), 3.17 (m, 2H), 2.56 (t, 2H), 2.50 (t, 2H), 2.25 (t, 2H), 2.22 (t, 2H), 2.12 (s, 6H), 1.64 (m, 2H), 1.59 (m, 2H); FAB MS, calcd. for $C_{36}H_{51}N_{12}O_6$ (M+H+): 747.4054. Found: 747.4044.

Bis(netropsin)-4-amidobutyramide (12f), 93%. $^1$H NMR δ 9.84 (4 s, 4H), 8.05 (m, 2H), 7.17 (s, 4H), 6.89 (s, 1H), 6.87 (s, 1H), 6.85 (s, 1H), 6.81 (s, 1H), 3.82 (s, 6H), 3.80 (s, 3H), 3.79 (s, 3H), 3.2 (m. 4H), 2.28 (m, 4H), 2.24 (t, 2H), 2.13 (s, 6H), 1.79 (m, 2H), 1.7 (br s, 2H), 1.62 (m, 2H). That the resonance expected at δ 2.6 (H2N-CH2-) was not observed and the methylene signal at δ 1.7 was so broad, was odd but reproducible; at first this was taken to mean that one 4-aminobutyric acid unit had been lost during the deprotection. However, subsequent transformation to 22f revealed this unit again in the NMR. FAB MS, calcd.

Bis(netropsin)-1,2-diamidoethane (12g), 86%. $^1$H NMR δ 9.86 (s, 3H), 9.80 (s, 1H), 8.09 (br s, 2H), 7.19 (s, 2H), 6.86 (s, 2H), 6.85 (s, 2H), 3.81 (s, 12H), 3.35 (s, 4H), 2.54 (t, 2H), 2.21 (m, 6H), 2.11 (s, 6H), 1.66 (m, 4H).

Bis(netropsin)-1,3-diamidoprorane (12h), 58%. $^1$H NMR δ 9.85 (s, 2H), 9.79 (s, 2H), 8.03 (t, 2H), 7.19 (s, 2H), 7.15 (s, 2H), 6.86 (s, 2H), 6.85 (s, 2H), 3.82 (d, 12H), 3.22 (m, 4H), 2.55 (t, 2H), 2.21 (m, 6H), 2.11 (s, 6H), 1.68 (m, 6H).

Bis(netropsin)-1,4-diaminobutane (12i), 69%. $^1$H NMR δ 9.83 (s, 2H), 9.79 (s, 2H), 8.01 (t, 2H), 7.16 (s, 2H), 7.15 (s, 2H), 6.84, 3.80 (d, 12H), (s, 4H), 3.18 (m, 4H), 2.55 (t, 2H), 2.21 (m, 6H), 2.11 (s, 6H), 2.11 (s, 6H), 1.66 (m, 4H), 1.50 (br s, 4H). for $C_{37}H_{53}N_{12}O_6$ (M+H+): 761.4211. Found: 761.4224.

EDTA, triethyl ester (21) was prepared following the published procedure.

Bis(netropsin)-EDTA, triethyl esters (22a–i). A solution of 21 in DMF (0.25M) was activated with 1.1 equiv. of CDI and stirred for 2 h at RT under argon. The mixture was then taken up in a syringe and added to 0.25-0.50 equiv. of 12 (dissolved in 1 mL DMF). After stirring 24 h at RT under argon, the mixture was evaporated, and the triturated with ether. Chromatography on silica gel using 1% NH$_4$OH/MeOH eluent afforded 22a-i as light yellow solids.

Bis(netropsin)malonamide-EDTA, triethyl ester (22a), 99%. $^1$H NMR δ 10.06 (s, 2H), 9.86 (s, 1H), 9.84 (s, 1H), 8.04 (t, 1H), 8.03 (t, 1H), 7.97 (t, 1H), 7.18 (m, 4H), 6.90 (m, 2H), 6.85 (d, 1H), 6.82 (d, 1H), 4.07 (m, 6H), 3.84 (s, 6H), 3.80 (s, 6H), 3.61-3.47 (series of singlets, 8H), 3.34 (s, 2H), 3.19 (m, 6H), 2.72 (m, 4H), 2.30 (t, 2H), 2.18 (s, 6H), 1.62 (m, 4H), 1.19 (m, 9H); FAB MS, calcd. for $C_{51}H_{75}N_{14}O_{13}$ (M+H+): 1091.5637. Found: 0.

Bis(netropsin) succinamide-EDTA, triethyl estewr (22b), 81%. $^1$H NMR δ 9.89 (s, 2H), 9.86 (s, 1H), 9.84 (s, 1H), 8.05 (m, 2H), 7.99 (m, 1H), 7.17 (s, 2H), 7.15 (s, 2H), 6.86 (s, 3H), 6.81 (s, 1H), 4.06 (m, 6H), 3.82 (s, 6H), 3.80 (s, 6H), 3.60-3.47 (series of singlets, 8H), 3.18 (m, 6H), 2.73 (m, 4H), 2.56 (br s, 4H), 2.24 (t, 2H), 2.14 (s, 6H), 1.60 (m, 4H), 1.18 (m, 9H); FAB MS, calcd. for $C_{52}H_{77}N_{14}O_{13}$(M+H+): 1105.5795. Found: 1105.5795.

Bis(netropsin) fumaramide-EDTA, triethyl ester (22c), 42%. $^1$H NMR δ 10.49 (s, 2H), 9.93 (m, 2H), 8.06 (m, 2H), 8.00 (t, 1H), 7.33 (s, 2H), 7.19 (s, 2H), 7.09 (s, 2H), 6.94 (s, 2H), 6.86 (d, 1H), 6.83 (d, 1H), 4.07 (m, 6H), 3.87 (s, 6H), 3.81 (s, 6H), 3.61-3.48 (series of singlets, 8H), 3.2 (m, 6H), 2.72 (m, 4H), 2.25 (t, 2H), 2.15 (s, 6H), 1.62 (m, 4H), 1.18 (m, 9H); FAB MS, calcd. for $C_{52}H_{75}N_{14}O_{13}$(M+H+): 1103.5638 Found: 1103.5640.

Bis(netropsin)-2-amidoacetamide-EDTA, triethyl ester (22d), 56%. $^1$H NMR δ 9.90 (s, 1H), 9.87 (s, 1H), 9.85 (s, 1H), 9.80 (s, 1H), 8.28 (t, 1H), 8.05 (t, 1H), 8.01 (t, 1H), 7.24 (s, 1H), 7.17 (s, 1H), 7.16 (s, 2H), 6.94 (s, 1H), 6.91 (s, 1H), 6.87 (s, 1H), 4.06 (m, 6H), 3.90 (d, 2H), 3.83 (s, 6H), 3.81 (s, 3H), 3.79 (s, 3H), 3.61-3.46 (series of singlets, 8H), 3.18 (m, 2H), 3.12 (m, 2H), 2.71 (m, 4H), 2.23 (m, 4H), 2.13 (s, 6H), 1.71 (m, 2H), 1.60 (m, 2H), 1.17 (m, 9H); FAB MS, calcd. for $C_{51}H_{75}N_{14}O_{13}$ (M+H+): 1091.5637. Found: 0.

Bis(netropsin)-3-amidopropionamide-EDTA, triethyl ester (22e), 67%. $^1$H NMR δ 9.90 (s, 1H), 9.85 (s, 1H), 9.80 (s, 1H), 8.06 (m, 2H), 8.00 (t, 1H), 7.18 (m, 3H), 7.15 (d, 1H), 6.86 (d, 1H), 6.84 (d, 1H), 6.83 (d, 1H), 6.80 (d, 1H), 4.07 (m, 6H), 3.82 (s, 3H), 3.81 (s, 6H), 3.79 (s, 3H), 3.60-3.46 (series of singlets, 8H), 3.31 (m, 2H), 3.16 (m, 4H), 3.12 (m, 2H), 2.71 (m, 4H), 2.50 (m, 2H), 2.23 (m, 4H), 2.13 (s, 6H), 1.70 (m, 2H), 1.60 (m, 2H), 1.17 (m, 9H); FAB MS, calcd. for $C_{52}H_{77}N_{14}O_{13}$ (M+H+): 1105.5795. Found: 1105.5739.

Bis(netropsin)-4-amidobutyramide-EDTA, triethyl ester (22f), 54%. $^1$H NMR δ 9.86 (s, 1H), 9.85 (s, 1H), 9.84 (s, 1H), 9.81 (s, 1H), 8.06 (m, 2H), 8.02 (m, 2H), 7.17 (m, 3H), 7.15 (d, 1H), 6.89 (d, 1H), 6.86 (m, 2H), 6.81 (d, 1H), 4.07 (m, 6H), 3.82 (s, 6H), 3.80 (s, 3H), 3.79 (s, 3H), 3.61-3.46 (series of singlets, 8H), 3.19 (m, 6H), 2.71 (m, 4H), 2.26 (m, 6H), 2.14 (s, 6H), 1.79 (m, 2H), 1.71 (m, 2H), 1.61 (m, 2H), 1.17 (m, 9H); FAB MS, calcd. for $C_{53}H_{79}N_{14}O_{13}$(M+H+):

Bis(etropsin)-1,2-diamidoethane-EDTA, triethyl ester (22g), 95%. $^1$H NMR none available at present.

Bis(netropsin)-1,3-diamidopropane-EDTA, triethyl ester (22h), 73%. $^1$H NMR none available at present.

Bis(netropsin)-1,4-diamidobutane-EDTA, triethyl ester (22i), 89%. $^1$H NMR none available at present. 1119.5951. Found: 1119.5890.

Bis(netropsin)-EDTA compounds (1a-i). A solution of 22 in 2:1 MeOH/H$_2$O (0.5 M) was treated with 10 equiv. of LiOH and stirred overnight at RT. The mixture was evaporated and the residue chromatographed on silica gel using 1-2% NH$_4$OH/MeOH eluent to afford 1a-i as light yellow solids.

Bis(netropsin)malonamide-EDTA (1a), 90%. $^1$H NMR (Me$_2$SO-d$_6$+TFA) δ10.08 (s, 2H), 9.87 (s, 1H), 9.86 (s, 1H), 8.37 (t, 1H), 8.15 (t, 1H), 8.01 (t, 1H), 7.19 (s, 2H), 7.17 (d, 1H), 7.16 (d, 1H), 6.93 (d, 1H), 6.90 (m, 3H)), 4.07 (s, 2H), 3.91 (s, 2H), 3.84 (s, 6H), 3.82 (s, 3H), 3.80 (s, 3H), 3.74, (s, 4H), 3.35 (s, 2H), 3.30 (m, 2H), 3.24 (m, 8H), 3.07 (m, 2H), 2.79 (d, 6H), 1.84 (m, 2H), 1.66 (m, 2H); FAB MS, calcd. for $C_{45}H_{63}N_{14}O_{13}$(M+H+): 1007.4699. Found: 1007.4660; UV(H$_2$O) λ$_{max}$296,241 nm.

Bis(netropsin) succinamide-EDTA (1b), 87%. $^1$H NMR (Me$_2$SO-d$_6$+TFA) δ9.90 (s, 2H), 9.87 (s, 1H), 9.85 (s, 1H), 8.40 (t, 1H), 8.16 (br s, 1H)), 8.02 (br s, 1H), 7.16 (s, 4H), 6.96 (s, 1H), 6.91 (s, 1H), 6.89 (s, 2H), 4.11 (s, 2H), 3.95 (s, 2H), 3.84 (s, 6H), 3.83 (s, 3H), 3.82 (s, 3H), 3.81 (s, 4H), 3.37 (br s, 2H), 3.25 (m, 8H), 3.10 (br s, 2H), 2.81 (d, 6H), 2.59 (s, 4H), 1.86 (m, 2H), 1.68 (m, 2H); FAB MS, calcd. for $C_{46}H_{64}N_{14}O_{13}$ (M+K+): 1021.4856. Found: O. UV(H$_2$O) λ$_{max}$297,237 nm.

Bis(netropsin)fumaramide-EDTA (1c), 100%. $^1$H NMR (Me$_2$SO-d$_6$+TFA) δ8.41 (br s, 1H), 8.19 (br s, 1H), 8.03 (br s, 1H), 7.35 (s, 2H), 7.19 (s, 2H), 7.12 (s, 2H), 7.01 (s, 1H), 6.97 (s, 2H), 6.93 (s, 1H), 4.11 (s, 2H), 3.97 (s, 2H), 3.95 (s, 2H), 3.87 (s, 6H), 3.84 (s, 3H), 3.83 (s, 3H), 3.82 (s, 2H), 3.38 (br s, 2H), 3.26 (m, 8H), 3.10 (br s, 2H), 2.82 (d, 6H), 1.87 (m, 2H), 1.68 (m, 2H); FAB MS, calcd. for $C_{46}H_{63}N_{14}O_{13}$ (M+H+): 1019.4618. Found: O; UV(H$_2$O) λ$_{max}$301,239 nm.

Bis(netropsin)-2-amidoacetamide-EDTA (1d), 72%. $^1$H NMR (Me$_2$SO-d$_6$+TFA) δ9.92 (s, 1H), 9.90 (s, 1H), 9.89 (s, 1H), 9.84 (s, 1H), 8.44 (t, 1H), 8.30 (br s, 1H), 8.17 (br s, 1H), 7.25 (s, 1H), 7.18 (s, 3H), 6.97 (s, 1H), 6.94 (s, 2H), 6.90 (s, 1H), 4.08 (s, 2H), 3.93 (s, 4H), 3.85 (s, 6H), 3.83 (s, 6H), 3.78 (s, 4H), 3.33 (br s, 2H), 3.26 (m, 2H), 3.21 (m, 4H), 3.09 (m, 2H), 2.80 (d, 6H), 2.30 (t, 2H), 1.85 (m, 2H), 1.76 (m, 2H); FAB MS, calcd. for $C_{45}H_{63}N_{14}O_{13}$ (M+H+): 1007.4699. Found: O. UV(H$_2$O) λ$_{max}$298,237 nm.

Bis(netropsin)-3-amidopropionamide-EDTA (1e), 100%. $^1$H NMR (Me$_2$SO-d$_6$ +TFA) δ9.93 (s, 1H), 9.89 (s, 1H), 9.86 (s, 1H), 9.84 (s, 1H), 8.44 (t, 1H), 8.17 (t, 1H), 8.08 (br s, 1H), 7.19 (s, 2H), 7.18 (d, 1H), 7.16 (s, 1H), 6.93 (d, 1H), 6.89 (d, 1H), 6.87 (d, 1H), 6.86 (s, 1H), 4.08 (s, 2H), 3.92 (s, 2H), 3.84 (s, 3H), 3.83 (s, 3H), 3.83 (s, 3H), 3.82 (s, 3H), 3.77 (s, 4H), 3.47 (m, 2H), 3.31 (m, 2H), 3.273.15 (m, 6H), 3.09 (m, 2H), 2.80 (d, 6H), 2.54 (t, 2H), 2.29 (t, 2H), 1.86 (m, 2H), 1.75 (m, 2H); FAB MS, calcd. for $C_{46}H_{65}N_{14}O_{13}$ (M+H+): 1021.4830. Found: 0; UV(H$_2$O) $\lambda_{max}$ 300, 236 nm.

Bis(netropsin)-4-amidobutyramide-EDTA (1f), 79%. $^1$H NMR (Me$_2$SO-d$_6$+TFA) $\delta$ 9.89 (s, 1H), 9.86 (s, 2H), 9.84 (s, 1H), 8.45 (t, 1H), 8.18 (t, 1H), 8.07 (br s, 1H), 7.18 (s, 4H), 6.95 (s, 1H), 6.92 (s, 1H), 6.89 (s, 2H), 4.10 (s, 2H), 3.94 (s, 2H), 3.84 (s, 6H), 3.83 (s, 6H), 3.79 (s, 4H), 3.35 (m, 2H), 3.24 (m, 8H), 3.10 (m, 2H), 2.81 (d, 6H), 2.30 (m, 4H), 1.82 (m, 4H), 1.77 (m, 2H); FAB MS, calcd. for $C_{47}H_{67}N_{14}O_{13}$ (M+H+): 1035.5054. Found: 1035.5036; UV(H$_2$O) $\lambda_{max}$ 301, 235 nm.

Bis(netropsin)-1,2,-diamidoethane-EDTA (1g), 87%. $^1$H NMR (Me$_2$SO-d$_6$+TFA) $\delta$ 9.95 (s, 1H), 9.88 (s, 1H), 9.87 (s, 1H), 9.83 (s, 1H), 9.48 (br s, 1H), 8.42 (t, 1H), 8.11 (br s, 2H), 7.19 (s, 3H), 7.16 (s, 1H), 6.88 (s, 2H), 6.86 (s, 2H), 4.08 (s, 2H), 3.92 (s, 2H), 3.83 (s, 12H), 3.76 (s, 4H), 3.33 (m, 6H), 3.18 (m, 4H), 3.07 (m, 2H), 2.80 (d, 6H), 2.36 (t, 2H), 2.28 (t, 2H), 1.91 (m, 2H), 1.78 (m, 2H).

Bis(netropsin)-1,3-diamidopropane-EDTA (1h), 56%. $^1$H NMR (Me$_2$SO-d$_6$+TFA) $\delta$ 9.95 (s, 1H), 9.88 (s, 1H), 9.87 (s, 1H), 9.83 (s, 1H), 9.49 (br s, 1H), 8.42 (t, 1H), 8.04 (br s, 2H), 7.19 (s, 3H), 7.16 (s, 1H), 6.89 (s, 2H), 6.87 (s, 2H), 4.08 (s, 2H), 3.92 (s, 2H), 3.82–3.84 (series of singlets, 12H), 3.77 (s, 4H), 3.32 (m, 2H), 3.20 (m, 8H), 3.11 (m, 2H), 2.81 (d, 6H), 2.36 (t, 2H), 2.29 (t, 2H), 1.92 (m, 2H), 1.75 (m, 2H), 1.69 (m, 2H).

Bis(netropsin)-1,4-diamidobutane-EDTA (1i), 77%. $^1$H NMR (Me$_2$SO-d$_6$+TFA) $\delta$ 9.96 (s, 1H), 9.86 (br s, 2H), 9.83 (s, 1H), 9.49 (br s, 1H), 8.45 (t, 1H), 8.04 (br s, 2H), 7.19 (m, 4H), 6.88 (s, 4H), 4.10 (s, 2H), 3.95 (s, 2H), 3.82–3.85 (series of singlets, 16H), 3.37 (m, 2H), 3.21 (m, 8H), 3.11 (m, 2H), 2.82 (d, 6H), 2.37 (t, 2H), 2.30 (t, 2H), 1.94 (m, 2H), 1.77 (m, 2H), 1.53 (br s, 4H).

Cleavage of End-Labeled DNA Restriction Fragments. General. Doubly distilled water was used for all aqueous reactions and dilutions. Plasmid pBR322 DNA was grown in *E. coli* (strain HB 101), and isolated as previously described. Calf thymus (CT) DNA was purchased from sigma and then sonicated, deproteinized, and dialyzed. Enzymes were purchased from Boehringer Mannheim or New England Biolabs.

Preparation of specifically end-labeled DNA restriction fragments began by cleaving superhelical pBR322 DNA with restriction endonuclease EcoR1. Linearized pBR322 was labeled on the 3' ends using 5'-[$\alpha$-$^{32}$P]dATP(Amersham, 3000 Ci/mmol) in the presence of the large (Klenow) fragment of DNA polymerase 1. This procedure also included dTTP, dATP, dCTP, and dGTP, which were purchased from Pharmacia as 100 mM solutions. Removal of 5'-phosphate groups from linearized pBR322 with calf alkaline phosphatase followed by treatment with 5'-[$\lambda$-$^{32}$P]dATP (New England Nuclear, 7000 Ci/mmol) in the presence of polynucleotide kinase afforded 5'-end-labeled DNA. Digestion of 3'-and 5'-end-labeled DNA with restriction endonuclease Rsal yielded 3'-and 5'-end-labeled restriction fragments 167 and 517 nucleotides in length. These were isolated by preparative gel electrophoresis on a 2 mm thick, 5% 1:30 crosslinked polyacrylamide gel. The bands of DNA were visualized by autoradiography, and were excised from the gel. The fragments were eluted into buffer (500 mM NH$_4$OAc, 10 mM MgCl$_2$, 1 mM EDTA, 0.25% SDS), microfiltered, extracted with phenol, concentrated by extraction with dry butanol, and ethanol precipitated several times before use.

DNA cleavage reactions were run in a total volume of 15 $\mu$L. For each reaction, 9 $\mu$L of a solution containing >600 cpm of $^{32}$P end-labeled restriction fragment and CT DNA (167 $\mu$M in base pairs, bp) in 66.7 mM Tris base/8.3 mM NaOAc buffer (pH 7.6) was treated with 3 $\mu$L of an appropriately dilute solution of 1:Fe(II) or P5E:Fe(II). After equilibration for 2 h at 37° C., cleavage was initiated by the addition of 3 $\mu$L of 5 mM dithiothreitol (DTT) solution. Final concentrations were: CT DNA, 100 $\mu$M bp; Tris, 40 mM; NaOAc, 5 mM; DTT, 1 mM. The reactions were run for 1.5 h at 37° C., then frozen, lyophilized, and resuspended in 3 $\mu$L of 100 mM Tris borate, 80% formamide solution. After heat denaturation, 2 $\mu$L (estimated precision±5%) of each sample was loaded onto a 0.2–0.6 mm thick, 40 cm long, 8% 1:20 crosslinked polyacrylamide/50% urea gel and electrophoresed at 1200 V. Gels were transferred to paper (Whatman 3 mm Chr), dried on a Bio-Rad Model 483 Slab Dryer, and autoradiographed at −78° C. using Kodak X-Omat AR or SB film. The DNA cleavage patterns were quantified by densitometry, being scanned at 633 nm using LKB Ultrascan XL Laser Densitometer model 2222. The relative peak area for each site was equated to the relative cleavage efficiency at that site.

EXAMPLE IX

We report here the synthesis and study of tri-, tetra-, penta-, and hexa-N'-methylpyrrole carboxamide-EDTA.Fe(II).

The general formula are as follows:

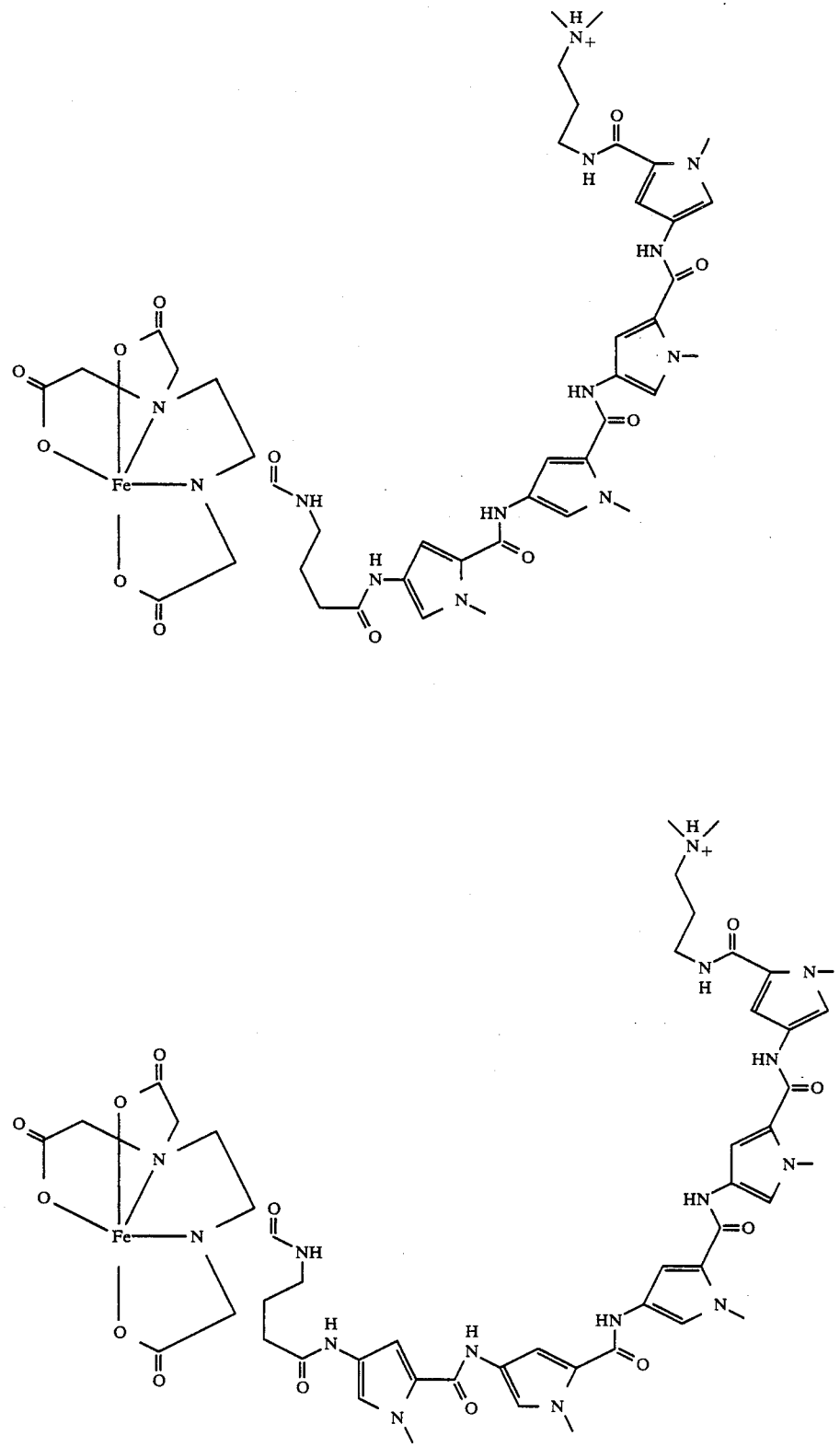

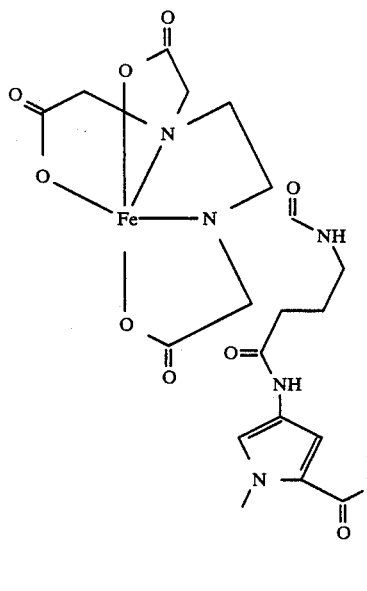
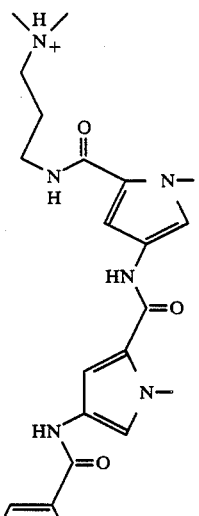

MATERIALS AND METHODS

Nuclear magnetic resonance spectra were recorded on a Varian Associates EM-390 ($^1H=90.0$) or a Bruker WM ($^1H=500.12$) spectrometer and are reported in parts per million from tetramethylsilane. Infrared spectra were recorded on a Beckman 4210 or a Shimadzu IR-435 spectrophotometer. Ultraviolet-visible spectra were recorded on a Kratos MS-50 spectrometer using FAB techniques at the Midwest Center for Mass Spectrometry at the University of Nebraska. Agarose gels were photographed with Polaroid type 55 film and the negatives were scanned at 485 nm with a Cary 219 spectrophotometer interfaced to an Apple ll computer. Autoradiography of polyacrylamide gels was carried out at $-50°$ C. on Kodak X-O mat AR film.

Reagent grade chemicals were used without further purification unless otherwise stated. N,N-dimethylformamide (DMF) was dried over 4 A° molecular sieves. N,N'-carbonyldiimidazole was sublimed under reduced pressure prior to use. Ferrous ammomium sulfate was a Baker Analyzed Reagent. Dithiothreitol (DTT) was purchased from Calbiochem. All non-aqueous reactions were run under argon with rigorous exclusion of water unless otherwise noted. Flash chromatography was performed using EM Reagents Silica Gel (230-400 mesh). All water used in biological reactions and dilutions was doubly distilled. Aqueous ($\alpha^{32}P$) dATP, triethylammonium salt, 3000 Ci/mmol, was from Amersham and aqueous ($\gamma^{32}P$) dATP, 5000-9000 Ci/mmol, was from ICN. Nucleotide triphosphates were from Boehring Mannheim. All enzymes were from New England Biolabs except bacterial alkaline phosphatase and polynucleotide kinase which were from BRL.

DNA used in this investigation was bacterial plasmid pBR322 whose entire sequence is known (Sutcliffe, 1979; Peden, 1983). The plasmid was grown in Echerichia Coli. strain HB101 and isolated by methods similar to Tanka and Weissblum (1974). Calf thymus DNA (Sigma) was sonicated, deproteinized and extensively dialized.

N-Methyl-4-nitropyrrole-2-carboxylic Acid 22. The monopyrrole nitro acid 22 was prepared by a modification of the procedure of Bailer et al. (1978). A solution of 150 gm (1.37 mol) N-methylpyrrole-2-carboxylic acid in 900 mL acetic anhydride was stirred by means of an overhead stirrer and cooled to $-25°$ C. with a dry-/acetone bath. A solution of 120 mL nitric acid at 0° C. and 350 mL acetic anhydride at 0° C. was prepared. This solution was added dropwise to the reaction mixture maintaining the temperature at $-25°$ C. The solution was stirred at $-25°$ C. for an additional hour and then poured onto 1300 mL of ice and water and stirred 1.5 h. After stirring, it was placed in a $-20°$ C. freezer for 12 h. The crystalline precipitate was collected and recrystallized from 1:1 acetic acid:water to give 105 g (45%) monopyrrole nitro acid 22. NMR (DMSO-$d_6$) $\delta 3.9$ (s, 3H), 7.25 (d, 1H, J=2 Hz), 8.25 (d, 1H, J=2 Hz)

N-Methyl-4-nitropyrrole-2-carboxylic Acid Methyl Ester 21. To a solution of 16 g (0.09 mol) monopyrrole nitro acid 22 in 160 mL methanol, 16 mL sulfuric acid was added and the solution was refluxed 17 h. The solution was then cooled and the volume was reduced under vacuum. The white crystalline product was filtered off to give 15.5 g (90%) monopyrrole nitro methyl ester (Bailer et al., 1978). NMR (CDCl$_3$) $\delta 3.85$ (s, 3H), 4.0 (s, 3H), 7.35 (d, 1H, J=1.5 Hz), 7.55 (d, 1H, J=1.5 Hz).

N-Methyl-4-(N-methyl-4-nitropyrrole-2-carboxylamide)pyrrole-2-carboxylic Acid Methyl Ester 20. A solution of 15 g (0.08 mol) monopyrrole nitro ester in 130 mL DMF was reduced over 5% palladium on charcoal (1.5 g) at atmospheric pressure. The solution was filtered through Celite to remove the catalyst and 20 mL triethylamine (0.14 mol) was added. A mixture of 15 g N-methyl-4-nitropyrrole-2-carboxylic acid 22 (0.09 mol) in 20 mL DMF was added with stirring. (N-methyl-4-nitropyrrole-2-carboxylic acid chloride was prepared by refluxing the monopyrrole acid in thionyl chloride until clear (~1 h) and removing excess thionyl chloride under vacuum.) The mixture stirred 12 h, 700 mL ice and water was added and the product was filtered off. After washing with water twice and diethyl ether, the light-green product was dried yielding 24 g (95%) of the dipyrrole nitro ester 20 (Bailer et al., 1978). NMR (DMSO-$d_6$) $\delta$3.75 (s, 3H), 3.85 (s, 3H), 4.0 (s, 3H), 6.9 (d, 1H, J=1.5 Hz), 7.5 (d, 1H, J=1.5 Hz), 7.6 (d, 1H, J=2.0 Hz), 8.2 (d, 1H, J=1.5 Hz), 10.3 (s, 1H).

4-Nitro-tri-N-methylpyrrole-2-carboxylic Acid Methyl Ester 5. A solution of 16.7 g (0.055 mol) dipyrrole nitro ester 20 in 500 mL DMF was hydrogenated over 5% palladium on charcoal 91 g) at atmospheric pressure. The solution was filtered through Celite to remove the catalyst and 15 mL (0.11 mol) triethylamine was added. A solution of 11.1 g (0.065 mol) N-methyl-4-nitropyrrole-2-carboxylic acid chloride in 15 mL DMF was added. The reaction mixture stirred 12 h, 600 mL ice and water was added and the product was filtered off. After washing with water twice and cold methanol, the light-green product was dried yielding 22 g (93%) of the tripyrrole nitro ester 5 (Bailer et al., 1978). NMR (DMSO-$d_6$) $\delta$3.75 (s, 3H), 3.83 (s, 3H), 3.85 (s, 3H), 4.0 (s, 3H), 6.9 (d, 1H, J=1.5 Hz), 7.05 (d, 1H, J=1.5 Hz), 7.25 (d, 1H), J=1.5 Hz), 7.5 (d, 1H, J+1.5 Hz), 7.6 (d, 1H, J=1.5 Hz), 8.2 (d, 1H, J=1.5 Hz), 10.0 (s, 1H), 10.35 (s, 1H).

4-Nitro-tri-N-methylpyrrole-2-carboxylic Acid 6. To a suspension of 2 g (4.7 mmol) tripyrrole nitro ester 5 in 135 mL ethanol, a solution of 1.5 sodium hydroxide in 125 mL water was added and the mixture was refluxed for 3.5 h. The solution was cooled and concentrated to 150 mL under vacuum. After acidification with 6 N HCl, the product was filtered off, washed twice with water and once with cold methanol to give 1.9 g (95%) tripyrrole nitro acid 6 (Bailer et al., 1978). IR (KBr) 1690, 1650, 1600, 1565, 1530, 1500, 1310, 1215, 1110 cm$^{-1}$; NMR (DMSO-$d_6$) $\delta$3.84 (s, 3H), 3.87 (s, 3H), 3.97 (s, 3H), 6.85 (d, 1H, J=1.5 Hz), 7.1 (d, 1H, J=1.5 Hz), 7.25 (d, 1H, J=1.5 Hz), 7.26 (d, 1H, J=1.5 Hz), 7.45 (d, 1H, J=1.5 Hz), 7.65 (d, 1H, J=1.5 Hz), 8.2 (d, 1H, J=1.5 Hz), 9.95 (s, 1H), 10.35 (s, 1H).

4-Nitro-tri-N-methylpyrrole-2-carboxamide-dimethylamine 7. A solution of 2.5 g (6.0 mmol) tripyrrole nitro acid 6, 0.68 g (6.6 mmol) 3-dimethylaminopropylamine and 0.89 g (6.6 mmol) N-hydroxybenzotriazole in 10 mL DMF was cooled to 0° C. and 1.36 g (6.6 mmol) dicyclohexylcarbodiimide was added with stirring. After stirring for 1 h at 0° C., the solution was allowed to warm to 25° C. and stir for 12 h. The DMF was removed under high vacuum, the residue was triturated twice with diethyl ether and then flash chromatographed on silica gel with 3% concentrated aqueous ammonia in methanol to give 2.1 g (70%) tripyrrole nitro amine 7. IR (KBr) 3130, 2950, 1638, 1580, 1530, 1500, 1308, 1250, cm$^{-1}$; NMR (DMSO$d_6$) $\delta$1.6 (m, 2H), 2.15 (s, 6H), 2.28 (t, 2H, J=6 Hz), 3.2 (m, 2H), 3.8 (s, 3H), 3.85 (s, 3H), 3.95 (s, 3H), 6.85 (d, 1H, J=1.5 Hz), 7.05 (d, 1H, J=1.5 Hz), 7.2 (d, 1H, J=1.5 Hz), 7.27 (d, 1H, J=1.5 Hz), 7.6 (d, 1H, J=1.5 Hz), 8.05 (t, 1H, J=4 Hz), 8.15 (d, 1H, J=1.5 Hz), 9.95 (s, 1H), 10.35 (s, 1H); m/e 499 (M+).

EDTA-triethylester 23. After dissolving 10 g (0.034 mol) EDTA in dry ethanol, 1.5 mL sulfuric acid was added with stirring and the mixture was refluxed 24 h. A 50 mL saturated aqueous sodium carbonate solution was added and the reaction mixture was extracted with 250 mL dichloromethane. The organic layer was washed three times with saturated sodium carbonate, twice with water, dried over anhydrous sodium sulfate and concentrated to give 11 g (80%) crude EDTA-tetraehtylester. The triethylester 23 was prepared according to the procedure of Hay and Nolan (1975). The crude tetraester and 4.6 g (0.027 mol) cupric chloride dihydrate were dissolved in 500 mL water. A solution of 1.3 g (0.032 mol) sodium hydroxide in 7 mL water was added with stirring at a rate to maintain the pH of the solution just below 5. The solution was then bubbled with H$_2$S and filtered. The filtrate was concentrated under vacuum and purified by flash chromatography on silica gel with 10% methanol in dichloromethane to give 9 g (90%) of the trithylester 23. IR (CH$_2$Cl$_2$) 3000, 1745, 1380, 1210 cm$^{-1}$; NMR (CDCl$_3$) $\delta$1.3 (t, 9H, J=7 Hz), 2.75 (s, 4H), 3.3 (s, 2H), 3.4 (s, 2H), 3.5 (s, 4H), 4.1 (q, 4H, J=7 Hz); m/e 376 (M+).

EDTA-triethylester-linker 8. To a solution of 5 g (0.013 mol) EDTA-triethylester 23 and 1.52 g (0.13 mol) Nhydroxysuccinimide in 100 mL dioxane was added with stirring 2.7 g (0.013 mol) of dicyclohexylcarbodiimide in 20 mL dioxane. The solution was stirred for 12 h, filtered and the filtrate concentrated. The filtrate was then dissolved in 100 mL dimethoxyethane and added with stirring to a solution of 2 g (0.02 mol) 4-aminobutyric acid and 1.68 g (0.02 mol) sodium bicarbonate in 100 mL water. After stirring 12 h, the solution was concentrated under vacuum and purified by flash chromatography on silica gel with 10% methanol in dichloromethande to give 4 g (65%) 8. IR (CH$_2$Cl$_2$) 3000, 1740, 1665, 1210 cm$^{-1}$; NMR (DMSO-$d_6$) $\delta$1.19 (t, 9H, J=7 Hz), 1.63 (m, 2H), 2.2 (t, 2H, J=6 Hz), 2.7 (t, 2H, J=6 Hz), 3.1 (m, 2H), 3.19 (s, 2H), 3.45 (s, 2H), 3.53 (s, 4H), 4.08 (m, 6H), 8.0 (t, 1H); m/e 461 (M+).

Distamycin-EDTA Triethylester 9. A solution of 200 mg. (0.40 mmol) triyrrole nitro amine 7 in 5 mL DMF was hydrogenated over 60 mg 5% palladium on charcoal at atmospheric pressure. The solution was filtered through Celite to remove the catalyst. Activated EDTA-triethylester-linker was prepared by dissolving 200 mg (0.43 mmol) EDTA-triethylester-linker 8 in 20 mL DMF and adding 80 mg N,N'-carbonyldiimidazole and allowing the solution to stir 1 h. The reduced tripyrrole nitro amine was added and the solution stirred 12 h. The reaction mixture was concentrated under high vacuum, triturated three times with diethyl ether and purified by flash chromatography on silica gel with 2% concentrated aqueous ammonia in methanol to give 300 mg (82%) 9. IR (KBr) 2940, 1730, 1650, 1570, 1530, 1460, 1430, 1400, 1250, 1200 cm$^{-1}$: NMR (DMSO-d$_6$) δ1.19 (t, 9H, J=7 Hz), 1.6 (m, 2H), 1.75 (m, 2H), 2.13 (s, 6H), 2.2 (t, 2H, J=7 Hz), 2.26 (t, 2H, J=7 Hz), 2.7 (m, 4H), 3.1 (m, 2H), 3.2 (m, 2H), 3.2 (s, 2H), 3.45 (s, 2H), 3.55 (s, 4H), 3.84 (s, 3H), 3.88 (s, 3H), 3.90 (s, 3H), 4.08 (q, 6H, J=7 Hz), 6.8 (d, 1H), 6.86 (d, 1H), 7.0 (d, 1H), 7.16 (d, 1H), 7.18 (d, 1H), 7.22 (d, 1H), 8.0 (t, 1H), 8.05 (t, 1H), 9.8 (t, 1H), 9.88 (t, 1H), 10.37 (d, 1H); m/e 912 (M+).

Distamycin-EDTA 1. A solution of 39 mg (1.6 mmol) lithium hydroxide in 10 mL water was added with stirring to a solution of 70.5 mg (0.08 mmol) distamycin-EDTA triethylester 9 in 10 mL ethanol. The solution stirred 12 h and was concentrated under vacuum. The residue was purified by flash chromatography on silica gel with 3% concentrated aqueous ammonia in methanol to give 55 mg (85%) distamycin-EDTA 1. IR (KBr) 2960, 1730, 1640, 1565, 1550, 1465, 1435, 1260, 1210, 1105 cm$^{-1}$; NMR (DMSO-d$_6$) δ1.73 (m, 2H), 1.85 (m, 2H), 2.3 (t, 2H, J=7 Hz), 2.72 (s, 6H), 3.05 (t, 2H, J=7 Hz), 3.13 (m, 2H), 3.22 (m, 2H), 3.4 (t, 2H, J=6 Hz), 3.45 (t, 2H, J=6 Hz), 3.8 (s, 3H), 3.82 (s, 3H), 3.83 (s, 3H), 3.93 (s, 4H), 4.04 (s, 2H), 4.17 (s, 2H), 6.91 (s, 1H), 6.93 (s, 1H), 7.05 (s, 1H), 7.18 (s, 1H), 7.22 (s, 1H), 7.26 (s, 1H), 8.25 (t, 1H), 8.86 (t, 1H), 9.95 (s, 1H), 9.97 (s, 1H), 10.15 (s, 1H); UV (H$_2$O) 297 nm (35,600), 236 (29,400); m/e 866 (C$_{37}$Hg$_3$N$_{11}$O$_{11}$K+).

4-Nitro-tetra-N-methylpyrrole-2-carboxylic Acid Methyl Ester 10. As solution of 8 g (19 mmol) tripyrrole nitro ester 5 in 150 mL DMF was hydrogenated over 5% palladium on charcoal (1 g) at 52 psi hydrogen on a Parr rocker. The solution was filtered through Celite to remove the catalyst and 10 mL triethylamine was added. A solution of 3.8 gm (22 mmol) N-methyl-4-nitropyrrole-2-carboxylic acid chloride in 10 mL DMF was added and the reaction mixture stirred 12 h. After stirring, 600 mL ice and water was added and the product was filtered off. The product was washed twice with water, once with cold methanol and dried yielding 7.9 g (77%) of the tetrapyrrole nitro ester 10. IR (KBr) 1700, 1660, 1580, 1540, 1440, 1400, 1305, 1245, 1105 cm$^{-1}$; NMR (DMSO-d$_6$) δ3.79 (s, 3H), 3.84 (s, 3H), 3.86 (s, 3H), 3.87 (s, 3H), 3.97 (s, 3H), 6.91 (d, 1H, J=2 Hz), 7.06 (d, 1H, J=2 Hz), 7.08 (d, 1H, J=2 Hz), 7.25 (d, 1H, J=2 Hz), 7.28 (d, 1H, J=2 Hz), 7.47 (d, 1H, J=2 Hz), 7.60 (d, 1H, J=2 Hz), 8.18 (d, 1H, J=2 Hz), 9.93 (s, 1H), 9.99 (s, 1H), 10.28 (s, 1H).

4-Nitro-tetra-N-methylpyrrole-2-carboxylic Acid 11. To a suspension of 730 mg (1.3 mmol) tetrapyrrole nitro ester 10 in 25 mL ethanol, a solution of 0.5 g sodium hydroxide in 25 mL water was added and the mixture was refluxed for 4 h. The solution was then cooled and concentrated to 35 mL under vacuum. After acidification with 6 N HCl, the product was filtered off, washed three times with water and once with diethyl ether to give 630 mg (89%) tetrapyrrole nitro acid 11. IR (KBr) 1645, 1580, 1540, 1430, 1400, 1305, 1245, 1110 cm$^{-1}$; NMR (DMSO-d$_6$) δ3.83 (s, 3H), 3.86 (s, 3H), 3.88 (s, 3H), 3.97 (s, 3H), 6.87 (s, 1H), 7.06 (s, 1H), 7.07 (s, 1H), 7.25 (s, 1H), 7.28 (s, 1H), 7.43 (s, 1H), 7.60 (s, 1H), 8.8 (s, 1H), 9.90 (s, 1H), 9.99 (s, 1H), 10.29 (s, 1H); m/e 537 (M+).

4-Nitro-tetra-N-methylpyrrole-2-carboxamide-dimethylpropylamine 12. A solution of 500 mg (0.093 mmol) tetrapyrrole nitro acid 11, 250 mg (1.9 mmol) n-hydroxybenzotriazone and 170 mg (1.7 mmol) 3-dimethylaminopropylamine in 5 mL DMF was cooled to 0° C. and 230 mg (1.1 mmol) dicyclohexylcarbodiimide was added with stirring. After stirring 1 h at 0° C., the solution was allowed to warm to 25° C. and stir for 12 h. The DMF was removed under high vacuum, the residue was triturated twice with diethyl ether and then flash chromatographed on silica gel with 2% concentrated aqueous ammonia in methanol to give 520 mg (90%) tetrapyrrole nitro amine 12. IR (KBr) 2950, 1630, 1580, 1530, 1465, 1430, 1308, 1255 cm$^{-1}$; NMR (DMSO-d$_6$) δ1.6 (m, 2H), 2.2 (s, 6H), 2.3 (t, 2H, J=7 Hz), 3.2 (m, 2H), 3.8 (s, 3H), 3.85 (s, 3H), 3.88 (s, 3H), 3.95 (s, 3H), 6.85 (s, 1H), 7.07 (m, 2H), 7.2 (s, 1H), 7.27 (s, 1H), 7.31 (s, 1H), 8.05 (t, 1H, J=7 Hz), 8.1 (s, 1H), 9.92 (s, 1H), 9.97 (s, 1H), 10.03 (s, 1H), 10.35 (s, 1H); m/e 621 (M+).

Tetra-N-methylpyrrole-carboxamide-EDTA Triethylester 13. A solution of 240 mg (0.39 mmol) tetrapyrrole nitro amine 12 in 5 mL DMF was hydrogenated over 60 mg 5% palladium on charcoal at atmospheric pressure. The solution was filtered through Celite to remove the catalyst. Activated EDTA-triethylester-linker was prepared by dissolving 210 mg (0.46 mmol) EDTA-triethylesterlinker 8 in 2 mL DMF and adding 80 mg (0.49 mmol) N,N'-carbonyldiimidazole and allowing the solution to stir 1 h. The reduced tetrapyrrole nitro amine was added to the activated EDTA-triethylester-linker and the solution stirred 12 h. The reaction mixture was concentrated under high vacuum, triturated three times with diethyl ether and purified by flash chromatography on silica gel with 3% concentrated aqueous ammonia in methanol to give 307 mg (77%) 13. IR (KBr) 2943, 1738, 1649, 1582, 1539, 1533, 1465, 1434, 1403, 1256, 1204 cm$^{-1}$; NMR (DMSO-d$_6$) δ1.18 (m, 9H), 1.62 (m, 2H), 1.72 (m, 2H), 2.15 (s, 6H), 2.25 (m, 4H), 2.70 (m, 2H), 2.73 (m, 2H), 3.14 (m, 2H), 3.19 (m, 4H), 3.46 (s, 2H), 3.51 (s, 4H), 3.80 (s, 3H), 3.84 (s, 3H), 3.85 (s, 3H), 3.86 (s, 3H), 4.06 (m, 6H), 6.83 (s, 1H), 6.88 (s, 1H), 7.05 (s, 2H), 7.16 (s, 1H), 7.18 (s, 1H), 7.24 (s, 2H), 8.00 (t, 1H), 8.06 (t, 1H), 9.80 (s, 1H), 9.88 (s, 1H), 9.90 (s, 1H), 9.93 (s, 1H); m/e 1034 (M+).

Tetra-N-methylpyrrole-carboxamide-EDTA 2. A solution of 47 mg (2.0 mmol) lithium hydroxide in 15 mL water was added with stirring to a solution of 101 mg (0.10 mmol) tetra-N-methylpyrrole-carboxamide-EDTA triethylester 13 in 10 mL ethanol. The solution stirred 12 h and was concentrated under vacuum. The residue was purified by flash chromatography on silica gel with 3% concentrated aqueous ammonia in methanol to give 77 mg (83%) 2. IR (KBr) 1620, 1580, 1540, 1460, 1435, 1400, 1260, 1200, 1100 xm$^{-1}$; NMR (DMSO-d$_6$) δ1.75 (m, 2H), 1.86 (m, 2H), 2.28 (m, 2H), 2.80 (s, 6H), 3.09 (mn, 2H), 3.16 (m, 4H), 3.27 (m, 4H), 3.73 (s, 4H), 3.85 (m, 14H), 4.04 (s, 1H), 6.89 (s, H), 6.95 (s, 1H), 7.08 (s, 2H), 7.16 (s, 1H), 7.18 (s, 1H), 7.18 (s, 1H), 7.23 (s, 2H), 8.17 (m, 1H), 8.43 (m, 1H), 9.85 (s, 1H), 9.91 (s, 1H), 9.94 (s, 1H); UV (H$_2$O) 309 nm 39,000 (Zimmer et al., 1980); m/e 951 (M+).

4-Nitro-penta-N-methylpyrrole-2-carboxylic Acid Methyl Ester 14. A solution of 12.2 g (22 mmol) tetrapyrrole nitro ester 10 in 350 mL DMF was hydrogenated over 5% palladium on charcoal (2 g) at 52 psi hydrogen on a Parr rocker. The solution was filtered through Celite to remove the catalyst and 10 mL triethylamine was added. A solution of 4.7 gm N-methyl-4-nitropyrrole-2-carboxylic acid chloride (27 mmol) in 10 mL DMF was added and the reaction mixture stirred 12 h. After stirring, 750 mL ice and water was added and the product was filtered off. The product was washed three times with water, once with cold methanol and dried yielding 13.5 gm (90%) of the pentapyrrole nitro ester 14. IR (KBr) 1700, 1660, 1590, 1520, 1440, 1390, 1305, 1250, 1100 cm$^{-1}$; NMR (DMSO-d$_6$) δ3.78 (s, 3H), 3.85 (s, 9H), 4.02 (s, 3H), 6.91 (s, 1H), 7.10 (s, 3H), 7.25 (s, 3H), 7.45 (s, 1H), 7.60 (s, 1H), 8.14 (s, 1H), 9.86 (m, 3H), 10.2 (s, 1H); m/e 673 (M+).

4-Nitro-penta-N-methylpyrrole-2-carboxylic Acid 15. To a suspension of 5 g (7.4 mmol) pentapyrrole nitro ester 14 in 200 mL ethanol, a solution of 4 g sodium hydroxide in 200 mL water was added and the mixture was refluxed for 4 h. The solution was cooled and reduced in volume to 250 mL under vaccum. After acidification with 6 N HCl, the product was filtered off, washed three times with water and once diethyl ether to give 4.77 g (97%) pentapyrrole nitro acid 15. IR (KBr) 1650, 1590, 1520, 1435, 1395, 1305, 1250, 1105 cm$^{-1}$; NMR (DMSO-d$_6$) δ3.85 (s, 12H), 4.0 (s, 3H), 6.88 (s, 1H), 7.1 (s, 3H), 7.3 (m, 3H), 7.45 (s, 1H), 7.61 (s, 1H), 8.20 (s, 1H), 9.90 (s, 1H), 9.95 (s, 1H), 10.0 (s, 1H), 10.3 (s, 1H).

4-Nitro-penta-N-methylpyrrole-2-carboxamide-dimethylpropylamine 16. A solution of 1 g (1.5 mmol) pentapyrrole nitro acid 15, 0.41 g (3.0 mmol) N-hydroxybenzotriazole and 0.19 g (1.9 mmol) 3-dimethylaminopropylamine in 175 mL DMF was cooled to 0° C. and 0.47 g (2.3 mmol) dicyclohexylcarbodiimide was added with stirring. After stirring 1 h at 0° C., the solution was allowed to warm to 25° C. and stir for 12 h. The DMF was removed under high vacuum, the residue was triturated three times with diethyl ether and then flash chromatographed on silica gel with 35% concentrated aqueous ammonia in methanol to give 0.9 g (80%) pentapyrrole nitro amine 16. IR (KBr) 3350, 2945, 1627, 1580, 1530, 1465, 1435, 1307, 1260, 1110 cm$^{-1}$; NMR (DMSO-d$_6$) δ1.65 (m, 2H), 2.2 (s, 6H), 2.3 (t, 2H, J=7 Hz), 3.2 (m, 2H), 3.83 (s, 3H), 3.9 (s, 3H), 3.91 (s, 3H), 3.92 (s, 3H), 4.0 (s, 3H), 6.85 (s, 1H), 7.1 (m, 3H), 7.2 (m, 3H), 7.27 (m, 2H), 7.31 (s, 1H), 8.1 (t, 1H, J=7 Hz), 8.2 (s, 1H), 9.92 (s, 1H), 9.97 (s, 1H), 10.03 (s, 1H); m/e 743 (M+).

Penta-N-methylpyrrole-carboxamide-EDTA Triethylester 17. A solution of 1 g (1.35 mmol) nitro amine 16 in 20 mL DMF was hydrogenated over 200 mg 5% palladium on charcoal at atmospheric pressure. The mixture was filtered through Celite to remove the catalyst. Activated EDTA-triethylesterlinker was prepared by dissolving 620 mg (1.5 mmol) EDTA-triethylesterlinker 8 in 5 mL DMF and adding 240 mg (1.5 mmol) N,N'-carbonyldiimidazole and allowing the solution to stir 1 h. The reduced nitro compound was added and the solution stirred 12 h. The reaction mixture was concentrated under high vacuum, triturated three times with diethyl ether and purified by flash chromatography on silica gel with 4% concentrated aqueous ammonia in methanol to give 0.6 g (40%) 17. IR (KBr) 2960, 1725, 1650, 1585, 1470, 1440, 1410, 1260, 1210, 1110 cm$^{-1}$; NMR (DMSO-d$_6$) δ1.2 (t, 6H, J=7 Hz), 1.65 (m, 2H), 1.74 (m, 2H), 2.15 (s, 6H), 2.2 (m, 2H), 3.2 (m, 2H), 3.22 (s, 2H), 3.45 (s, 2H), 3.50 (s, 4H), 3.8 (s, 3H), 3.87 (m, 12H), 4.07 (m, 6H), 6.8 (s, 2H), 7.07 (m, 3H), 7.2 (s, 2H), 7.25 (s, 3H), 8.1 (t, 1H, J=7 Hz), 9.9 (s, 2H), 9.95 (s, 1H); m/e 1156 (M+).

Penta-N-methylpyrrole-carboxamide-Edta 3. A solution of 25 mg (1.0 mmol) lithium hydroxide in 8 mL water was added with stirring to a solution of 57.5 mg (0.05 mmol) penta-N-methylpyrrolecarboxamide-EDTA triethylester 17 in 8 mL ethanol. The solution stirred 12 h and was concentrated under vacuum. The residue was purified by flash chromatography on silica gel with 3% concentrated aqueous ammonia in methanol to give 43 mg (80%) 3. IR (KBr) 2950, 1730, 1640, 1570, 1438, 1430, 1400, 1252, 1205 cm$^{-1}$; NMR (DMSO-d$_6$) δ1.77 (m, 2H), 1.92 (m, 2H), 2.33 (t, 2H, J=7 Hz), 2.75 (s, 6H), 3.08 (m, 2H), 3.2 (m, 2H), 3.24 (m, 2H), 3.3 (m, 2H), 3.35 (m, 2H), 3.8 (s, 4H), 3.87 (m, 15H), 3.98 (s, 2H), 4.1 (s, 2H), 6.95 (m, 2H), 7.1 (m, 3H), 7.2 (s, 1H), 7.22 (s, 1H), 7.32 (s, 3H), 8.2 (s, 1H), 8.65 (s, 1H), 9.97 (m, 4H), 10.05 (s, 1H); UV (H$_2$O) 310 nm (45,000) (Zimmer et al., 1980); m/e 1072 (M+).

Tri-N-methylpyrrole-carboxylic Acid-EDTA Triethylester 18. A solution of 125 mg (0.30 mmol) tripyrrole nitro acid 6 in 2 mL DMF was hydrogenated at atmospheric pressure over 10 mg 5% palladium on charcoal. The mixture was filtered through Celite to remove the catalyst. A solution of 118 mg (0.26 mmol) EDTA-triethylester-linker 8 and 45.5 mg (0.28 mmol) N,N'-carbonyldiimidazole in 4 mL DMF was allowed to stir 1 h. After 1 h, the reduced nitro acid was added and the solution stirred 12 h. The reaction was concentrated under vacuum and triturated three times with diethyl ether. The reaction mixture was loaded onto a flash silica gel column in 10% methanol in dichloromethane and impurities were removed with a gradient to 30% methanol in dichloromethane. The product was stripped from the column with methanol to give 114 mg (53%) of 18. IF (KBr) 1730, 1650, 1570 (broad), 1435, 1400, 1200, 1020 cm$^{-1}$; NMR (DMSO-d$_6$) δ1.19 (m, 9H), 1.71 (m, 2H), 2.25 (t, 2H), 2.70 (m, 2H), 2.72 (m, 2H), 3.22 (s, 2H), 3.19 (s, 2H), 3.45 (s, 2H), 3.50 (s, 4H), 3.85 (s, 9H), 4.06 (m, 6H), 6.43 (s, 1H), 6.86 (s, 1H), 6.98 (s, 1H), 7.03 (s, 1H), 7.18 (s, 1H), 7.23 (s, 1H), 8.03 (t, 1H), 9.67 (s, 1H), 9.90 (s, 3H); m/e 828 (M+).

Hexa-N-methylpyrrole-carboxamide-EDTA Triethylester 19. A solution of 21 mg (0.042 mmol) tripyrrole nitro amine 7 in 2 mL DMF was hydrogenated over 10 mg 5% palladium on charcoal at atmospheric pressure. The solution was filtered through Celite to remove the catalyst. To the solution of reduced tripyrrole nitro amine 11.4 mg (0.084 mmol) N-hydroxybenzotriazole and 35 mg (0.042 mmol) 18 was added with stirring. After the initial reactants dissolved, 10.5 mg (0.051 mmol) dicyclohexylcarbodiimide was added and the solution stirred 12 h. The DMF was removed under high vacuum, the residue was triturated twice with diethyl ether and then flash chromatographed with 1.5% concentrated aqueous ammonia in a 50:50 v/v mixture of methanol:dichloromethane to give 16 mg (30%) 19. IR (KBr) 3100, 2950, 1734, 1653, 1576, 1558, 1540, 1436, 1256, 1204, 1026 cm$^{-1}$; 1.18 (m, 9H), 1.62 (m, 2H), 1.75 (m, 2H), 2.14 (s, 6H), 2.23 (m, 4H), 2.70 (m, 2H), 2.73 (m, 2H), 3.14 (m, 2H), 3.17 (m, 2H), 3.19 (s, 2H), 3.46 (s, 2H), 3.51 (s, 4H), 3.80 (s, 3H), 3.84 (s, 3H), 3.85 (s, 3H), 3.87 (s, 9H), 4.06 (m, 6H), 6.83 (s, 1H), 6.88 (s, 1H), 7.06 (s, 1H), 7.07 (s, 1H), 7.09 (s, 3H), 7.16 (s, 1H), 7.18 (s, 1H), 7.25 (s, 3H), 8.00 (t, 1H), 8.06 (t, 1H), 9.80 (s, 1H), 9.88 (s, 1H), 9.89 (s, 1H), 9.94 (s, 2H)); m/e 1278 (M+).

Hexa-N-methylpyrrole-carboxamide-EDTA 4. A solution of 2.3 mg (0.10 mmol) lithium hydroxide in 0.48 mL water was added with stirring to a solution of 6 mg (0.005 mmol) hexa-N-methylpyrrole-carboxamide-EDTA triethylester 19 in 0.48 mL ethanol. The solution stirred 12 h and was concentrated under vacuum. The residue was purified by flash chromatography on silica gel with 2.5% concentrated aqueous ammonia in methanol to give 4.41 mg (78%) 4. IR (KBr) NMR (DMSO-d$_6$ w/CF$_3$OH) $\delta$1.75 (m, 2H), 1.85 (m, 2H), 2.29 (t, 2H), 2.80 (m, 6H), 3.09 (m, 2H), 3.17 (m, 4H), 3.26 (m, 2H), 3.31 (m, 2H), 3.74 (s, 4H), 3.85 (m, 18H), 3.91 (s, 2H), 4.07 (s, 2H), 6.89 (s, 1H), 6.96 (s, 1H), 7.09 (s, 2H), 7.11 (s, 2H), 7.16 (s, 1H), 7.17 (s, 1H), 7.23 (s, 4H), 8.16 (t, 1H), 8.41 (t, 1H), 9.82 (s, 1H), 9.90 (m, 2H), 9.94 (s, 3H); UV (H$_2$O) 511 nm (50,000 est.); m/e 1195 (M+).

Cleavage Efficiency Assay. Each compound was characterized spectroscopically before use. Each DNA cleaving molecule was freshly prepared.

EXAMPLE X

Experimental Section

Preparation of Compounds. General. $^1$H NMR spectra were recorded at 90 MHz on Varian EM-390 or JEOL FX-90Q instruments, or at 400 MHz on a JEOL JN-M-GX400. Solvent for NMR was Me$_2$SO-d$_6$ unless otherwise noted, and chemical shifts are reported in parts per million downfield from internal Me$_4$Si. High resolution fast-atom bombardment mass spectra (FAB MS) and electron impact mass spectra (EI MS) were obtained from the Midwest Center for Mass Spectrometry at the University of Nebraska, Lincoln. IR spectra were recorded on a Shimadzu IR435 instrument. UV-visible spectra were recorded on a Cary 219 Spectrophotometer in the baseline correct mode. Optical rotations were measured using a Jasco DIP 181 Digital Polarimeter.

Chromatography was carried out under positive air pressure using EM Science Kieselgel 60 (230–400 mesh). Reagent grade chemicals were used as received except for dimethylformamide (DMF, Mallinckrodt), which was dried over 4A° molecular sieves. Non-aqueous reactions were carried out under argon.

N-Methyl-4-nitropyrrole-2-carboxylic acid (4), N-methyl4-(N-methyl-4-nitropyrrole-2-carboxamide)-pyrrole-2-carboxylic acid (5), N-methyl-4-[N-methyl-4-(N-methyl-4-nitropyrrole-2-carboxamide)pyrrole-2-carboxamide]-pyrrole-2-carboxylic acid (12), and penta (N-methyl-4-pyrrole-2-carboxamide)-EDTA (3) were prepared as previously described.

N-Methyl-4-(N-methyl-4-nitropyrrole-2-carboxamide)-pyrrole-2-carboxamide-N,N-dimethylpropylamine (6). A solution of 5 (1.46 g, 5.0 mmol), 1-hydroxybenzotriazole hydrate (1-HBT, Aldrich, 1.35 g, 10.0 mmol), and 3-dimethylaminopropylamine (Aldrich, 0.7 mL, 5.5 mmol) in 50 mL DMF was stirred under argon in an ice/water bath. Dicyclohexylcarbodiimide (DCC, Aldrich, 1.15 gm, 5.5 mmol) in 5 mL DMF was added and the reaction mixture warmed to room temperature (RT) and stirred for 24 h. The mixture was filtered and the solvent was distilled in vacuo. The residue was triturated with ether and then chromatographed on silica gel using 1% (v/v concentrated aqueous ammonia in methanol (1% NH$_4$OH/MeOH) to afford 1.67 g (4.4 mmol, 88%) of 6 as a beige solid. $^1$H NMR $\delta$ 10.23 (s, 1H), 8.13 (s, 1H), 8.07 (t, 1H), 7.53 (s, 1H), 7.17 (s, 1H), 6.77 (s, 1H), 3.90 (s, 3H), 3.77 (s, 3H), 3.2 (m, 2H); FAB ms, calcd. for C$_{17}$H$_{25}$N$_6$O$_4$(M+H+): 377.1937. Found: 377.1925.

1,3-Diaminopropane, Mono-t-butylcarbamate (7). Neat di-tertbutyldicarbonate (Aldrich, 4.4 g, 20 mmol) was added dropwise to vigorously stirred 1,3-diaminopropane (Aldrich, 20 mL, 0.24 mol) at 0° C. over 30 min. After addition was complete, the mixture was stirred at 0° C. for 10 min and then at RT for 30 min. Excess 1,3-diaminopropane was removed by in vacuo distillation with a Kugelrohr apparatus, and the residue was chromatographed on silica gel using 1% NH$_4$OH/MeOH to afford 2.45 g (14 mmol, 68%) of 7 as a white solid. $^1$H NMR (CDCl$_3$) $\delta$ 4.8 (br s, 1H), 3.1 (m, 2H), 2.7 (m, 2H), 1.6 (m, 2H), 1.4 (s, 11H).

N-Methyl-4-(N-methyl-4-nitropyrrole-2-carboxamide)pyrrole-2-carboxamide-propyl-t-butylcarbamate (8). To a stirred solution of 5 (1.46 g, 5.0 mmol) 7 (0.87 g, 5.0 mmol), and 1-hbt (1.35 g, 10.0 mmol) in 50 mL DMF at 0° C. under argon was added DCC (1.13 g, 5.5 mmol) in 1 mL DMF. The cooling bath was removed and the mixture stirred at RT for 24 h. After filtration, the DMF was distilled in vacuo. Trituration with ether afforded a fluffy solid which could be recrystallized from hot CHCl$_3$ to afford 1.70 gm (3.8 mmol, 76%) of 8 as a white solid in two crops. $^1$H NMR $\delta$ 10.25 (s, 1H), 8.17 (s, 1H), 7.97 (t, 1H), 7.50 (s, 1H), 7.18 (s, 1H), 6.83 (s, 1H), 6.74 (t, 1H), 3.93 (s, 1H), 3.78 (s, 3H), 3.2 (m, 2H), 3.0 (m, 2H), 1.6 (m, 2H), 1.4 (s, 9H); FAB ms, calcd. for C$_{20}$H$_{29}$-N$_6$O$_6$(M+H+): 449.2149. Found: 449.2145.

4-Aminobutyric Acid, t-Butycarbamate (9).[13] To a stirred, cooled solution of 4-aminobutyric acid (Aldrich, 10.3 g, 100 mmol) in 400 mL 2:1:1 dioxane/H$_2$O/1N NaOH was added di-tert-butyldicarbonate (24.0 g, 110 mmol) in 10 mL dixoane over 30 min. The mixture was stirred for 30 min in the cooling bath and then for 45 min at Rt. Dioxane was removed at RT under reduced pressure, and the aqueous solution treated with 400 mL ethyl acetate. The aqueous phase was acidified to pH 3 using 2 N KHSO$_4$ with cooling and vigorous stirring. The layers were separated and the aqueous phase extracted with 2×200 mL ethyl acetate. The combined extracts were washed with 200 mL H$_2$O dried over Na$_2$SO$_4$, and concentrated to a thick oil which solidified upon seeding. Stirring the solid with 100 mL hexane and then filtering afforded 13.5 (68 mmol, 68%) of 9 as a fluffy white solid. $^1$H NMR δ 6.81 (t, 1H), 2.92 (m, 2H), 2.19 (t, 2H), 1.59 (m, 2H), 1.37 (s, 9H).

Imidazolium N-methyl-4-[N-methyl-4-[(4-t-butylcarbamoy)butyramide]-2-carboxamide]-pyrrole-2-carboxylate (10). A solution of 4 (0.64 g, 2.2 mmol) and triethylamine (Baker, 0.84 mL, 6.0 mmol) in 10 mL DMF was treated with 5% palladium on charcoal (5% Pd/C, MCB, 100 mg), and hydrogenated at atmospheric pressure and RT for 20 h. This mixture was added to a stirred solution of 8 (0.41 g, 2.0 mmol) and N,N'-carbonyldiimidazole (CDI, Alrich, 0.36 g, 2.2 mmol) in 5 mL DMF. After stirring at RT for 16 h, the mixture was filtered, and the solvent was distilled in vacuo. The residue was triturated with ether. Chromatography on silica gel using 10% MeOH/CH$_2$Cl$_2$ followed by 33% MeOH/CH$_2$Cl$_2$ afforded 0.93 g (1.8 mmol, 90%) of brown foam shown by NMR to be the imidazolium salt 10. $^1$H NMR δ 9.85 (s, 1H), 9.82 (s, 1H), 7.65 (s, 2H), 7.38 (s, 1H), 7.15 (d, 1H), 7.02 (s, 3H), 6.86 (d, 1H), 6.84 (t, 1H), 6.81 (d, 1H), 3.83 (s, 3H), 3.82 (s, 3H), 2.95 (m, 2H), 2.22 (t, 2H), 1.67 (m, 2H), 1.38 (s, 9H).

(R,R)-2,2-Dimethyl-1,3-dioxolane-4,5-dicarboxylic acid, monomethyl ester (11h), and (S,S)-2,2-dimethyl-1,3-dioxolane4,5-dicarboxylic acid monomethyl ester (11c), were prepared from d- and l-tartaric acid (Aldrich), respectively, following the procedure of Musich and Rapoport.

(R,S)-2,2-Dimethyl-1,3-dioxolane-4,5-dicarboxylic acid, dimethyl ester were synthesized via the procedure or Holy. Monohydrolysis using the conditions of Musich and Rapoport afforded, after acidic extraction, concentration, and distillation, a 1.5:ratio (NMR) of threo:erythro [(RS,SR), 11j] monomethyl esters. 1H NMR (CDCl$_3$) threo δ 4.80 (s, 2H), 3.80 (s, 3H), 1.54 (s, 6H); erythro δ 4.87 (s, 2H), 3.73 (s, 3H), 1.64 (s, 3H), 1.43 (s, 3H). No attempt was made to separate the isomers at this point; it was found that they could be separated following the next synthetic step (see 11j).

(S)-N,N-Dimthylapartic Acid,β-Cyclohexyl Ester (11k). L-Aspartic acid, t-boc, β-cyclohexy ester (Peninsula Laboratories, 3.15 g, 10.0 mmol) was stirred under argon at 0° C. in 5 mL CH$_2$Cl$_2$. Trifluoroacetic acid (TFA, MCB, 4.0 mL) was added via syringe, and the mixture removed from the cooling bath and stirred at RT for 1 h. The product was precipitated by adding 10 mL of anhydrous ether, and the supernatant decanted. The residue was dissolved in 10 mL 10% NH$_4$OH/MeOH, and concentrated at 30° C. under reduced pressure. Addition of 10 mL more solvent and evaporation at 55° C. gave a white solid which was subjected to reductive alkylation. A solution of H$_2$O (75 mL) was added, and the mixture was heated. Aqueous formaldehyde (37%) (Baker, 4.0 mL, 50 mmol) was added, and the mixture heated to homogeneity. After cooling to RT, the solution was treated with 25 mL additional H$_2$O, 4.0 mL additional formaldehyde solution, and 2.0 g of 5% Pd/C. The mixture was hydrogenated at 50 psi and Rt for 15 h, filtered, and the residue was washed with two 25-mL portions of hot H$_2$O. Concentration in vacuo afforded a thick oil which was treated with 5 mL H$^2$O and concentrated again. Treatment with 15 mL MeOH and concentration gave an oil which was chromatographed on silica gel using 0.5% NH$_4$OH/MeOH to afford 1.33 g (5.7 mmol, 57% overall) of 11k as a white solid. $^1$H NMR δ 4.68 (m, 1H), 3.59 (m, 1H), 2.72 (dd, 1H), 2.54 (dd, 1H), 2.40 (s, 6H), 1.9–1.6 (m, 4H), 1.5–1.2 (m-6H).

(R)-N,N-Dimethylaspartic Acid (11l). D-Aspartic acid (Aldrich, 6.65 g, 50 mmol) was dissolved in 50 mL H$_2$O and treated with 37% aqueous formaldehyde (12.1 mL, 150 mmol) and 5.0 g of 5% Pd/C. The mixture was hydrogenated at 50 psi and RT for 16 h, heated, filtered, and the residue washed with 25 mL hot H$_2$O. Cooling to RT and then 5° C. afforded cubic crystals which, upon recrystallization from H$_2$O/Et-OH/Me$_2$CO, gave 2.95 g (18 mmol, 37%) of 11 l as white needles, mp 187°–199° C. (lit.$^{17}$mp 198° C). $^1$H NMR (D$_2$O) δ 4.0 (m, 1H), 2.95–2.80 (m, 2H), 2.85 (s, 6H).

N-Methyl-4-nitropyrrole-2-carboxamide-N,N-dimethylaminopropylamine (13) was prepared in 84% yield from 4 following the procedure used to prepare 6, except that chromatography solvent was 0.5% NH$_4$OH/MeOH. $^1$H NMR δ 8.4 (br s, 1H), 8.05 (d, 1H), 7.33 (s, 1H), 3.87 (s, 3H), 3.2 (m, 2H), 2.22 (t, 2H), 2.12 (s, 6H), 1.61 (m, 2H).

N-Methyl-4-[N-methyl-4-(N-methyl-4-nitropyrrole-2-carboxamide)-pyrrole-2-carboxamide]-pyrrole-2-carboxamidepropyl-t-butylcarbamate (14) was prepared from 7 and 12 in 50% yield following the procedure described for 8. $^1$H NMR δ 10.30 (s, 1H), 9.96 (s, 1H), 8.19 (s, 1H), 7.98 (t, 1H), 7.60 (s, 1H), 7.28 (s, 1H), 7.20 (s, 1H), 7.04 (s, 1H), 6.86 (s, 1H), 6.80 (t, 1H), 3.97 (s, 3H), 3.86 (s, 3H), 3.80 (s, 3H), 3.17 (m, 2H), 2.96 (m, 2H), 1.58 (m, 2H), 1.38 (s, 9H).

General procedure for the Synthesis of N,N-Dimethylamino Acids 15. Compound 6 (0.42 g, 11 mmol) was dissolved in 10 mL DMF and treated with 50 mg of 5% Pd/C. The mixture was hydrogenated at atmospheric pressure and RT for 16 h, then treated with 1-HBT (0.27 gm, 2.0 mmol) and 5–10 equiv. of the appropriate diacid 11. This mixture was stirred under argon in an ice bath and treated with DCC (0.23 gm, 1.1 mmol) in 1 mL DMF. The cooling bath was removed and the mixture stirred overnight at RT. After filtration, distillation, and trituration, the residue was chromatographed on silica gel using 1 Or 2% NH$_4$OH/MeOH to afford 15 as yellow solids.

N-Methyl-4-[N-methyl(succinamic acid)-pyrrole-2-carboxamide]pyrrole-2-carboxamide-N,N-dimethylpropylamine (15a) was synthesized using monomethyl succinate (Aldrich, 0.13 gm, 1.0 mmol) to afford 15a methyl ester in 76% yield. Hydrolysis using 2 equivs. of LiOH in MeOH (3h, RT) afforded 15a in 76% yield after chromatography. $^1$H NMR δ 10.06 (s, 1H), 9.78 (s, 1H), 8.05 (t, 1H), 7.1 (m, 2H), 6.8 (m, 2H), 3.82 (s, 3H), 3.80 (s, 3H), 3.18 (m, 2H), 2.52 (s, 4H), 2.20 (t, 2H), 2.12 (s, 6H), 1.6 (m, 2H).

N-Methyl-4-[N-methyl-4-(malonamic acid)-pyrrole-2-carboxamide]-pyrrole-2-carboxamide-N,N-dimethylpropylamine (15b), 49% from malonic acid (Aldrich). $^1$H NMR δ 10.55 (s, 1H), 9.83 (s, 1H), 8.08 (t, 1H), 7.18 (d, 1H), 7.16 (d, 1H), 6.89 (s, 1H), 6.84 (s, 1H), 3.83 (s, 3H), 3.80 (s, 3H), 3.18 (m, 2H), 3.17 (s, 2H), 2.46 (t, 2H), 2.30 (s, 6H), 1.68 (m, 2H); FAB ms, calcd. for $C_{20}H_{29}N_6O_5$ (M+H+): 433.2199. Found: 433:2204.

N-Methyl-4-[N-methyl-4(fumaramic acid)-pyrrole-2-carboxamide]pyrrole-2-carboxamide]-pyrrole-2-carboxamideN,N-dimethylpropylamine (15c) was synthesized using fumaric acid, monoethyl ester (Aldrich, 0.16 g, 1.1 mmol) to afford 15c ethyl ester in 69% yield. $^1$H NMR (two low-field NH resonances not recorded) δ 8.06 (t, 1H), 7.31–6.71 (series of singlets, 6H), 4.20 (q, 2H), 3.85 (s, 3H), 3.79 (s, 3H), 3.21 (m, 2H), 2.23 (t, 2H), 2.12 (s, 6H), 1.59 (m, 2H), 1.25 (t, 3H). Hydrolysis of this material as for 15a methyl ester afforded 15c in 84% yield. $^1$H NMR δ 10.38 (s, 1H), 9.92 (s, 1H), 8.06 (t, 1H), 7.28 (s, 1H), 7.18 (s, 1H), 6.94 (s, 1H), 6.84 (s, 2H), 6.69 (s, 1H), 3.83 (s, 3H), 3.80 (s, 3H), 3.2 (m, 2H), 2.50 (t, 1H), 2.38 (s, 6H), 1.7 (m, 2H).

(R,R)-N-Methyl-4-(tartaramic acid)-pyrrole-2-carboxamide]pyrrole-2-carboxamide-N,N-dimethylpropylamine (15e), 77% from d-tartaric acid (Aldrich). $^1$H NMR (Me$_2$SO-d$_6$+TFA) δ 9.84 (s, 1H), 9.54 (s, 1H), 8.14 (t, 1H), 7.22 (s, 1H), 7.14 (s, 2H), 6.57 (s, 1H), 4.35 (s, 2H), 3.85 (s, 3H), 3.84(s, 3H), 3.19 (m, 4H), 2.81 (d, 6H), 1.87 (m, 2H); FAB ms, calcd. for $C_{21}H_{31}N_6O_7$ (M+H+): 479.2254. Found: 479.2234.

(S,S)-N-Methyl-4-[N-methyl-4-(tartaramic acid)-pyrrole2-carboxamide]-pyrrole-2-carboxamide-N,N-dimethylpropylamine (15f), 41% from l-tartaric acid (Aldrich). $^1$H NMR δ 9.85 (s, 1H), 9.52 (s, 1H), 8.11 (t, 1H), 7.18 (s, 2H), 7.03 (s, 1H), 6.84 (s, 1H), 4.30 (s, 1H), 4.11 (s, 1H), 3.81 (s, 3H), 3.79 (s, 3H), 3.20 (m, 2H), 2.54 (t, 2H), 2.36 (s, 6H), 1.69 (m, 2H); FAB ms, calcd. for $C_{21}H_{31}N_6O_7$(M+M+): 479.2254. Found: 479.2241.

(RS,SR)-N-methyl-4-[N-methyl-4-(tartaramic acid)-pyrrole2-carboxamide]pyrrole-2-carboxamide-N,N-dimethylpropylamine (15g), 84% from meso-tartaric acid hydrate (Aldrich). $^{1H}$NMR δ 9.85 (s, 1H), 9.76 (s, 1H), 8.07 (t, 1H), 7.18 (s, 2H), 6.97 (s, 1H), 6.83 (s, 1H), 3.89 (s, 1H), 3.87 (s, 1H), 3.82 (s, 3H), 3.80 (s, 3H), 3.19 (m, 2H), 2.38 (t, 2H), 2.25 (s, 6H) 1.65 (m, 2H); FAB ms calcd. for $C_{21}H_{31}N_6O_7$ (M+H+): 479.2254. Found: 479.2227.

(R,R)-N-Methyl-4-[N-methyl-4-(O,O'-isopropylidenetartaramic acid)-pyrrole-2-carboxamide]-pyrrole-2-carboxamideN,N-dimethylpropylamine (15h), methyl ester was prepared using 1.0 equiv. of 11h. $^1$H NMR δ 10.22 (s, 1H), 9.90 (s, 1H), 8.07 (t, 1H), 7.22 (s, 1H), 7.18 (s, 1H), 7.00 (s, 1H), 6.81 (s, 1H), 4.86 (d, 1H), 4.73 (d, 1H), 3.84 (s, 3H), 3.80 (s, 3H), 3.72 (s, 3H), 3.18 (m, 2H), 2.27 (t, 2H), 2.16 (s, 6H), 1.61 (m, 2H), 1.43 (s, 3H), 1.42 (s, 3H); FAB ms, calcd. for $C_{25}H_{37}N_6O_7$ (M+H+): 533.2724. Found 533.2716. Hydrolysis as for 15a, and chromatography afforded 15h in 90% yield. $^1$H NMR (two low-field NH resonances not recorded) δ 8.12 (t, 1H), 7.20 (s, 1H), 7.18 (s, 1H0, 6.94 (s, 1H), 6.86 (s, 1H), 4.49 (d, 1H), 4.40 (d, 1H), 3.83 (s, 3H), 3.80 (s, 3H), 3.21 (m, 2H0, 2.67 (t, 2H), 2.46 (s, 6H), 1.74 (m, 2H), 1.38 (s, 3H), 1.36 (s, 3H); FAB ms, calcd. for $C_{24}H_{35}N_6O_7$ (M+H+): 519.2567. Found: 519.2578.

(S,S)-N-Methyl-4-[N-methyl-4-(0,0'-isopropylidenetartaramic acid)-pyrrole-2-carboxamide]-pyrrole-2-carboxamideN,N-dimethylpropylamine (15l) methyl ester was prepared in 59% yield using 1.0 equiv. of 11i. Spectral data matched that for 15h methyl ester. Hydrolysis as for 15a, and chromatography afforded 15i in 90% yield. The $^1$H NMR spectrum matched that for 15h, but here a low-field resonance was recorded at δ 9.87. FAB ms, calcd. for $C_{24}H_{35}N_6O_7$ (M+H+): 519.2567. Found: 519.2574.

(RS,SR)-N-Methyl-4[N-methyl-4-(0,0'-isopropylidenetartaramic acid)-pyrrole-2-carboxamide]-pyrrole-2-carboxamideN,N-dimethylpropylamine (15j), methyl ester was prepared as a mixture with the d, l compound using the mixture 11j. Separation of the diastereomers could be achieved following hydrolysis as for 15a, and 15j was obtained in 8% overall yield from 6. $^1$H NMR δ 9.90 (s, 1H), 9.88 (s, 1H), 8.07 (t, 1H), 7.17 (s, 2H), 6.93 (s, 1H), 6.83 (s, 1H), 4.77 (d, 1H), 4.69 (d, 1H), 3.81 (s, 3H), 3.79 (s, 3H), 3.17 (m, 2H), 2.35 (t, 2H), 2.22 (s, 6H), 1.63 (m, 2H), 1.33 (s, 3H), 1.30 (s, 3H); FAB ms, calcd. for $C_{24}C_{35}N_6O_7$(M+H+): 519.2567. Found: 519.2575.

(S)-N-Methyl-4-[N-methyl-4-(N,N-dimethyl-β-aspartamic acid)-pyrrole-2-carboxamide]-pyrrole-2-carboxamide-N,N-dimethylpropylamine (15K), cyclohexyl ester was prepared as a 1:1 mixture with the α-isomer 15M, cyclohexyl ester in 65% combined yield using 1.0 equiv. of 11k. The isomerization was puzzling, but the regioisomers could be separated after hydrolysis as for 15a. $^1$H NMR data the least mobile isomer on silica gel using 1% NH$_4$OH/MeOH eluent was similar to that of 11k, indicating that this was the β-amide isomer. EI ms for the enantiomeric 15l showed loss of —CH[N (CH$_3$)$_2$]COOH, —CH$_2$, and CO fragments not shown by 15m (see below), further supporting the structural assignment. 15k $^1$H NMR δ 10.57 (s, 1H), 9.84 (s, 1H), 8.06 (br s, 1H), 7.17 (d, 1H), 7.16 (d, 1H), 6.86 (d, 1H), 6.81 (d, 1H), 3.82 (s, 3H), 3.79 (s, 3H), 3.50 (m, 1H), m 3.17 (m, 2H), 2.72 (dd, 1H), 2.53 (dd, 1H), 2.40 (s, 6H), 2.24 (t, 2H), 2.14 (s, 6H), 1.61 (m, 2H); FAB ms, calcd. for $C_{23}H_{36}N_7O_5$ (M+H+): 490.2778. Found: 490.2762.

(S)-N-Methyl-4-[N-methyl-4-(N,N-dimethyl-α-aspartamic acid)-pyrrole-2-carboxamide]-pyrrole-2-carboxamide-N,N-dimethylpropylamine (15m)). 1H NMR δ 10.15 (s, 1H), 9.85 (s, 1H0, 8.06 (t, 1H), 7.17 (s, 2H), 6.93 (s, 1H), 6.80 (s, 1H), 3.82 (s, 3H), 3.79 (s, 3H), 3.58 (m, 1H), 3.17 (m, 2H), 2.60 (dd, 1H), 2.39 (dd, 1H), 2.26 (t, 2H), 2.24 (s, 6H), 2.14 (s, 6H), 1.61 (m, 2H); FAB ms, calcd. for $C_{23}H_{36}N_7O_7$ (M+H+): 490.2778. Found: 490.2774.

(R)-N-Methyl-4-[N-methyl-4-(N,N-dimethyl-α-aspartamic acid)-pyrrole-2-carboxamide]pyrrole-2-carboxamide-N,N-dimethylpropylamine (15*l*) and (R)-N-methyl-4-]N-mehtyl-4-(N,N-dimethyl-α-aspartamic acid)-pyrrole-2-2carboxamide-pyrrole-2-carboxamide-N,N-dimethylpropylamine (15*n*) were prepared as a 1:1 mixture using 5 equiv. of 11*l*. Chromatography separated the isomers and each was obtained in 21% yield. 15*l* $^1$H NMR δ 10.30 (s, 1H), 9.84 (s, 1H), 8.06 (t, 1H), 7.17 (d, 1H), 7.16 (d, 1H), 6.86 (d, 1H), 6.81 (d, 1H), 3.82 (s, 3H), 3.79 (s, 3H), 3.62 (m, 1H), 3.18 (m, 2H), 2.76 (dd, 1H), 2.56 (dd, 1H), 2.44 (s, 6H), 2.25 (t, 2H), 2.14 (s, 6H), 1.61(m, 2H); FAB ms, calcd. for $C_{23}H_{36}N_7O_5$ (M+H+): 490.2778. Found: 490.2789; El ms, m/z 442,428,388 ($-C_4H_7-NO_2$,374 ($-C_5H_9NO_2$), 346($-C_6H_9NO_3$). 15*n* $^1$NMR δ 9.90 (s, 1H), 9.86 (s, 1H), 8.07 (t, 1H), 7.18 (s, 2H), 6.95 (d, 1H), 6.81 (m, 2H), 3.81 (s, 3H), 3.80 (s, 3H), 3.62 (m, 1H), 3.19 (m, 2H), 2.65 (dd, 1H), 2.44 (dd, 1H), 2.28 (t, 2H), 2.24 (s, 6H), 2.17 (s, 6H), 1.62 (m, 2H); FAB ms, calcd. for $C_{23}H_{36}N_7O_5$ (M+H+): 490.2778. Found: 490.2776. El ms, m/z, 442,428,346 ($-C_6H_9NO_3$).

(S)-N-Methyl-4-[N-methyl-4-(β-malamic acid)-pyrrole-2carboxamide]-pyrrole-2-carboxamide-N,N-dimethylpropylamine (15*o*), 50% from L-malic acid (Aldrich). Only one regioisomer was obtained. $^1$H NMR δ 9.85 (s, 1H), 9.80 (s, 1), 8.07 (br s, 1H), 7.18 (m, 2H), 7.02 (d, 1H), 6.82 (d, 1H), 4.29 (dd, 1H), 3.81 (s, 3H), 3.79 (s, 3H), 3.18 (m, 2H), 2.58 (dd, 1H), 2.34 (dd, 1H), 2.30 (t, 2H), 2.18 (s, 6H), 1.62 (m, 2H); FAB ms, calcd. for $C_{21}H_{31}N_6O_6$ (M+H+): 463.2305. Found: 463.2306.

(R)-N-Methyl-4-[N-methyl-4-(β-malamic acid)-pyrrole-2carboxamide]-pyrrole-2-carboxamide-N,N-dimethylpropylamine (15*p*), 63% from D-malic acid (Aldrich). Spectral data matched that of 15*o*. Along with 15*p* was obtained 100 mg (22%) of the regioisomeric amide: $^1$H NMR δ 10.35 (s, 1H), 9.84 (s, 1H), 8.08 (t, 1H), 7.17 (m, 2H), 6.87 (d, 1H), 6.83 (d, 1H), 4.07 (m, 1H), 3.82 (s, 3H), 3.80 (s, 3H), 3.19 (m, 2H), 2.61 (dd, 1H), 2.43 (t, 2H), 2.38 (dd, 1H), 2.28 (s, 6H), 1.66 (m, 2H); FAB ms, calcd, for $C_{21}H_{31}N_6O_6$ (M+H+): 463.2305. Found: 463.2306.

General Procedures for the Synthesis of Bis(netropsin)Butyl-carbamate Compounds 16. A solution of 15 in 1 mL DMF was treated with 2.0 equiv. of 1-HBT and 1.1–1.5 equiv. of 8, which had been hydrogenated for 48–60 h at 50 psi and RT using 5% Pd/C and DMF. This mixture was treated with 1.1 equiv. of DCC and stirred for 24–48 h at RT. After filtration, distillation of solvent in vacuo, and trituration with ether, compounds 16 were isolated as yellow to orange solids by chromatography on silica gel using 1% NH4OH/MeOH eluent.

Bis(netropsin)succinamide-t-butylcarbamate (16*a*), 57%. This compound was not characterized, but taken on to 19*a*.

Bis(netropsin)malonamide-t-butylcarbamate (16*b*), b 57%. $^1$H NMR δ 10.07 (s, 2H), 9.86 (s, 1H), 9.85 (s, 1H), 8.06 (t, 1H), 7.96 (t, 1H), 7.18 (s, 4H), 6.89 (m, 2H), 6.84 (d, 1H), 6.82 (d, 1H), 6.78 (t, 1H), 3.84 (s, 6H), 3.80 (s, 6H), 3.34 (s, 2H), 3.17 (m, 4H), 2.96 (m, 2H), 2.26 (t, 2H), 2.15 (s, 6H), 1.6 (m, 4H), 1.38 (s, 9H); FAB ms, calcd/ for $C_{40}H_{57}N_{12}O_8$ (M+H+): 833.4422. Found: 833.4400.

Bis(netropsin)fumaramide-t-butylcarbamate (16*c*), 63%. $^1$H NMR δ 10.48 (s, 2H), 9.92 (s, 2H)8 8.07 (y, 1H), 7.97 (t, 1H). 7.33 (s, 2H), 7.19 (s, 2H), 7.09 (s, 2H), 6.94 (s, 2H), 6.86 (s, 1H), 6.83 (s, 1H), 6.79 (t, 1H), 3.87 (s, 6H), 3.80 (s, 6H), 3.18 (m, 4H), 2.96 (m, 2H), 2.28 (t, 2H), 2.17 (s, 6H), 1.62 (m, 4H), 1.39 (s, 9H).

Bis(netropsin)-4-amidobutyramide-t-butylcarbamate (16*d*). 6(0.41 g. 1.1 mmol) was hydrogenated at atmospheric pressure and RT for 20 h in 10 mL DMF using 35 mg 5% Pd/C. The mixture was then cooled in an ice water bath and treated with 1-HBT (0.27 g, 2.0 mmol) and 9 (0.20 gm, 1.0 mmol), followed by DCC (0.23 gm, 1.1 mmol) in 1mL ofd DMF. The cooling bath was removed and the mixture stirred at RT under argon for 20 h. The mixture was filtered, the solvent distilled in vacuo, and the residue triturated with ether. Chromatography on silica gel using 1% NH4OH/-MeOH afforded 0.45 g (0.85 mmol, 85%) of N-methyl-4-[N-methyl-4-(4-t-butylcarbamoylbutyramide) pyrrole-2-carboxamide]-pyrrole-2-carboxamide-N,N-dimethylpropylamine (19). $^1$H NMR δ 9.84 (s, 1H), 9.78 (s, 1H), 8.06 (t, 1H), 7.17 (d, 1H), 7.15 (d, 1H), 6.85 (d, 1H), 6.81 (d, 1H), 6.8 (br s, 1H), 3.83 (s, 6H), 3.80 (s, 6H), 3.19 (m, 2h), 2.95 (m, 2H), 2.23 (m, 4H), 2.15 (s, 6H), 1.67 (m, 2H), 1.62 (m, 2H), 1.39 (s, 9H).

Compound 19 (0.30 g, 0.56 mmol) was dissolved in 4 mL CH2Cl2, cooled in an ice water bath under argon, and treated with 1.5 mL TFA. The mixture was removed from the cooling bath and stirred for 1 h. The product was precipitated with 15 mL ether and the supernatant discarded. The residue was dissolved in 10 mL 10% NH4OH/-MeOH, then concentrated at reduced pressure. Chromatography using the same solvent afforded 200 mg (0.46 mmol, 83%) of N-methyl-4-[N-methyl-4-(4-aminobutyramide)pyrrole-2-carboxamide]-pyrrole-2-carboxamide-N,N-dimethylpropylamine (20) as a yellow foam. $^1$H NMR δ 9.84 (s, 1H), 9.81 (s, 1H), 8.07 (t, 1H), 7.18 (d, 1H), 7.15 (d, 1H), 6.85 (d, 1H), 6.81 (d, 1H), 3.82 (s, 3H), 3.80 (s, 3H), 3.18 (m, 2H), 2.55 (t, 2H), 2.25 (m, 4H), 2.14 (s, 2H), 1.63 (m, 4H). A solution of 20 (180 mg, 0.42 mmol), 1-HBT (0.14 g, 1.0 mmol) and 10 (0.26 g, 0.50 mmol), in 10 mL DMF was stirred under argon and treated with DCC (0.113 g, 0.5 mmol) in 1 mL DMF. The mixture was stirred at RT for 24 h, filtered and the solvent was distilled in vacuo. The residue was triturated with ether. Chromatography on silica gel using 1% NH4OH/MeOH eluent afforded 285 mg (0.33 mmol, 79%) of 16*d* as a yellow foam. $^1$H NMR δ 9.85 (2s, 2H), 9.84 (s, 1H), 9.78 (s, 1H), 8.05 (m, 2H), 7.17 (s, 3H), 7.15 (s, 1H), 6.89 (s, 1H), 6.86 (s, 1H), 6.83 (t, 1H), 6.81 (s, 1H), 3.83 (s, 6H), 3.81 (s, 3H), 3.80 (s, 3H), 3.25 (m, 4H), 2.95 (m, 2H), 2.25 (m, 6H), 2.15 (s, 6H), 1.79 (m, 2H), 1.67 (m, 2H), 1.61 (m, 2H), 1.38 (s, 9H).

(2R,3R)-Dihydroxybis(netropsin)succinamid-t-butylcarbamate (16*e*), 29%. $^1$H NMR δ 9.87 (s, 2H), 9.63 (s, 2H), 8.07 (t, 1H), 7.96 (t, 1H), 7.24 (s, 2H), 7.18 (m, 2H), 7.07 (s, 2H), 6.85 (d, 1H), 6.83 (d, 1H), 6.78 (t, 1H), 5.79 (br s, 1H), 5.77 (br s, 1H), 4.45 (s, 1H), 4.44 (s, 1H), 3.84

(s, 6H), 3.80 (s, 6H), 3.18 (m, 4H), 2.96 (m, 2H), 2.31 (t, 2H), 2.20 (s. 6H), 1.63 (m, 2H), 1.57 (m, 2H), 1.38 (s, 9H); FAB ms, calcd. for $C_{41}H_{59}N_{12}O_{10}$ (M+H+): 879.4476. Found: 879.4491.

(2S,3S)-Dihydroxybis(netropsin)succinamide-t-butylcarbamate (16f), 84%. Spectral data matched that of 16e.

(2RS,3SR)-Dihydroxybis(netropsin)succinamide-t-butylcarbamate (16g), 35%. $^1$H NMR δ 9.85 (s, 1H), 9.84 (s, 1H), 9.54 (s, 2H), 8.04 (t, 1H), 7.94 (t, 1H), 7.20 (s, 2H), 7.17 (s, 2H), 7.05 (s, 2H), 6.84 (s, 1H), 6.81 (d, 1H), 6.78 (t, 1H), 6.00 (br s, 1H), 5.99 (br s, 1H), 4.34 (s, 1H), 4.33 (s, 1H), 3.81 (s, 6H), 3.79 (s, 6H), 3.17 (m, 4H), 2.95 (m, 2H), 2.25 (t, 2H), 2.14 (s, 6H), 1.60 (m, 4H), 1.38 (s, 9H); FAB ms, calcd. for $C_{41}H_{59}N_{12}O_{10}$ (M+H+): 879.4476. Found: 879.4436.

(2R,3R)-Dioxy-(O,O'-isopropylidene)bis(netropsin)-succinamide-t-butylcarbamate (16h), 59%. $^1$H NMR δ 10.20 (s, 2H), 9.90 (s, 1H), 9.89 (s, 1H), 8.06 (t, 1H), 7.96 (t, 1H), 7.24 (s, 2H), 7.17 (s, 2H), 7.00 (m, 2H), 6.84 (d, 1H), 6.81 (d, 1H), 6.78 (t, 1H), 4.77 (s, 2H), 3.84 (s, 6H), 3.80 (s, 6H), 3.17 (m, 4H), 2.95 (m, 2H), 2.26 (t, 2H), 2.15 (s, 6H), 1.6 (m, 4H), 1.49 (s, 6H), 1.38 (s, 9H); FAB ms, calcd. for $C_{44}H_{63}N_{132}O_{10}$ (M+H+): 917.4790. Found: 919.4791.

(2S,3S)-Dioxy)-(O,O'-isopropylidene)bis(netropsin)-succinamide-t-butylcarbamate (16i), 57%. Spectral data matched that of 16h.

(2RS,3SR)-Dioxy-(O,O'-isopropylidene)bis(netropsin)succinamide-t-butylcarbamate (16j), yield not recorded. $^1$H NMR δ 9.84 (2s, 2H), 9.69 (s, 2H), 8.04 (t, 1H), 7.93 (t, 1H), 7.15 (s, 2H), 7.12 (m, 2H), 6.94 (m, 2H), 6.83 (s, 1H), 6.80 (s, 1H), 6.75 (t, 1H), 4.91 (s, 2H), 3.80 (s, 6H), 3.79 (s, 6H), 3.17 (m, 4H), 2.95 (m, 2H), 2.27 (t, 2H), 2.16 (s, 6H), 1.65 (s, 3H), 1.60 (m, 4H), 1.43 (s, 3H), 1.38 (s, 9H); FAB ms, calcd. for $C_{44}H_{63}N_{12}O_{10}$ (M+H+): 919.4790. Found: 919.4749.

(2S)-Dimethylaminobis(netropsin)succinamide-t-butylcarbamate (16k), 63% yield. $^1$H NMR δ 9.94 (s, 1H), 9.89 (s, 1H), 9.86 (s, 1H), 9.85 (s, 1H), 8.06 (t, 1H), 7.96 (t, 1H), 7.19 (s, 1H), 7.17 (s, 2H), 7.15 (s, 1H), 6.93 (s, 1H), 6.84 (s, 2H), 6.81 (s, 1H), 6.79 (t, 1H), 3.81 (s, 6H), 3.79 (s, 6H), 3.77 (m, 1h), 3.17 (m, 4H), 2.95 (m, 2H), 2.70 (dd, 1H), 2.55 (dd, 1H), 2.27 (s, 6H), 2.23 (t, 2H), 2.13 (s, 6H), 1.60 (m, 4H), 1.38 (s, 9H); FAB ms, calcd. for $C_{43}H_{64}N_{13}O_8$ (M+H+): 890.5001. Found: 890.4952.

(2R)-Dimethylaminobis(netropsin)succinamide-t-butylcarbamate (16l), 59%. Spectra data matched that for 16k.

(3S)-Dimethylaminobis(netropsin)succinamide-t-butelcarbamate (16m), 51% yield. $^1$H NMR δ 9.94 (s, 1H), 9.89 (s, 1H), 9.85 (s, 2H), 8.06 (t, 1H), 7.95 (t, 1H), 7.18 (d, 1H), 7.17 (m, 2H), 7.15 (d, 1H), 6.93 (d, 1H), 6.84 (s, 2H), 6.80 (s, 1H), 6.78 (t, 1H), 3.82 (s, 3H), 3.81 (s, 3H), 3.79 (s, 6H), 3.77 (m, 1H), 3.18 (m, 4H), 2.95 (m, 2H), 2.71 (dd, 1H), 2.53 (dd, 1H), 2.27 (s, 6H), 2.24 (t, 2H), 2.13 (s, 6H), 1.60 (m, 4H), 1.38 (s, 9H); FAB ms, calcd. for $C_{43}H_{64}N_{13}O_8$ (M+H+): 890.5001. Found: 890.5020.

(3R)-Dimethylaminobis(netropsin)succinamide-t-butylcarbamate (16n). The synthesis of 16n failed when the reaction was allowed to stir for two weeks at RT.

(2S)-Hydroxybis(netropsin)succinamide-t-butylcarbamate (16o), 58% yield. Spectral data matched that of 16p.

(2R)-Hydroxybis(netropsin)succinamide-t-butylcarbamate (16p), 52%. $^1$H NMR δ 9.90 (s, 1H), 9.86 (s, 2H), 9.80 (s, 1H), 8.06 (t, 1H), 7.95 (t, 1H), 7.19 (m, 2H), 7.18 (s, 2H), 7.05 (d, 1H), 6.88 (d, 1H), 6.85 1 s, 1H), 6.82 (d, 1H), 6.79 (t, 1H), 5.90 (s, 1H), 5.88 (s, 1H), 4.48 (m, 1H), 3.84 (s, 3H), 3.83 (s, 3H), 3.80 (s, 6H), 3.18 (m, 4H), 2.96 (m, 2H), 2.70 (dd, 1H), 2.53 (dd, 1H), 2.25 (t, 2H), 2.15 (s, 6H), 1.61 (m, 4H), 1.38 (s, 9H).

General Procedure for the Synthesis of Diamines 17. A solution or slurry of 16 in $CH_2Cl_2$ (0.1M) was in an ice/water bath and stirred under argon. One-half volume of TFA was added and the mixture removed from the cooling bath and stirred at RT for 1 h. The product was precipitated by the addition of 2-3 volumes of ether and the supernatant was discarded. The residue was dissolved in 10 mL of 10% $NH_4OH$/-MeOH, concentrated under reduced pressure, and chromatrographed on silica gel with 10% $NH_4OH$/MeOH to afford the diamines 17 as yellow foams.

Bis(netropsin)succinamide(17a), 54%. This material was taken to 19a without spectroscopic characterization.

Bis(netropsin)malonamide(17b), 75%. $^1$H NMR δ 10.08 (s, 2H), 9.86 (s, 2H), 8.06 (m, 2H), 7.18 (s, 4H), 6.90 (s, 2H), 6.84 (s, 1H), 6.81 (s, 1H), 3.84 (s, 6H), 3.80 (s, 6H), 3.34 (s, 2H), 3.21 (m, 4H), 2.61 (t, 2H), 2.24 (t, 2H), 2.13 (s, 6H), 1.59 (m, 4H); FAB ms, calcd. for $C_{354}H_{49}N_{12}O_6$ (M+H+): 733.3898. Found: 733.3865.

Bis(netropsin)fumaramide(17c), 36%. $^1$H NMR δ 10.49 (s, 2H), 9.92 (s, 2H), 8.06 (m, 2H), 7.32 (s, 2H), 7.17 (s, 2H), 7.08 (m, 2H), 6.93 (s, 2H), 6.87 (s, 1H), 6.81 (s, 1H), 3.85 (s, 6H), 3.79 (s, 6H), 3.16 (m, 4H), 2.66 (br s, 2H), 2.22 (t, 2H), 2.12 (s, 6H), 1.60 (m, 4H).

Bis(netropsin)-4-amidobutyramide (17d), 93%. $^1$H NMR δ 9.84 (4s, 4H), 8.05 (m, 2H), 7.17 (s, 4H), 6.89 (s, 1H), 6.87 (s, 1H), 6.85 (s, 1H), 6.81 (s, 1H), 3.82 (s, 6H), 3.80 (s, 3H), 3.79 (s, 3H), 3.2 (m, 4H), 2.28 (m, 4H), 2.24 (t, 2H), 2.13 (s, 6H), 1.79 (m, 2H), 1.7 (br m, 2H), 162 (m, 2H). That the resonance expected at δ 2.6 ($H_2N-CH_2$) was not observed and the methylene signal at δ 1.7 was so broad, was odd but reproducible; at first this was taken to mean that one 4-aminobutyric acid unit had been lost during the deprotection. However, subsequent transformation to 18d revealed this unit again in the $^1$H NMR.

(2R,3R)-Dihydroxybis(netropsin)succinamide(17e), 76%. $^1$H NMR δ 9.86 (s, 2H), 9.64 (s, 2H), 8.06 (m, 2H), 7.23 (m, 2H), 7.18 (m, 2H), 7.08 (s, 2H), 6.86 (s, 1H), 6.82 (d, 1H), 5.79 (br s, 2H), 4.45 (br s, 2H), 3.84 (s, 6H), 3.80 (s, 6H), 3.2 (m, 4H), 2.62 (t, 2H), 2.24 (t, 2H), 2.14 (s, 6H), 1.6 (m, 4H); FAB ms, calcd. for $C_{36}H_{51}N_{12}O_8$ (M+H+): 779.3953. Found: 799.3952.

(2S,3S)-Dihydroxybis(netropsin)succinamide(17f), 60%. Spectral data matched that of 17e.

(2RS,3SR)-Dihydroxybis(netropsin)succinamide(17g), 54%. $^1$H NMR δ 9.84 (s, 2H), 9.55 (s, 2H), 8.05 (m, 2H), 7.19 (m, 2H), 7.17 (m, 2H), 7.05 (s, 2H), 6.84 (s, 1H), 6.81 (d, 1H), 6.03(br s, 2H), 4.34(br s, 2H), 3.83 (s, 6H), 3.79 (s, 6H), 3.2 (m, 4h), 2.61 (t, 2H), 2.23 (t, 2H), 2.13 (s, 6H), 1.60 (m, 4H); FAB ms, calcd. for $C_{36}H_{51}N_{12}O_8$ (M+H+): 799.3953. Found: 799.3898.

(2R,3R)-Dioxy (0,0'-isopropylidene)bis(netropsin) succinamide (17h), 80%. $^1$H NMR δ 10.19 (s, 2H), 9.89 (s, 2H), 8.06 (m, 2H), 7.24 (s, 2H), 7.17 (s, 2H), 7.01 (s, 2H), 6.84 (s, 1H), 6.81 (s, 1H), 4.77 (s, 2H), 3.85 (s, 6H), 3.80 (s, 6H), 3.2 (m, 4H), 2.60 (t, 2H), 2.24 (t, 2H), 2.14 (s, 6H), 1.59 (m, 4H), 1.49 (s, 6H).

(2S,3S)-Dioxy(0,0'-isopropylidene)bis(netropsin)succinamide (17i), 83% spectral data matched that of 17h.

(2RS,3SR)-Dixoy(0,0'-isopropylidene)bis(netropsin)succinamide (17j), 33% from 15; $^1$H NMR δ 9.84 (s, 2H), 9.70 (s, 2H), 8.05 (m, 2H), 7.15 (m, 2H), 7.12 (s, 2H), 6.94 (s, 2H), 6.87 (s, 1H), 6.80 (d, 1H), 4.91 (s, 2H), 3.80 (s, 6H), 3.79 (s, 6H), 3.2 (m, 4H), 2.68 (t, 2H), 2.24 (t, 2H), 2.14 (s, 6H), 1.65 (s, 3H), 1.62 (m, 4H), 1.43 (s, 3H).

(2S)-Dimethylaminobis(netropsin)succinamide(17k), 80%. $^1$H NMR δ 9.94 (s, 1H), 9.89 (s, 1H), 9.85 (m, 2H), 7.18 (d, 1H), 7.17 (m, 2H), 7.15 (d, 1H), 6.93 (d, 1H), 6.89 (d, 1H), 6.83 (s, 1H), 6.81 (d, 1H), 3.82 (s, 6H), 3.79 (s, 6H), 3.77 (m, 1H), 3.2 (m, 4H), 2.71 (dd, 1H), 2.56 (m, 3H), 2.27 (s, 6H), 2.23 (t, 2H), 2.13 (s, 6H), 1.60 (m, 2H), 1.55 (m, 2H); FAB ms, calcd. for $C_{38}H_{56}N_{13}O_6$ (M+H+): 790.4477. Found: 790.4447.

(2R)-Dimethylaminobis(netropsin)succinamide(17l), 68%. Spectral data matched that for 17k.

(3S)-Dimethylaminobis(netropsin)succinamide(17m), 70%. $^1$H NMR δ 9.93 (s, 1H), 9.88 (s, 1H), 9.84 (2s, 2H), 8.05 (m, 2H), 7.18 (d, 1H), 7.17 (s, 2H), 7.14 (s, 1H), 6.93 (d, 1H), 6.85 (d, 1H), 6.83 (d, 1H), 6.81 (d, 1H), 3.82 (2s, 6H), 3.79 (s, 6H), 3.77 (m, 1H), 3.2 (m, 4H), 2.72(dd, 1H), 2.58(m, 3h), 2.27 (s, 6h), 2.24 (t, 2H), 2.14 (s, 6H), 1.61 (m, 2H), 1.55 (m, 2H); FAB ms, calcd. for $C_{38}H_{56}N_{13}O_6$ (M+H+): 790.4477. Found: 790.4454.

(2S)-Hydroxybis(netropsin)succinamide(17o), 63%. Spectral data matched that for 17o.

(2R)-Hydroxybis(netropsin)succinamide(17p), 41%. $^1$H NMR δ 9.92 (s, 1H), 9.87 (s, 2H), 9.81 (s, 1H), 8.07 (m, 2H), 7.19 (m, 4H), 7.05 (d, 1H), 6.88 (d, 1H), 6.84 (d, 1H). 6.82 (d, 1H), 5.95 (br s, 1H), 4.48 (m, 1H), 3.83 (2s, 6H), 3.80 (s, 6H), 3.2 (m, 4H), 2.70 (dd, 1H), 2.59 (t, 2H), 2.52 (dd, 1H), 2.24 (t, 2H), 2.13 (s, 6H), 1.61 (m, 4H).

EDTA-Triethyl Ester (18) was prepared following the procedure of Hay and Nolan, and was used either the free acid or sodium salt.

General Procedure for the Synthesis of Bis(netropsin)EDTA-Triethyl Esters, 19. A solution of 18 in DMF (0.25M) was activated with 1.1 equiv of CDl and stirred for 2 h at RT under argon. The mixture was taken up in a syringe and added to 0.25 to 0.50 equiv of 17 (dissolved in 1 mL DMF). After stirring 24 h at RT under argon, the mixture was evaporated, triturated with ether, and the residue was chromatographed using 1% NH$_4$OH/MeO to afford 19 as light yellow foams.

Bis(netropsin)succinamide-EDTA, triethyl ester (19a), 81% $^1$H NMR δ 9.89 (s, 2H), 9.86 (s, 1H), 9.84 (s, 1H), 8.05 (m, 2H), 7.99 (m, 1H), 7.17 (s, 2h), 7.15 (s, 2h), 6.86 (s, 3H), 6.81 (s, 1H), 4.06 (m, 6H), 3.82 (s, 6H), 3.80 (s, 6H), 3.60–3.47 (series of singlets, 8H), 3.18 (m 6H), 2.73 (m, 4H), 2.56 (br s, 4H), 2.24 (t, 2H), 2.14 (s, 6H), 1.60 (m, 4h), 1.18 (m, 9H); FAB ms, calcd. for $C_{52}H_{77}N_{14}O_{13}$(M+H+): 1105.5795. Found: 1105.5795.

Bis(netropsin)malonamide-EDTA,triethyl ester (19b), 99%. $^1$H NMR δ 10.06 (s, 2H), 9.86 (s, 1H), 9.84 (s, 1H), 8.04 (t, 1H), 8.03 (t, 1H), 7.97 (t, 1H), 7.18 (m, 4H), 6.90 (m, 2H), 6.85 (d, 1H), 6.82 (d, 1H), 4.07 (m, 6H), 3.84 (s, 6H), 3.80 (s, 6H), 3.61–3.47 (series of singlets, 8H), 3.34 (s, 2H), 3.19 (m, 6H), 2.72 (m, 4H), 2.30 (t, 2H), 2.18 (s, 6H), 1.62 (m, 4H), 1.19 (m, 9H).

Bis(netropsin)fumaramide-EDTA,triethyl ester (19c), 42%. $^1$H NMR δ 10.49 (s, 2H), 9.93 (m, 2H), 8.06 (m, 2H), 8.00(t, 1H), 7.33 (s, 2H), 7.19 (s, 2H), 7.09 (s, 2H), 6.94 (s, 2H), 6.86 (d, 1H), 6.83 (d, 1H), 4.07 (m, 6H), 3.387 (s, 6H), 3.81 (s, 6H), 3.61–3.48 (series of singlets, 8H), 3.2 (m, 6H), 2.72 (m, 4H), 2.25 (t, 2H), 2.15 (s, 6H), 1.62 (m, 4H), 1.18 (m, 9H); FAB ms, calcd. for $C_{52}H_{75}N_{14}O_{13}$(M+H+): 1103.5638. Found: 1103.5640.

Bis(netropsin)-4-amidobutyramide-EDTA,triethyl ester (19d), 54% $^1$H NMR δ 9.86 (s, 1H), 9.85 (s, 1H), 9.84 (s, 1H), 9.81 (s, 1H), 8.06 (m, 2H), 8.02 (m, 1H), 7.17 (m, 3H), 7.15 (d, 1H), 6.89 (d, 1H), 6.86 (m, 2H), 6.81 (d, 1H), 4.07 (m, 6H), 3.82 (s, 6H), 3.80 (s, 3H), 3.79 (s, 3H), 3.61–3.46 (series of singlets, 8H), 3.19 (m, 6H), 2.71 (m, 4H), 2.26 (m, 6H), 2.14 (s, 6H), 1.79 (m, 2H), 1.71 (m, 2H), 1.61 (m, 2H), 1.17 (m, 9H), (2R,3R)-Dihydroxybis(netropsin)succinamide-EDTA,triethyl ester (19e), 78%. $^1$H NMR δ 9.86 (s, 1H), 9.85 (s, 1H), 9.62 (s, 2H), 8.05 (t, 1H), 8.02 (t, 1H), 7.97 (t, 1H), 7.23 (m, 2H), 7.17 (m, 2H), 7.07 (m, 2H), 6.85 (d, 1H), 6.82 (d, 1H), 5.76 (d, 2H), 4.45 (d, 2H), 4.06 (m, 6H), 3.84 (s, 6H), 3.80 (s, 6H), 3.61–3.47 (series of singlets, 8H), 3.17 (m, 6H), 2.72 (m, 4H), 2.72 (m, 4H), 2.28 (t, 2H), 2.17 (s, 6H), 1.61 (m, 4H), 1.17 (m, 9H); FAB ms, calcd. for $C_{52}H_{77}N_{14}O_{15}$ (M+H+): 1137.5691. Found: 1137.5666; IR(KBr)3300, 2940, 1720, 1640, 1580, 1530, 1460, 1440, 1400, 1260, 1200, 1120 cm$^{-1}$; $[\alpha]D^{23}+60°$ (c=0.58, MeOH).

(2S,3S)-Dihydroxybis(netropsin)succinamide-EDTA,triethyl ester (19f), 61%. Spectral data matched that of 19e. [δ] $D^{23}-51°$ (c=0.61, MeOH).

(2RS,3SR)-Dihydroxybis(netropsin)succinamide-EDTA, triethyl ester (19g), 83%. $^1$H NMR δ 9.84 (s, 1H), 9.83 (s, 1H), 9.52 (m, 2H), 8.02 (m, 2H), 7.96 (t, 1H), 7.19 (m, 2H), 7.17 (s, 2H), 7.04 (s, 2H), 6.85 (d, 1H), 6.81 (d, 1H), 5.98 (d, 2H), 4.33 (d, 2H), 4.07 (m, 6H), 3.82 (s, 6H), 3.61–3.47 (series of singlets, 8H), 3.17 (m, 6H), 2.73 (m, 4H), 2.27 (t, 2h), 2.16 (s, 6H), 1.61 (m, 4H), 1.17 (m, 9H); FAB ms, calcd. for $C_{52}H_{77}N_{14}O_{15}$: 1137.5691. Found: 1137.5732.

(2R,3R)-Dioxy(O,O'-isopropylidene)bis(netropsin)succinamideEDTA, triethyl ester (19h), 87%. $^1$H NMR δ 10.19 (s, 2H), 9.90 (s, 1H), 9.89 (s, 1H), 8.05 (m, 2H), 7.98 (t, 1H), 7.24 (s, 2H), 7.18 (s, 2H), 7.18 (s, 2H), 7.00 (s, 2H), 6.85 (d, 1h), 6.82 (d, 1H), 4.77 (s, 2h), 4.06 (m, 6H), 3.84 (s, 6H), 3.80 (m, 6H), 3.61–3.47 (series of singlets, 8H), 3.17 (m, 6H), 2.72 (m, 4H), 2.33 (t, 2H), 2.21

(s, 6H), 1.63 (m, 4H), 1.48 (s, 6H), 1.17 (m, 9H); FAB ms, calcd. for $C_{55}H_{81}N_{14}O_{15}$ (M+H+): 1177.6006. Found: 1177.6047.

(2S,3S)-Dioxy(O,O'-isopropylidene)bis(netropsin)-succinamide-EDTA, triethyl ester (19i), 87%. Spectral data matched that of 19h.

(2RS,3SR)-Dioxy(O,O'-isopropylidene)bis(netropsin)succinamide-EDTA, triethyl ester (19j), 39%. $^1$H NMR δ 9.85 (s, 1H), 9.84 (s, 1H), 9.69 (s, 2H), 8.0 (m, 3h), 7.15 (s, 2H), 7.12 (s, 2H), 6.94 (s, 2H), 6.84 (s, 1H), 6.82 (s, 1H), 4.91 (s, 2h), 4.06 (m, 6H), 3.79 (2s, 12H), 3.64–3.47(series of singlets, 8H), 3.19 (m, 6H), 2.33 (t, 2H), 2.21 (s, 6H), 1.64 (s, 3H), 1.6 (m, 4H), 1.42 (s, 3H), 1.18 (m, 9H).

(2S)-Dimethylaminobis(netropsin)succinamide-EDTA, triethyl ester (19k), 28%. Spectral data matched that of 19l.

(2R)-Dimethylaminobis(netropsin)succinamide-EDTA, triethyl ester (19m), 45%. $^1$H NMR δ 9.93 (s, 1H), 9.88 (s, 1H), 9.86 (s, 1h), 9.84 (s, 1H), 8.05 (m, 2H), 7.98 (t, 1H), 7.18 (m, 3H), 7.14 (d, 1H), 6.94 (s, 1H), 6.85 (m, 2h), 6.81 (d, 1H), 4.06 (m, 6H), 3.83 (s, 3H), 3.82 (s, 3h), 3.80 (2s, 6h), 3.78 (m, 1H), 3.61–3.47(series of singlets, 8H), 3.18 (m, 6H), 2.72 (m, 5H), 2.27 (s, 6H), 2.24 (t, 2H), 2.14 (s, 6H), 1.61 (m, 4H), 1.19 (m, 9H), one proton was buried under Me$_2$SO-d$_6$ impurity at δ 2.50.

(3S)-Dimethylaminobis(netropsin)succinamide-EDTA, triethyl ester (19m), 69%. $^1$H NMR δ 9.94 (s, 1H), 9.89 (s, 1H), 9.86 (s, 2H), 8.04 (m, 2H), 7.99 (t, 1H), 7.17 (s, 3H), 7.15 (s, 1H), 6.93 (s, 1H), 6.84 (s, 2H), 6.80 (s, 1H), 4.06 (m, 6H), 3.81 (s, 6H), 3.79 (s, 6H), 3.76 (m, 1H), 3.61–3.47 (series of singlets, 8H), 3.19 (m, 6H), 2.72 (m, 5H), 2.53 (dd, 1H), 2.26 (s, 6H), 2.24 (t, 2H), 2.13 (s, 6H), 1.60 (m, 4H), 1.17 (m, 9H); FAB ms, calcd. for $C_{54}H_{82}N_{15}O_{13}$(M+H+): 1148.6217. Found: 1148.6171.

(2S)-Hydroxybis(netropsin)succinamide-EDTA,trietyl ester (19o), 78%. $^1$H NMR δ 9.94 (s, 1h), 9.87 (s, 1h), 9.86 (s, 1H), 9.84 (s, 1H), 8.05 (m, 2H), 7.99 (t, 1H), 7.19 (m, 4H), 7.05 (d, 1H), 6.88 (s, 1H), 6.85 (d, 1H), 6.82 (d, 1H), 6.01 (br s, 1H), 4.48 (m, 1H), 4.06 (m, 6H), 3.84 (s, 3h), 3.83 (s, 3H), 3.80 (2s, 6H), 3.61–3.47 (series of singlets, 8H), 3.17 (m, 6H), 2.70 (m, 5H), 2.61 (dd, 1H), 2.24 (t, 2H), 2.14 (s, 6H), 1.61 (m, 4H), 1.17 (m, 9H).

(2R)-Hydroxybis(netropsin)succinamide-EDTA-triethyl ester (19p), 52%. Spectral data matched that for 19o.

General Procedure for the Synthesis of Bis(netropsin)EDTA Compounds, 1. A solution of triester 19 in 2:1 MeOH/H$_2$O was treated with 10 equiv of LiOH and stirred overnight at RT. The mixture was evaporated and the residue was chromatographed using 1% or 2% NH$_4$OH/MeOH to afford triacids 1 as light yellow foams.

Bis(netropsin)succinamide-EDTA(1a), 87%. $^1$H NMR (Me$_2$SO-d$_6$+TFA) δ 9.90 (s, 2H), 9.87 (s, 1H), 9.85 (s, 1H), 8.40 (t, 1H), 8.16 (br s, 1H), 8.02 (br s, 1h), 7.16 (s, 4H), 6.96 (s, 1h), 6.91 (s, 1H), 6.89 (s, 2H), 4.11 (s, 2H), 3.95 (d, 2H), 3.84 (s, 6H), 3.83 (s, 3H), 3.82 (s, 3H), 3.81 (s, 4H), 3.37 (br s, 2H), 3.25 (m, 8H), 3.10 (br s, 2H), 2.81 (d, 6H), 2.59 (s, 2H), 1.86 (m, 2H); FAB ms, calcd. for $C_{46}H_{64}N_{14}O_{13}K$(M+K+): 1059.4414. Found: 1059.4273; UVH$_2$O λ$_{max}$297,237 nm.

Bis(netropsin)malonamide-EDTA (1b), 90%. $^1$H NMR (Me$_2$SO-d$_6$+TFA) δ 10.08 (s, 2H), 9.87 (s, 1H), 9.86 (s, 1H), 8.37 (t, 1H), 8.15 (t, 1H), 8.01 (t, 1H), 7.19 (s, 2H), 7.17 (d, 1H), 7.16 (d, 1H), 6.93 (d, 1H), 6.90 (m, 3H), 4.07 (s, 2h), 3.91 (s, 2H), 3.84 (s, 6H), 3.82 (s, 3H), 3.80 (s, 3H), 3.74 (s, 4H), 3.35 (s, 2H), 3.30 (m, 2H), 3.24 (m, 8H), 3.07 (m, 2H), 2.79 (d, 6H), 1.84 (m, 2H), 1.66 (m, 2H); FAB ms, calcd. for $C_{45}H_{63}N_{14}O_{13}$ (M+H+): 1007.4699. Found: 1007.4660; UV(H$_2$O) λ$_{max}$296,241 nm.

Bis(netropsin)fumaramide-EDTA (1c), 100%. $^1$H NMR (Me$_2$SO-d$_6$+TFA) (low-field N-H resonances not recorded) δ 8.41 (br s, 1H), 8.19 (br s, 1H), 8.03 (br s, 1H), 7.35 (s, 2H), 7.19 (s, 2H), 7.12 (s, 2H), 7.01 (s, 1H), 6.97 (s, 2H), 6.93 (s, 1H), 4.11 (s, 2H), 3.97 (s, 2H), 3.95 (s, 2H), 3.87 (s, 6H), 3.84 (s, 3H), 3.83 (s, 3h), 3.82 (s, 2H), 3.38 (br s, 2H), 3.26 (m, 8H), 3.10 (br s, 2H), 2.82 (d, 6H), 1.87 (m, 2h), 1.68 (m, 2H); UV(H$_2$O) λ$_{max}$301,239 nm.

Bis(netropsin)-4-amidobutyramide-EDTA (1d), 79%. $^1$H NMR (Me$_2$SO-d$_6$+TFA) δ 9.89 (s, 1H), 9.86 (s, 2h), 9.84 (s, 1H), 8.45 (t, 1H), 8.18(t, 1H), 8.07 (br s, 1H), 7.18 (s, 2H), 7.17 (d, 1H), 6.95 (d, 1H), 6.92 (d, 1H), 6.89 (s, 2H), 4.10 (s, 2H), 3.94 (s, 2h), 3.84 (s, 6h), 2.30 (m, 4H), 1.82 (m, 4H), 1.82 (m, 4H), 1.77 (m, 2H); UV (H$_2$O) λ$_{max}$301,235 nm.

(2R,3R)-Dihydroxybis(netropsin)succinamide-EDTA(1e), 77% $^1$H NMR (Me$_2$SO-d$_6$+TFA) δ 9.88 (s, 1H), 9.87 (s, 1H), 9.63 (s, 2H), 8.37 (t, 1H), 8.14 (t, 1H), 8.01 (t, 1H), 7.23 (s, 2H), 7.16 (s, 2H), 7.08 (s, 2H), 6.94 (s, 1H), 6.90 (s, 1H), 4.45 (s, 2h), 4.07 (s, 2H), 3.92 (s, 2h), 3.84 (s, 6H), 3.82 (s, 3H), 3.80 (s, 3H), 3.74 (s, 4H), 3.30 (m, 2H), 3.2 (m, 8H), 3.2 (m, 8H), 3.08 (m, 2H), 2.79 (d, 6H), 1.84 (m, 2H), 1.66 (m, 2H); FAB ms, calcd. for $C_{46}H_{64}N_{14}O_{15}K$(M+K+): 1091.4313. Found: 1091.4150; IR (KBr) 3300, 2880, 1640, 1590, 1530, 1460, 1440, 1400, 1330, 1260, 1200 cm$^{-1}$; UV (H$_2$O) λ$_{max}$299,238 nm.

(2S,3S)-Dihydroxybis(netropsin)succinamide-EDTA(1f), 68%. Spectral data matched that for 1e.

(2RS,3SR)-Dihydroxybis(netropsin)succinamide(1g), 92%. $^1$h NMR (Me$_2$SO-d$_6$+TFA) δ 9.86 (s, 1H), 9.85 (s, 1H), 9.54 (s, 1H), 9.53 (s, 1H), 8.37 (t, 1H), 8.14 (t, 1H), 8.00 (t, 1H), 7.20 (m, 2H), 7.16 (m, 2H), 7.06 (m, 2H), 6.94 (d, 1H), 6.90 (d, 1H), 4.35 (s, 2H), 4.08 (s, 2H), 3.93 (s, 2H), 3.83 (s, 6H), 3.82 (s, 3H), 3.80 (s, 3H), 3.76 (s, 4H), 3.31 (m, 2H), 3.2 (m, 8H), 3.07 (m, 2H), 2.79 (d, 6H), 1.84 (m, 2H), 1.66 (m, 2H); FAB ms, calcd. for $C_{46}H_{64}N_{14}O_{15}K$ (M+K+): 1092.4313. Found: 1092.4182; UV(H$_2$O) λ$_{max}$298,235 nm.

(2R,3R)-Dioxy(O,O'-isopropylidene)bis(netropsin)-succinamideEDTA (1h), 63%. $^1$H NMR (Me$_2$SO-d$_6$+TFA) δ 10.20 (s, 2H), 9.92 (s, 2H), 8.39 (br s, 1H), 8.17 (br s, 1H), 8.02 (br s, 1H), 7.25 (s, 2H), 7.18 (s, 2H), 7.03 (s, 2H), 6.95 (s, 1h), 6.91 (s, 1H), 4.79 (s, 2H), 4.09 (s, 2H), 3.94 (s, 2H), 3.86 (s, 6H), 3.83 (s, 3H), 3.81 (s, 3H), 3.78 (s,s 4H), 3.34 (br s, 2H), 3.2 (m, 8H), 3.09 (br s, 2H), 2.80 (d, 6H), 1.86 (m, 2H), 1.66 (m, 2H), 1.50 (s, 6H); FAB ms, calcd. for $C_{49}H_{68}H_{14}O_{15}K$(M+K+):

1131.4626. Found: 1131.4636; UV(H₂O) λ$_{max}$298,237 nm.

(2S,3S)-Dioxy(O,O'-isopropylidene)bis(netropsin)-succinamide-EDTA(li), 88%. Spectral data matched that of 1h.

(2RS,3SR)-Dioxy(O,O'-isopropylidene)bis(netropsin)succinamide-EDTA(li), 80%. ¹H NMR (me₂SO-d₆+TFA) δ 9.91 (s, 1H), 9.87 (s, 1H), 9.85 (s, 1H), 9.74 (s, 1H), 8.37 (t, 1h), 8.16 (t, 1H), 8.00 (t, 1H), 7.26 (s, 2H), 7.17 (m, 2H), 7.00 (s, 2h), 6.94 (s, 1H), 6.93 (s, 1h), 4.92 (s, 2H), 4.06 (s, 2H), 3.8 (m, 14H), 3.73 (d, 4H), 3.2 (m, 12h), 2.79 (d, 6H), 1.83 (m, 2H), 1.64 (s, 3H), 1.6 (m, 2h), 1.42 (s, 3h); FAB ms. calcd. for C₄₉H₆₉N₁₄O₁₅(M+H+): 1093.5067. Found: 1093.5050; UV(H₂O) δ$_{max}$297,237 nm.

(2S)-Dimethylaminobis(netropsin)succinamide-EDTA (1K), 100% ¹H NMR (Me₂SO-d₆+TFA) δ 10.75 (s, 1H), 10.26 (s, H), 9.92 (s, 1h), 9.88 (s, 1H), 8.39 (br s, 1H), 8.15 (br s, 1H), 8.02 (br s, 1H), 7.26 (s, 1H), 7.18 (s, 1h), 7.16 (s, 2H), 6.96 (s, 1H), 6.94 (s, 1H), 6.91 (s, 1H), 6.85 (s, 1H), 4.38 (m, 1H), 4.09 (s, 2H), 3.95 (s, 2H), 3.87 (s, 3H), 3.83 (s, 3H), 3.82 (s, 3H), 3.81 (s, 3H), 3.79 (s, 4h), 3.35 (br s, 2h), 3.2 (m, 8H), 3.10 (br s, 4H), 2.89 (br s, 6H), 2.80 (d, 6H), 1.85 (m, 2H), 1.68 (m, 2H); FAB ms, calcd. for C₄₈H₆₉N₁₅O₁₃K(M+K+): 1102.4836. Found: 1102.4820; UV(H₂O) λ$_{max}$298,236 nm.

(2R)-Dimethylaminobis(netropsin)succinamide-EDTA(1*l*), 71%. Spectral data matched that for 1k.

(3S)-Dimethylaminobis(netropsin)succinamide-EDTA (1m), 63%. ¹H NMR (Me₂SO-d₆+TFA) δ 10.76 (s, 1H), 10.27 (s, 1H), 9.94 (s, 1H), 9.87 (s, 1h), 8.40 (t, 1H), 8.18 (br s, 1H), 8.02 (br s, 1H), 7.27 (s, 1H), 7.18 (m, 2H), 7.15 (s, 1h), 6.97 (s, 1h), 6.96 (s, 1h), 6.91 (s, 1H), 6.85 (s, 1H), 4.40 (m, 1H), 4.11 (s, 2H), 3.96 (s, 2H), 3.87 (s, 3h), 3.86 (s, 4H), 3.84 (s, 3H), 3.83 (s, 3H), 3.81 (s, 3H), 3.37 (br s, 2H), 3.2 (br s, 8H), 3.11 (m, 4H), 2.89 (br s, 6H), 2.81 (d, 6H), 1.86 (m, 2H), 1.68 (m, 2H); FAB ms, calcd. for C₄₈H₆₉N₁₅O₁₃K(M+K+): 1102.4836. Found: 1102.4750; UV(H₂O) λ$_{max}$298,235 nm.

(2S)-Hydroxybis(netropsin)succinamide-EDTA(1o), 18% after chromatography on silica gel and elution from an Amberlite X-AD 2 column. ¹H NMR (Me₂SO-d₆+TFA) δ 9.92 (s, 1H), 9.90 (s, 1H), 9.88 (s, 1H), 9.82 (s, 1H), 8.40 (t, 1H), 8.17 (t, 1H), 8.03 (br s, 1H), 7.21 (d, 1h), 7.20 (d, 1H), 7.18 (d, 1H), 7.17 (d, 1H), 7.08 (d, 1H), 6.96 (d, 1H), 6.91 (s, 2H), 4.50 (m, 1H), 4.10 (s, 2H), 3.95 (s, 2h), 3.85 (s, 3H), 3.84 (s, 3H), 3.83 (s, 3H), 3.81 (s, 3h), 3.79 (s, 4H), 3.34 (br s, 2h), 3.22 (m, 8H), 3.09 (m, 2H), 2.80 (d, 6H), 2.70 (m, 1h), one proton at δ 2.5 obscured by Me₂SO-d₆ impurity, 1.85 (m, 2h), 1.68 (m, 2H); UV (H₂O) λ$_{max}$299,239 nm.

(2R)-Hydroxybis(netropsin)succinamide-EDTA(1p), 71%. Spectral data matched that of 1o.

(R,R)-N-Methyl-4-(tartaramic acid)-pyrrole-2-carboxamideN,N-dimethylpropylamine (20a) and (S,S)-N-Methyl-4-(tartarmic acid)-pyrrole-2-carboxamide-N,N-dimethylpropylamine (20b) were prepared from 13 and d-and l-tartaric acids, respectively, following the procedure outlined for 15, 20a, 84%. ¹H NMR δ 9.53 (s, 1H), 8.19 (t, 1H), 7.20 (s, 1H), 6.89 (s, 1H), 4.34 (s, 1H), 4.13 (s, 1H), 3.79 (s, 3H), 3.22 (m, 2H), 2.75 (t, 2H), 2.51 (s, 6H), 1.81 (m, 2H). 20b, 73%, spectral data matched that for 20a.

(2R,3R)-Dihydroxy-(N-methylpyrrole-2-carboxamide-N,N-dimethylpropylamine-4-)-(distamycin)succinamide-t-butylcarbamate (21a) and (2S,3S)-Dihydroxy-(N-methylpyrrole-2-carboxamide-N,N-dimethylpropylamine-4-)(distamycin)succinamide-t-butylcarbamate (21b) were prepared from 20 and 14 following the procedure described for 16.21a, ¹H NMR δ 9.93 (s, 1H), 9.90 (s, 1H), 9.64 (s, 1H), 9.59 (s, 1H), 8.08 (t, 1H), 7.97 (t, 1H), 7.24 (m, 2H), 7.19 (m, 2H), 7.09 (s, 1H), 7.05 (s, 1H), 6.87 (s, 1H), 6.84 (s, 1h), 6.79 (t, 1H), 5.79 (br s, 1H), 5.78 (br s, 1H), 4.43 (s, 2H), 3.85˙ (s, 6H), 3.80 (s, 3H), 3.79 (s, 3H), 3.18 (m, 4H), 2.96 (m, 2h), 2.27 (t, 2H), 2.16 (s, 6H), 1.60 (m, 4H). 1.39 (s, 9H), 21b, 50%, spectral data matched that for 21a.

(2R,3R)-Dihydroxy-(N-methylpyrrole-2-carboxamide-N,Ndimethylpropylamine-4-)-(distamycin)succinamide(22a) and (2S, 3S)-Dihydroxy-(N-methylpyrrole-2-carboxamide-N,-N-dimethylpropylamine4-(distamycin)-succinamide (22b) were prepared from 21 following the general procedure for the synthesis of 17. 22a, 77% ¹H NMR δ 9.92 (s, 1H), 9.89 (s, 1H), 9.65 ls, 1H), 9.60 (s, 1H), 8.08 (m, 2h), 7.24 (s, 2H), 7.19 (s, 1H), 7.18 (s, 1H), 7.09 (s, 1h), 7.05 (s, 1H), 6.88 (s, 1H), 6.84 (s, 1H), 5.8 (br s, 2H), 4.44 (s, 2H), 3.85 (s, 6H), 3.81 (s, 3H), 3.79 (s, 3H), 3.2 (m, 4H), 2.65 (t, 2H), 2.24 (t, 2H), 2.14 (s, 6H), 1.61 (m, 4H). 22b, 65%, spectral data matched that for 22a.

(2R,3R)-Dihydroxy-(N-methylpyrrole-2-carboxamide-N,Ndimethylpropylamine-4-)-(distamycin)succinamide-EDTA-triethyl ester (23a) and (2S,3S)-Dihydroxy-N-methylpyrrole-2-carboxamideN,N-dimethylpropylamine-4-)(distamycin)succinamide-EDTA, triethyl ester (23b) were prepared from 22 following the procedure described for 19. 23a, 52%. ¹H NMR δ 9.94 (s, 1h), 9.92 (s, 1h), 9.67 (s, 1H), 9.62 (s, 1H), 8.06 (m, 2h), 8.00 (t, 1H), 7.25 (s, 2H), 7.19 (s, 2H), 7.10 (s, 1H), 7.05 (s, 1H), 6.87 (s, 1H), 6.84 (s, 1H), 5.84 (br s, 2H), 4.45 (s, 1H), 4.43 (s, 1H), 4.06 (m, 6H), 2.72 (m, 4H), 2.24 (t, 2H), 2.14 (s, 6H), 1.61 (m, 4H), 1.17 (m, 9H). 23b, 50%, spectral data matched that for 22a.

(2R,3R)-Dihydroxy-(N-methylpyrrole-2-carboxamide-N,Ndimethylpropylamine-4-)-(distamycin succinamide-EDTA, triethyl ester (23a) and (2S,3S)-Dihydroxy-N-methylpyrrole-2-carboxamideN,N-dimethylpropylamine-4-)(distamycin)succinamide-EDTA, triethyl ester (23b) were prepared from 22 following the procedure described for 19. 23a, 52%. ¹H NMR δ 9.94 (s, 1H), 9.92 (s, 1H), 9.67 (s, 1H), 9.62 (s, 1H), 8.06 (m, 2H), 8.00 (t, 1H), 7.25 (s, 2H), 7.19 (s, 2h), 7.10 (s, 1H), 7.05 (s, 1H), 6.87 (s, 1H), 6.84 (s, 1H), 5.84 (br s, 2h), 4.45 (s, 1H), 4.43 (s, 1H0, 4.06 (m, 6H), 3.85 (s, 6H), 3.80 (s, 3H), 3.79 (s, 3H), 3.61–3.48(series of singlets, 8H), 3.17 (m, 6H), 2.72 (m, 4H), 2.24 (t, 2H), 2.14 (s, 6H), 1.61 (m, 4H), 1.17 (m, 9H). 23b, 50%, spectral data matched that for 22a.

(2R,3R)-Dihydroxy-(N-methylpyrrole-2-carboxamide-N,Ndimethylpropylamine-4-)-(distamycin)succinamide-EDTA (2a) and (2S,3S)-Dihydroxy-N-methylpyrrole-2-carboxamide-N,Ndimethylpropylamine-4-)(distamycin)-succinamide-EDTA (2b) were synthesized from 22 following the procedure outlines for 1.2a, 63%. 1H NMR (Me$_2$SO-d$_6$+TFA) δ 9.91 (s, 1H), 9.88 (s, 1H), 9.64 (s, 1H), 9.60 (s, 1H), 8.39 (t, 1H), 8.14 (br s, 1H), 8.00 (br s, 1H), 7.23 (d, 1H), 7.21 (s, 1H), 7.18 (d, 1H), 7.15 (s, 1h), 7.10 (s, 1h), 7.07 (s, 1H), 6.94 (d, 1H), 6.92 (s, 1H), 4.44 (s, 2H), 4.09 (s, 2H), 3.94 (s, 2h), 3.84 (s, 6H), 3.80 (s, 6H), 3.36 (br s, 2H), 3.22 (m, 8H), 3.06 (m, 2H), 2.78 (d, 6H), 1.83 (m, 2H), 1.66 (m, 2H); UV(H$_2$O) $\lambda_{max}$296,237 nm. 2b, 74%, spectral data matched that for 2a.

Determination of the Enantiomeric Purity of (R,R) and (S,S)-Tartaric Acid Starting Materials. (R,R)-Tartaric acid (d-tartaric acid, [α] D$^{23}$+15.6 (c=20, H$_2$O) and (S,S)-tartaric acid(l-tartaric acid, [α] D$^{23}$−15.2 (c=20, H$_2$O) were converted to the corresponding dimethyl esters by refluxing in acidic methanol. A 2.46:1 (by weight) mixture of the (R,R)- and (S,S)-dimethyltartrates in CDCl$_3$ (0.55M total concentration) was treated with 20 mg increments of tris[3-(heptafluoropropyl-hydroxymethylene)-(+) camphorato] europium (III)(Aldrich), and $^1$H NMR spectra were recorded at 400 MHz. Optimal resolution of hydroxyl, methine, and methyl ester resonances was observed with 0.17M shift reagent. Integration of the separated methine resonances gave a 2.6:1 ratio of enantiomers. A control experiment showed that a 1% enantiomeric impurity was clearly discernible under these conditions, and suggested a lower limit for the detection of enantiomeric impurities of 0.1%. Treatment of the individual enantiomers with the shift reagent, followed by NMR analysis, showed that each was enantiomerically pure to the limits of experimental detection. Attempts to do shift reagent studies on intermediates in the synthesis of le-p were foiled because the compounds were insoluble or aggregated (producing broadened spectra) in the non-polar solvents useful for shift reagent studies.

Cleavage of End-Labeled DNA Restriction Fragments. General. Doubly distilled water was used for all aqueous reactions and dilutions. pBR 322 plasmid DNA was grown in E. coli (strain HB 101), and isolated as previously described, except that the CsCl gradient centrifugation were performed at 42,000 rpm for 20 h at 17° C(VTi 50 rotor) and 55,000 rpm for 13 h at 17° C(VTi 65 rotor). Calf thymus (CT) DNA, from group stock, was purchased originally from Sigma and then sonicated, deproteinized, and dialyzed. Enzymes were purchased from Boehringer Mannheim or New England Biolabs. Gel scans were performed at 633 nm using LKB Ultrascan Laser densitometer models XL or 2202.

Preparation of specifically end-labeled DNA restriction fragments began by cleaving superhelical pBR 322 DNA with restriction endonuclease EcoRi. Linearized pBR 322 was labeled on the 3' ends using 5'-[α−$^{32}$P-]dATP(Amersham, 3000 Ci/mmol) in the presence of the large (Klenow) fragment of DNA polymerase 1. This procedure also included dTTP and dATP which were purchased from Pharmacia as 100 mM solutions. Removal of 5'-phosphate groups from linearized pBR 322 with calf alkaline phosphatase followed by treatment with 5'[γ-$^{32}$P]dATP(New England Nuclear, 7000 Ci/mmol) in the presence of polynucleotide kinase afforded 5'-end-labeled DNA. Digestion of both 3'-and 5'-end-labels DNA with restriction endonuclease Rsa 1 yielded 3'and 5'-end-labeled restriction fragments 167 and 517 nucleotides in length. These were isolated by preparative gel electrophoresis on a 2 mm thick, 5% 1:30 crosslinked polyacrylamid gel. The bands of DNA were visualized under UV light after staining with ethidium bromide, and were excised from the gel. The fragments were eluted into buffer (500 mM NH$_4$OAc, 10 mM MggCl$_2$, 1 mM EDTA, 0.25% SDS), microfiltered, concentrated/extracted with dry butanol, and ethanol precipitated several times before use.

DNA cleavage reactions were run in a total volume of 15 μL of a solution containg >600 cpm of $^{32}$P-end-labeled restriction fragment and CT DNA (167 μM in base pairs, bp) in 667 mM Tris base/8.3 mM NaOAc buffer (pH 7.9) was treated with 3 μL of an appropriately diluted solution of 1.Fe(II), or 3.Fe(II). After equilibration for 2 h at 37° C., cleavage was initiated by the addition of 3 μL of 25 mM dithiothreitol (DTT, Boehringer Mannheim) solution. Final concentrations were: CT DNA, 100 μM bp; Tris base, 40 mM; NaOAc, 5 mM; DTT, 5 mM. The reactions were run for 1.5 h at 37° C., then frozen, lyophilized, and resuspended in 3 μL of 100 mM Tris borate, 80% formamide solution. After heat denaturation, 2 μL (estimated precision ±5%) of each sample was loaded onto a 0.2-0.6 mm thick, 40 cm long, 8% 1:20 crosslinked polyacrylamide/50% urea gel and electrophoresed at 1250 V or at 30 W. Gels were then transferred to chromatography paper (Whatman 3 mm Chr.), dried on a Bio-Rad Model 483 Slab Dryer, and autoradiographed at −78° C. using Kodak X-Omat AR film. The DNA cleavage patterns were quantified by densitometry. The relative peak area for each site was equated to the relative cleavage efficiency at that site.

Having fully described the invention it is intended that it be limited solely by the lawful scope of the appended claims.

We claim:

1. The process of cleaving double stranded DNA by contact with a compound having the formula:

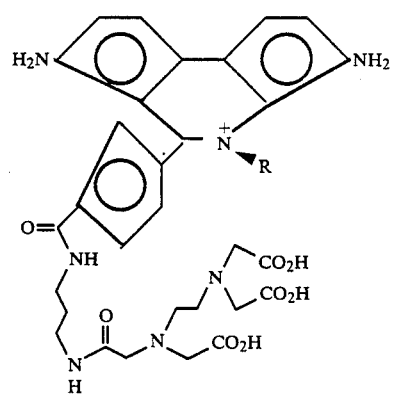

wherein the above formula, R is methyl or ethyl, in the presence of effective DNA cleavage promoting amounts of ferrous ion and oxygen.

2. The process of cleaving double stranded DNA by contact with distamycin ethylenediamine tetraacetic acid wherein ethylenediamine tetraacetic acid is tethered to the amino terminus of the N-methylpyrrole tripeptide moiety of the distamycin in the presence of effective DNA cleavage promoting amounts of ferrous ion and oxygen.

3. The process of cleaving double stranded DNA by contact with ethylenediamine tetraacetic acid distamycin wherein ethylenediamine tetraacetic acid is tethered to the carboxy terminus of the N-methylpyrrole tripeptide moiety of the distamycin in the presence of effective DNA cleavage promoting amounts of ferrous ion and oxygen.

4. The process of cleaving double stranded DNA by contact with penta-N-methylpyrrole-carboxamide ethylenediamine tetraacetic acid in the presence of effective DNA cleavage promoting amounts of ferrous ion and oxygen.

5. The process of cleaving double stranded DNA by contact with bis(ethylenediamine tetraacetic acid distamycin) in the presence of effective DNA cleavage promoting amounts of ferrous ion and oxygen.

6. The process of cleaving double stranded DNA by contact with ethylenediamine tetraacetic acid-(bisdistamycin) in the presence of effective DNA cleavage promoting amounts of ferrous ion and oxygen.

7. The process of cleaving double stranded DNA by contact with methidiumpropyl ethylenediamine tetraacetic acid in the presence of effective DNA cleavage promoting amounts of ferrous ion and oxygen.

8. The process of cleaving double stranded DNA by contact with ethidiumpropyl ethylenediamine tetraacetic acid in the presence of effective DNA cleavage promoting amounts of ferrous ion and oxygen.

* * * * *